US012544528B2

(12) United States Patent
Finlayson et al.

(10) Patent No.: US 12,544,528 B2
(45) Date of Patent: Feb. 10, 2026

(54) HUMIDIFICATION APPARATUS

(71) Applicant: Fisher & Paykel Healthcare Limited, Auckland (NZ)

(72) Inventors: Richard Reid O'neil Finlayson, Auckland (NZ); Peter Lawrence Grylls, Auckland (NZ); Yi-Cheng Sun, Auckland (NZ); Douglas Richard Wright, Auckland (NZ); Sergiu Constantin Filip, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1142 days.

(21) Appl. No.: 17/291,577

(22) PCT Filed: Nov. 7, 2019

(86) PCT No.: PCT/NZ2019/050148
§ 371 (c)(1),
(2) Date: May 5, 2021

(87) PCT Pub. No.: WO2020/096468
PCT Pub. Date: May 14, 2020

(65) Prior Publication Data

US 2022/0118213 A1 Apr. 21, 2022

Related U.S. Application Data

(60) Provisional application No. 62/828,727, filed on Apr. 3, 2019, provisional application No. 62/757,921, filed on Nov. 9, 2018.

(51) Int. Cl.
*A61M 16/16* (2006.01)

(52) U.S. Cl.
CPC ..... *A61M 16/16* (2013.01); *A61M 2205/3653* (2013.01)

(58) Field of Classification Search
CPC ........ A61M 2205/3653; A61M 16/109; A61M 2209/086; A61M 16/16–168;
(Continued)

(56) References Cited

U.S. PATENT DOCUMENTS 6,935,337 B2 8/2005 Virr et al.
7,096,864 B1 8/2006 Mayer et al.
(Continued)

FOREIGN PATENT DOCUMENTS

WO WO 2004/026382 A1 4/2004
WO WO 2004/112873 A1 12/2004
(Continued)

OTHER PUBLICATIONS

Search Report and Written Opinion received in International Application No. PCT/NZ2019/050148, dated Feb. 25, 2020.

*Primary Examiner* — Victoria Murphy
*Assistant Examiner* — Tina Zhang
(74) *Attorney, Agent, or Firm* — VIA LLP

(57) ABSTRACT

The present disclosure relates to an apparatus that can be used to humidify a stream of air that may be delivered to a patient for respiratory assistance during Positive Airway Pressure (PAP) therapy. The apparatus includes a humidification chamber and compartment that receives the humidification chamber in which the humidification chamber is secured in the compartment to enhance thermal engagement, for example, between a heater plate of the compartment and a heater base of the humidification chamber.

20 Claims, 37 Drawing Sheets

(58) Field of Classification Search

CPC ........... A61M 16/1075–1095; A61M 2205/21; A61M 11/042; A61M 2205/8206; A61M 11/005; A61M 2205/3368; F24F 6/025; F24F 13/20; F24F 2013/207; F24F 6/00–18; F24F 2006/008; E05B 1/0038; E05B 63/18; E05B 63/22; E05B 63/24; E05B 65/52; E05B 2063/0026; A61G 11/00; B65D 43/163; B65D 43/26; B65D 45/22; B65D 45/16

USPC ................ 128/202.27, 204.18; 220/262, 260

See application file for complete search history.

(56) References Cited

U.S. PATENT DOCUMENTS

| | | | | |
|---|---|---|---|---|
| 2008/0190951 | A1* | 8/2008 | Gallagher ............ | B65D 43/021 220/780 |
| 2011/0155132 | A1* | 6/2011 | Virr ....................... | A61M 16/16 128/203.26 |
| 2012/0298099 | A1* | 11/2012 | Lalonde ............. | A61M 16/021 128/200.16 |
| 2013/0247912 | A1* | 9/2013 | Loser .................... | A61M 16/10 128/204.18 |
| 2014/0264975 | A1 | 9/2014 | Bath et al. | |
| 2015/0040897 | A1 | 2/2015 | Buechi | |
| 2015/0197378 | A1* | 7/2015 | Miller .................. | B65D 43/166 29/434 |
| 2016/0129212 | A1* | 5/2016 | Dimatteo ............ | A61M 16/024 128/202.14 |
| 2017/0209664 | A1 | 7/2017 | Potharaju et al. | |
| 2019/0119012 | A1* | 4/2019 | Dagnelie .............. | B65D 50/046 |
| 2021/0379322 | A1* | 12/2021 | Maurer ................. | A61M 16/16 |

FOREIGN PATENT DOCUMENTS

| | | | |
|---|---|---|---|
| WO | WO 2007/019625 | | 2/2007 |
| WO | WO 2010/140903 | | 12/2010 |
| WO | WO 2014/138804 | | 9/2014 |
| WO | WO 2016/207838 | | 12/2016 |
| WO | WO 2017/192051 | A1 | 11/2017 |
| WO | WO 2018/094452 | | 5/2018 |
| WO | 2020065581 | A1 | 4/2020 |

* cited by examiner

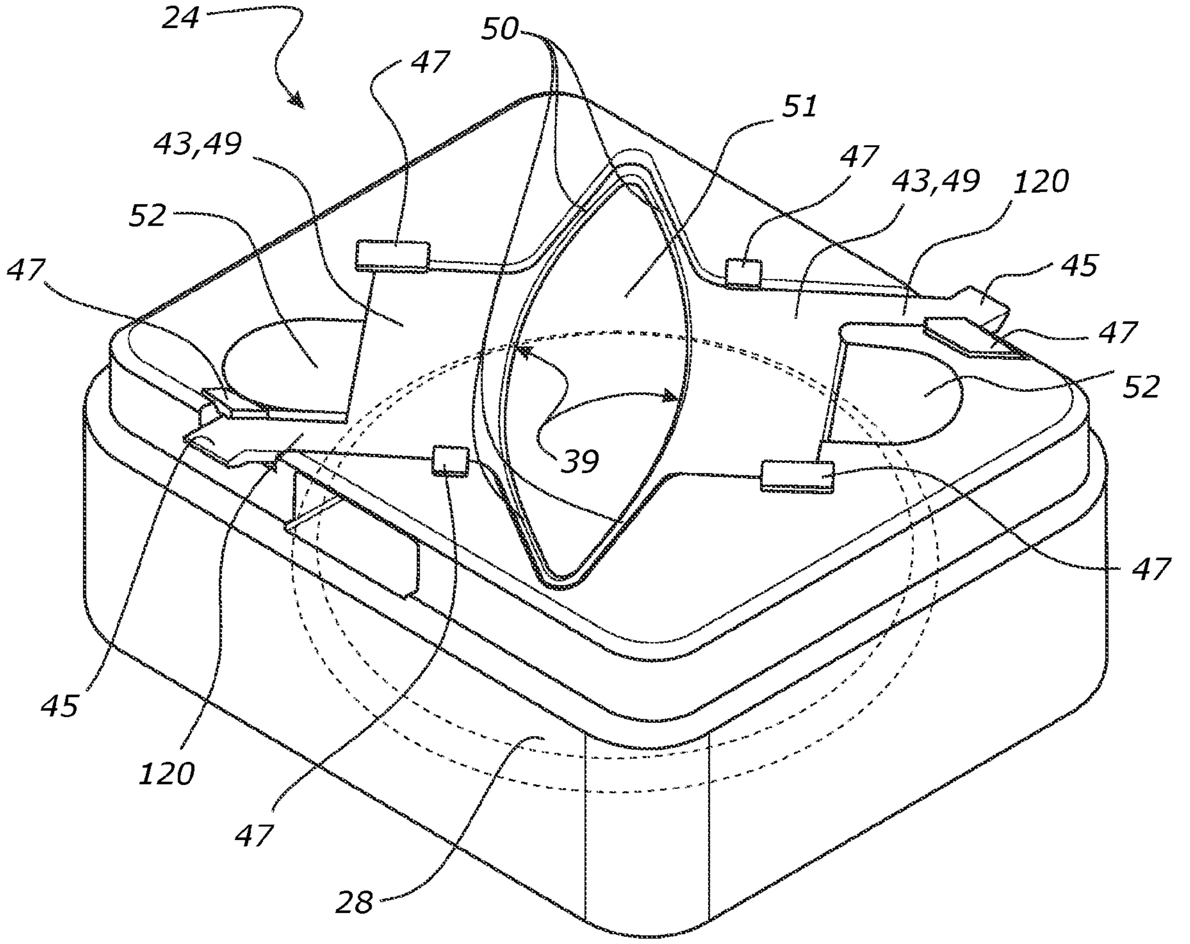
Figure 3D
Figure 3E
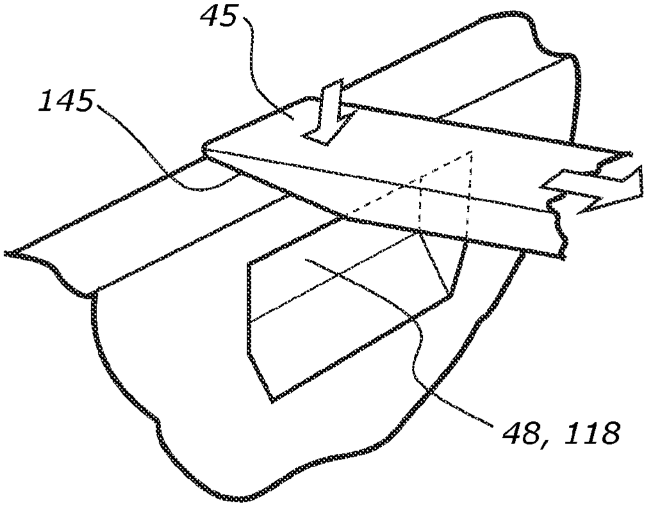

Section B-B

Section A-A

Section B-B

Section C-C

HUMIDIFICATION APPARATUS

RELATED APPLICATIONS

The present application claims priority to U.S. provisional application No. 62/757,921 filed on 9 Nov. 2018 and U.S. provisional application no. 62/828,727 filed on 3 Apr. 2019. The full contents of the specifications of both provisional applications are hereby incorporated into this specification by express reference.

FIELD OF THE INVENTION

The present invention relates to a humidification apparatus, a humidification chamber and a lid that can be used to humidify a stream of air. The stream of humidified air can be delivered to a patient for respiratory assistance and could be used in Positive Airway Pressure (PAP) therapy.

BACKGROUND

Humidification apparatus have amongst other things, a compartment with a heater plate or heating element and a humidification chamber with a heater base. During use, the humidification chamber is placed in the compartment, such that the heater base contacts the heater plate of the compartment. The heater plate is energized, and heat transfers from the heater plate to the heater base and then into water in the humidification chamber. As the air stream passes through the humidification chamber, heated water is volatilized, and the air stream is humidified.

For efficient humidification, it is desirable to have good thermal engagement between the heater plate and the heater base.

SUMMARY OF THE INVENTION

The present invention will now be described by way of a set of embodiments in which the invention may be defined by the features of each embodiment exclusively. However, it will also be appreciated that the invention may be defined by the features of two or more of the embodiments.

Embodiment Having a Coupling

An embodiment relates to a humidification apparatus including:

a humidification chamber having a heater base, a compartment having a heater plate and a compartment body that receives the humidification chamber, a coupling that acts between the humidification chamber and the body of the compartment, and the coupling is operable to hold the heater base relative to the heater plate at a holding force.

The holding force of the coupling may act against biasing, examples of biasing include:

a. in or part of the heater plate, or b. in or part of the heater base, or c. in or part of the humidification chamber, or d. in or part of the compartment body.

The coupling may hold the humidification chamber relative to the compartment body.

The coupling may be operable to allow the holding force to press the heater base to the heater plate to facilitate thermal engagement.

The holding force may be a pressing force that actively presses the heater base to the heater plate when the humidification chamber is in an operating position in the compartment body.

The holding force may be a pressing force that actively presses the heater base to the heater plate.

Ideally the heater base is pressed directly onto the heater plate.

At least part of the coupling may be on the humidification chamber and/or at least part of the coupling may be on the compartment body.

The part of the coupling on the humidification chamber may be complementary and engageable with the part of the coupling on the compartment body.

The coupling may act in a direction transverse to direction of insertion of humidification chamber into the compartment body.

The coupling may have at least one latch to hold the humidification chamber relative to the compartment body.

The coupling may have at least one recess to hold the humidification chamber relative to the compartment body.

The at least one latch may be on the humidification chamber and the at least one recess may be on the compartment body.

The latch may be complementary and engageable with the recess to hold the chamber relative to the compartment body.

The compartment body may have at least one compartment wall, wherein the compartment wall has at least one of the recesses.

The latch comprises at least one sliding shaft that is complementary and engageable with the least one recess to hold the humidification chamber relative to the compartment body.

The coupling may include the shaft on the humidification chamber and the recess on the compartment body. The recess may be a coupling opening or an undercut on the wall of the compartment body.

The shaft of the coupling may move between:

i) an active position in which the shaft acts between the humidification chamber and the body of the compartment, and ii) an inactive position.

When the shaft is in the active position, the shaft is received by and engages the recess of the compartment body.

When the shaft is in the inactive position, the shaft is disengaged from the recess and the humidification chamber can be removed from compartment.

The coupling may have a finger tab for moving the shaft. In one example, the finger tab may be a finger ring connected to the shaft(s). In another example, the finger tab may be a surface extending laterally from the shaft(s).

The coupling may have a first biasing that can move the shaft(s) from the inactive position to the active position.

The first biasing may be any suitable device including a compression spring, tension spring, coil spring and so forth.

The coupling may include two shafts that are active from opposed sides of the humidification chamber.

The compartment may have two recesses on opposed sides of the compartment body to receive the shafts.

The coupling may move in a direction transverse to a direction of insertion of humidification chamber into the compartment body when moving between the active and the inactive positions.

The two shafts each have one of the finger tabs, and the finger tabs can be operated one handed by the user, whereby the finger tabs can be squeezed toward each other to move the shafts into the inactive position, and released to allow the first biasing to move the shafts outward.

In an example, a user can use the finger tabs to operate the shafts into the inactive position in which the user can insert the humidification chamber into compartment body, or remove the humidification chamber from the compartment body.

In another example, the shafts may have a chamfered surface on the underside of outer ends of the shafts that engage the compartment body and move inwardly against the first biasing while the humidification chamber is being inserted into the compartment body, and when the outer ends of the shafts align with the recesses the first biasing can move the shafts into and engage the recesses.

The recesses may be arranged on the compartment body so that as the humidification chamber approaches the operating position within the compartment body, the heater base and heater plate engage and in order for the outer ends of the shafts to be received by the recesses in the active position, the user applies an inward force to the humidification chamber which generates the holding force, and in turn the outer ends of the shafts are aligned with and received by the recesses and the holding force is then maintained by the shafts engaging the recesses when the user stops pressing on the humidification chamber.

In order to remove the humidification chamber from the compartment, a user can place their thumb and finger of one hand into the finger tabs of the shafts and a squeeze the thumb and finger toward each other until the outer ends of the shafts are clear of the recesses, thereby moving the coupling into an inactive position.

The humidification apparatus may have an actuator for the latch.

The actuator may be operable to facilitate movement of the latch.

The actuator may be operable to retract the latch inwardly.

The actuator may be operable to extend the latch outwardly.

The actuator may be operable to:

- retract the sliding shaft to enable insertion of the humidification chamber into the compartment, and/or
- retract the sliding member from the coupling opening of the at least one compartment wall to remove the humidification chamber from the compartment.

The actuator is operable to be released to allow the sliding shaft to extend into the recess located on the at least one compartment wall to hold the humidification chamber relative to the compartment body, when the humidification chamber is in the compartment.

The actuator comprises a spring configured to:

- be pre-loaded by manipulating the actuator to enable retraction of the sliding member, and
- be released by releasing the actuator to enable extension of the sliding member.

The spring may be include one or more of: diamond-shaped spring, v-shaped, helical spring, baffle shape spring and leaf spring, compression spring or a tension spring.

The spring is made from one or more of: plastic, metal, foam, and rubber.

The latch is attached to a top surface of the humidification chamber.

The coupling includes first and second recesses, and the latch may have first and second latching members, wherein the first recess receives the first latching member and the second recess receives the second latching member to hold the humidification chamber relative to the compartment body.

The actuator may be configured to be pinched to: be pre-loaded by manipulating the actuator to enable retraction of the first and second latching members, and be released by releasing the actuator to enable extension of the first and second latching members.

The compartment body may comprise one or more additional recesses wherein there are one or more additional latching members, wherein the additional recesses are configured to receive the additional latching members to hold the humidification chamber relative to the compartment body.

The compartment may have a receptacle with a generally rectangular cross section defined by four compartment walls and a compartment base.

The heater plate may be located in or on the compartment base.

The first recess may be located on a first of the compartment walls, and the second recess may be located on a second of the compartment walls opposite to the first compartment wall.

The first recess may be located on a first corner of the first compartment wall, and the second recess may be located on a second corner diagonally opposite to the first corner.

The first recess may be located adjacent to a first corner of the compartment walls, and the second recess may be located adjacent to a second corner diagonally opposite to the first corner.

The compartment may be configured to receive the humidification chamber vertically.

The shaft may have a tapered portion comprising an underside with a sloped surface.

The sloped surface is a chamfered edge.

The holding force may be induced by a biasing of either one or a combination of:

a. in or part of the heater plate, or
b. in or part of the heater base, or
c. in or part of the coupling, or
d. in or part of the humidification chamber, or
e. in or part of the compartment body.

The humidification chamber has a base wall, a side wall extending from the base wall, a chamber inlet through which the gas stream is supplied for humidification, and a chamber outlet, an insertion clearance is provided between the compartment body and the humidification chamber, and a water spillway is provided between the humidification chamber and the compartment body that is greater than the insertion clearance, in which the water spillway is located at the chamber inlet and adjacent to the chamber inlet. In other words, in the event of the apparatus being tilted in a direction of the chamber inlet, spilt water can flow into the compartment instead of back into a compartment outlet.

The water spillway may be attributable to the shape of either one or a combination of the humidification chamber or the compartment body. For example, the water spillway may be provided by at least one of:

i) a lower portion of the chamber inlet being set inwardly relative to an upper portion of the chamber inlet; and
ii) the side wall of the humidification chamber below the chamber inlet being set inwardly to form a channel.

The channel in the side wall of the humidification chamber may be arranged upright and may extend from the chamber inlet to the base wall of the humidification chamber.

The humidification chamber may have an inner top wall and an outer top wall and an outwardly facing depression may be defined by an exposed part of the inner top wall that faces outwardly and sections of the outer top wall arranged about the exposed part of the inner top wall, and the shafts of the latch are located in the depression.

The finger tabs may be located in the depression and may be operated by a user inserting their fingers into the depression and moving the finger tabs within the depression.

The sections of the top wall arranged about the exposed part of the inner top wall may define air cavities that face inwardly into the humidification chamber.

The humidification chamber may have a first passageway extending from a chamber inlet for supplying the gas stream into the humidification chamber to a central inlet, and a second passageway extending from a central outlet to a chamber outlet for discharging the gas stream.

The first and second passageways may be at least in part formed by the inner top wall and the outer top wall.

The humidification chamber may include retention members that locate the latches relative to the inner top wall in the active and inactive positions.

The retention members may include a hub that houses inner ends of the shafts and first biasing members that engage the inner ends of the shafts to move the shafts into the active position.

The retention members may include sleeves through which the shafts move between the active and inactive positions.

The retention members may include clips that overhang the latch and/or the shafts. The clips may be adjustable between an overhanging position to retain the latch to the humidification compartment and a release position that allows the latch to be removed from the humidification chamber.

An embodiment relates to a humidification chamber that can be received by a humidification apparatus, in which the humidification chamber includes:

- a heater base,
- a coupling that acts between the body of the compartment and the humidification chamber when installed (or loaded), and the coupling is operable to hold the heater base to the heater plate at a holding force.

The humidification chamber described in the paragraph immediately above may include any one or a combination of the features described herein.

An embodiment relates to a humidification compartment, comprising:

- a body having a heater plate, in which the body receives a humidification chamber with a heater base,
- a coupling that acts between the body of the compartment and the humidification chamber, and the coupling is operable to hold the heater base relative to the heater plate at a holding force.

The humidification compartment described in the paragraph immediately above may include any one or a combination of the features described herein.

An embodiment relates to a cover for a humidification chamber having a tub with a heater base that can be received by a humidification compartment having a heater plate, and the cover comprises:

- a rigid body that can fitted to tub, and
- a coupling that acts between the cover and the compartment when the humidification chamber is received by the compartment, and the coupling is operable to hold the heater base relative to the heater plate at a holding force.

The cover may also include any one or a combination of the features of the humidification apparatus described herein.

Another embodiment relates to a humidification chamber, comprising: a heater base for installation in a compartment of a humidification apparatus, a coupling or part of coupling configured to act between the humidification chamber and the compartment when installed to hold the heater base relative to the heater plate against biasing.

Another embodiment relates to a humidification apparatus, comprising: a compartment with a body and a heater plate for receiving a humidification chamber with a heater base, a coupling or part of coupling in the compartment configured to act between the humidification chamber and the compartment body when installed to hold the heater base relative to the heater plate against biasing.

Another embodiment relates to a humidification apparatus, comprising:

- a humidification chamber, comprising:
  - a heater base,
  - a latch located in a recess on a top surface of the humidification chamber, the latch comprising:
    - a first and second latching member, the first and second latching members extending in opposite directions,
    - an actuator to operate the latching members, the actuator comprising first and second tabs,
    - a first and second support member coupling the latching members to the tabs,
    - a spring disposed to bias the tabs away from each other, and
- a compartment body comprising:
  - a heater plate,
  - a cavity defined by four compartment walls and a compartment base, the
  - heater plate located on the compartment base, and
  - a recess provided in one or more compartment walls corresponding to the latching members.

Another embodiment relates to a humidification apparatus, comprising:

- a humidification chamber, comprising:
  - a heater base,
  - a latch located in a depression on top of the humidification chamber, the latch comprising:
    - first and second sliding shafts that extend in opposite directions,
    - first and second finger tabs being connected to the shafts,
    - a spring disposed to bias the finger tabs away from each other, and
- a compartment body comprising:
  - a heater plate,
  - a receptacle defined by a side wall and a base wall, the heater plate located on the base wall, and
  - recesses provided in the side wall that receive the shafts when the humidification chamber is received by the compartment body in an operating position.

The embodiment under this heading may include any one or a combination of the features described under other headings, including other embodiments described in the section Summary of Invention.

Embodiment Having a Holder for Applying a Pressing Against the Humidification Chamber An embodiment relates to a humidification apparatus including:

- a humidification chamber having a heater base,
- a compartment having a heater plate and a body that receives the humidification chamber, and a holder that engages the body of the compartment in an operative position and wherein the holder overlays only part of the humidification chamber and presses against the humidification chamber so that the heater base is held to the heater plate by a holding force.

The apparatus may include a lid that closes the humidification chamber, wherein the holder engages the lid and the lid applies the holding force to the humidification chamber.

An embodiment relates to a humidification apparatus including:

a humidification chamber having a heater base, a compartment having a heater plate and a body that receives the humidification chamber, a lid that closes the humidification chamber, and a holder that engages the body of the compartment in an operative position and applies a holding force to the lid that holds the heater base of the humidification chamber against the heater plate.

The holder may overlay the lid.

The holder may overlay only part of the lid.

The holding force applied to the lid by the holder may also seal the humidification chamber with the lid.

The holder applies the pressing forcing to the lid when the holder is located in an operative position.

The holder maybe located in an inoperative position in which the holding force is not applied to the lid, and the lid may remain in a position to close the humidification chamber.

The lid may have an inner cover (the tub cover).

The lid may have an outer cover that at least partially overlays the inner cover (notionally the compartment lid).

The holding force of the holder may be applied to at least one of the inner cover or the outer cover.

The inner cover and the outer cover may be separable.

The holding force can prevent the separation of the heater base and the heater plate when the holder is in the operative position. The holding force facilitates thermal engagement between the heater base and the heater plate.

The holding force may have a component that is normal to the plane of the heater base and the heater plate. Ideally, the heater base and the heater plate have parallel planes.

The holding force may be generated by the holder engaging the body of the compartment.

An inner face of the holder may be configured to engage the humidification chamber. For example, the inner face of the holder may have a load point or notches for applying load to the humidification chamber at predetermined locations.

The holder may be attached to at least two engagement locations on the body of the compartment when located in the operative position.

The holder may directly engage the humidification chamber when in the operative position.

The holder may indirectly engage the humidification chamber when in the operative position. For example, the compartment may have a lid over the humidification chamber that contacts the humidification chamber, and the holder may engage the lid, which in turn, engages the humidification chamber.

The holder may releasably engage at least one of two engagement points. Optionally, the holder may be arranged to engage two engagement points.

One of the engagement points may be a hinge that allows the holder to be pivoted open from the operative position.

One of the engagement points may be a latch that is operable to secure the holder in the operative position.

A user may move the holder into the operative position, and operate the latch.

The latch may be any suitable device, including a sliding latch, an over centre lever mechanism, or a rotating latch.

The opening of the compartment may have a lengthwise direction from front-to-back, and a widthwise direction from side-to-side, and the holder may have a moveable body that is sized to extend over only part of the width of the opening.

The holder may have a moveable body that extends across the entire length of the compartment.

The movable body may be rigid in the lengthwise direction.

The holder does not seal the opening of the compartment.

The holder may apply the holding force by engaging the inner cover of the lid. In this situation the lid may not have an outer cover.

The holder may have a peripheral outer frame and a central opening, and the peripheral frame may engage the humidification chamber to apply the holding force.

The outer frame may engage the inner cover of the lid to apply at least part of the holding force.

The outer frame may engage the outer cover of the lid to apply at least part of the holding force.

The inner cover may protrude from the outer cover.

The central opening of the holder may receive the outer cover, in which an outer face of the peripheral frame and an outer face of the outer cover are (substantially) aligned when the holder is in an operative position.

The holder may have a collar structure that engages the humidification chamber. The collar structure may have a central opening.

The moveable body of the holder may include at least two segments that are articulated together in a line such that the segments can change orientation relative to each other.

The body of the holder may have at least two segments that are pivotally interconnected at a pivot connection, and when the holder is in the operative position, the holder is located to overlay the humidification chamber.

At least one of the segments of the body of the holder may be flexible.

At least one of the segments of the body of the holder may be rigid.

Optionally, at least two of the segments of the holder may be rigid.

The body of the holder may include a flexible strap that is flexible along at least part a length of the strap.

An embodiment relates to a humidification compartment, comprising:

a body having a heater plate, in which the body can receive a humidification chamber having a heater base, and a holder that overlays only a part of the humidification chamber, and the holder has an operating position in which the holder engages the humidification chamber to hold the heater base relative to the heater element by a holding force.

The humidification compartment described in the paragraph immediately above may include any one or a combination of the features described herein.

An embodiment relates to a lid and holder assembly that can be fitted to a humidification apparatus including a chamber having a heater base, and a compartment having a heater plate and a body that receives the humidification chamber, wherein:

the lid can be used to close the humidification chamber, and the holder engages the body of the compartment in an operative position and applies a holding force to the lid that holds the heater base of the humidification chamber against the heater plate.

The holder of the assembly may include any one or a combination of the features of the holder described above, including a peripheral outer frame and a central opening, in which the peripheral frame may engage the lid to apply the holding force.

The lid of the assembly may include any one or a combination of the features of the lid described herein, including an inner cover (the tub cover) and an outer cover that at least partially overlays the inner cover.

The embodiment under this heading may include any one or a combination of the features described under other headings, including other embodiments described in the section Summary of Invention.

Embodiments Having a Detachable Lid

An embodiment relates to a humidification apparatus including:

a humidification chamber having a heater base, a compartment having a heater plate and a body that receives the humidification chamber through an opening in the compartment, and a detachable lid that can be attached to close, and detached to open, the opening of the compartment.

The lid may press against the humidification chamber when the lid is attached to the compartment, so that the heater base is held to the heater plate by a holding force.

The compartment may be sealed about the opening when the lid is attached to the compartment. The seal may be provided by a gasket member that is arranged to seal the opening when the lid is attached.

The lid and the compartment may have a closure mechanism that allows the lid to be attached to the compartment by sliding the lid over the opening to close the opening.

The closure mechanism may include a first engagement formation on the lid that engages a co-operating second engagement formation on the compartment which allows the lid to be slidably attached to the compartment.

The first engagement formation of the lid and the co-operating second engagement formation for the compartment may include a cavity that operably receives a positioning limb when the lid is slid over the opening to attach the lid.

In one example, the lid may have the cavity and the compartment may have the positioning limb.

In another example, the lid may have the positioning limb and the compartment may have the cavity.

In yet another example, the lid and the compartment may each have the position limb and the cavity.

The positioning limb may be provided by any suitable formation, including a lip, a projection, a tongue, or rod, a shaft and so forth.

The cavity may be provided by any suitable formation, including a slot, groove, channel, recess and so forth.

The lid is attached to the compartment by sliding the lid over the opening by an amount that is at least equal to the distance that the positioning limb travels into, or along, the cavity.

The body of the compartment may have a rear wall, a front wall, and opposite side walls extending between the rear wall and the front wall. The second engagement formation may be located at or toward the rear wall of the compartment and the first engagement formation may be located at or toward a rearward aspect of the lid, and the closure mechanism may be operated to attach the lid by engage the first and second engagement formations by sliding the lid to engage or couple the formations.

The lid may be detached by decoupling the first and second formations.

In one example, the closure mechanism may include: i) an overhanging formation on the compartment which defines the cavity between the body of the compartment and the overhanging formation, and ii) a lip formation on the lid that is received by the cavity when the lid is attached to the compartment.

In another example, the closure mechanism may include: i) an overhanging formation on the lid, which defines the cavity, and ii) a lip formation on the lid that is received by the cavity when the lid is attached to the compartment.

The lip formation underlies the overhanging formation when the lid is attached to the compartment.

The lip formation and the overhanging formation are arranged so that the overhanging formation applies a downward pressure on the lip formation when the lid is attached to the compartment.

Part of the closure mechanism may be integrally formed with the body of the compartment.

The overhanging formation may be integrally formed with the body of the compartment.

For example, the overhanging formation may include part of a side wall of the compartment, and in particular the overhanging formation may form an outer edge of the side wall of the compartment.

Even when the lid is detached from the compartment, the lid may be connected to the compartment, for example, via a tether.

The apparatus may have an auxiliary component that can be installed on the compartment, in which the auxiliary component has the second engagement formation of the closure mechanism.

For example, the auxiliary component may include the cavity for receiving a positioning limb of the lid. In another example, the auxiliary component may have the position limb that is received by a cavity of the lid. In yet another example, the auxiliary component may have both the cavity and the position limb, which co-operates with the position limb and the cavity respectively of the lid.

The auxiliary component may be fixed to the body of the compartment using any suitable means, including any one or a combination of, an adhesive, a clip, or hinge joint toward a rear wall of the compartment.

In another embodiment, an attachment face of the auxiliary component may have a pre-applied adhesive that is protected prior to installation by a peel strip. The peel strip is removed shortly prior to installation. The pre-applied adhesive may be a pressure adhesive.

In one example, the auxiliary component may have a body that extends about at least part of the perimeter of the opening the compartment.

In another example, the auxiliary component may extend entirely around the perimeter of the opening of the compartment.

In one embodiment, the compartment may have overhanging formations on each side of the compartment which define elongate cavities, and the lid has lip formations that extend on opposite sides of the lid so that the lid can be attached to the compartment by sliding the lip formation along the cavity of the compartment.

The lid may have a skirt about at least part of the perimeter of the lid, and the lip formation extends inwardly of the skirt.

The skirt may have an outer face that aligns with an outer face of the body of the compartment when the lid is attached to the compartment.

In one embodiment, the compartment may have an overhanging formation arranged at one side of the compartment, and the lip formation is arranged at a corresponding side of the lid, and the lid is attached to a compartment by locating the lip formation under the overhanging formation.

The overhanging formation is arranged to overhang the body of the compartment.

The overhanging formation may be located at the rear of the compartment which defines a forwardly facing cavity, and the lip formation of the lid may be located at a reward end of the lid, and the lid may be attached to the compartment by the lip formation being received by the cavity.

The forward-facing cavity may extend over half the width of the compartment, and suitably over three quarters of the width of the compartment. The overhanging formation may have a top panel which defines the height of the cavity and side walls the interconnect the top panel to the compartment define the width of the compartment.

The overhanging formation may also have a divider that extends toward the compartment, and the divider is arranged to be received by recesses formed in the lip formation when the lip formation is position under the overhanging formation. The divider may help guide the lip formation into a correct position under the overhanging formation and restrict lateral movement.

The lip formation may be sized to be frictionally received within the cavity.

In one embodiment, the cavity of the closure includes a forward-facing saddle located toward the rear of the opening, and the position limb of the closure is a rod attached to the lid.

The lid is attached to the compartment when the rod is received by the saddle formation and the rod is located toward the base of the saddle formation.

The saddle formation includes a top wall that presses downward on the rod of the lid when the lid is attached to the compartment.

In another embodiment, the cavity of the closure is a rearward facing saddle located toward the rear of the lid, and the positioning limb of the closure is a rod formation located toward the rear of the opening.

The saddle formation includes a bottom wall and the rod presses downward on the bottom wall when the lid is attached to the compartment.

The apparatus of any one of the embodiments described herein may include a latch that is operable to secure the lid when attached to the compartment. The latch may include any suitable device, and may for example, be located at any point about the perimeter of the lid. For example, the latch may be located at the rear wall, the front wall or at the side walls.

An embodiment relates to a detachable lid for closing an opening of a compartment having a heater plate and a body that receives the humidification chamber, the lid including:

- a rigid body that can be attached to the compartment to close the opening, and detached from the compartment to open the opening, and
- a closure mechanism having a first engagement formation that engages a co-operating second engagement formation on the compartment which allows the lid to be attached to the compartment.

The closure mechanism may be operable to releasably attach the lid to the compartment by sliding the lid over and closing the opening, and the opening is opened by detaching the lid.

The closure mechanism of the lid may include any one or a combination of the features of the humidification apparatus, and the closure mechanism thereof described herein.

An embodiment relates to an auxiliary component that can be installed on the compartment of a humidification chamber, the auxiliary component includes an engagement formation that co-operates with an engagement formation of the lid to allow the lid to be attached and detached.

The auxiliary component described in the paragraph immediately above may also include any one or a combination of the features the auxiliary component or the closure mechanism described herein.

An embodiment relates to a humidification compartment including:

- a compartment having a heater plate and a body that receives a humidification chamber through an opening in the compartment, and
- a closure mechanism includes a first engagement formation that co-operates with a second engagement formation of the lid, so that the lid can be attached to close the opened and detached to open the opening.

The humidification compartment described in the paragraph immediately above may include any one or a combination of the features described herein.

The embodiment under this heading may include any one or a combination of the features described under other headings, including other embodiments described in the section Summary of Invention.

Embodiments Having a Holder Including a Support and Engaging Member

An embodiment relates to a humidification apparatus including:

- a humidification chamber having a heater base,
- a compartment having a heater plate and a body having an opening that receives the humidification chamber, and
- a holder including a support and an engaging member, wherein the support is movable relative to the compartment, and the holder is operable between a holding configuration and a non-holding configuration, and in the holding configuration the engaging member presses against the humidification chamber so that the heater base is held to the heater plate by a holding force.

The engaging member may be mounted to the support.

The holder may be moved from the holding configuration into the non-holding configuration by moving the support relative to the compartment.

The holder may be moved between the holding configuration and the non-holding configuration by operating the engaging member.

The holder may be moved from the holding configuration into the non-holding configuration by moving the support relative to the compartment by operating the engaging member.

The engaging member may be operated independently of the movement or position of the support. For example, in one situation it possible that the engaging member may be non-moveable relative to the compartment.

The holder may include a lever that is connected to the engaging member to move the engaging member to press against the humidification chamber.

The lever may move the engaging member so that the engaging member stops pressing against the humidification chamber.

In one example, the support may be moved relative to the compartment to close the opening of the compartment in which the holder is operable between the holding configuration and the non-holding configuration, and to open the opening of the compartment in which the holder is unable to press against the humidification chamber.

In another example, the support may be detachable from the compartment. In this example, the support may be attached to the compartment in which the support closes the opening and the holder is operable between the holding configuration and the non-holding configuration, and the support may be detached from the compartment in which the holder is unable to press against the humidification chamber.

The engaging member may include a cam surface that is pivotally mounted about a pivot axis.

The cam surface may be asymmetric about the pivot axis.

The cam surface may be an outer surface of the engaging member.

The lever may be connected to the engaging member so that the lever stands upward to the support when the engaging member is in a non-operative position.

The lever may be connected to the engaging member so that the lever pivots toward the support to cause the engaging member to press against the humidification chamber.

The lever may be received within a recess of the support when the engaging member presses against the humidification chamber.

The lever may be received within a recess of the holder when the lever is pivoted downward.

The lever may be received entirely within the recess when the lever is pivoted downward.

The lever may provide a handle for removing the humidification chamber from the apparatus.

The support may extend over an opening of a humidification apparatus and is movable relative to the compartment.

The support may have a body that does not press against the humidification chamber.

In one example, the support may include a lid that closes the humidification chamber.

In another example, the support may include a lid that closes the compartment.

In yet another example, the support may be a strap that only partially overlays the humidification chamber.

The support may be pivotally mounted to the compartment.

The support may be slidably mounted to the compartment.

In another example, the holder includes a slider that can be translated from side-to-side to move the engaging member to press against the humidification chamber.

The cam surface may have a radius of curvature that varies about the pivot axis. Examples of the cam surface include elliptical or snail shaped cam surfaces.

The cam surface may have a first reduced radii section from the pivot axis which faces the humidification chamber when in the engaging member is pivoted into a neutral position.

The cam surface may have a first enlarged radii section from the pivot axis which faces the humidification chamber when in the engaged position.

The cam surface may include a linear section at the first enlarged radii section. The linear section that presses against the humidification chamber when the engaging member is pivoted into the engaging position.

The linear section may be located toward an end of the active cam surface. The linear section may stabilize the engaging member in the engaging position. In this situation, the linear section may provide a first means for securing the engaging member in the engaging position.

The engaging member may have an inner surface on which the engaging member pivots.

The holder may have post on which the inner surface of the engaging member pivots.

The engaging member and post may provide an interference fit between the post and the inner surface of the engaging member at a position in which the engaging member is in the engaging position.

The interference fit may be provided by a raised notch on the post at a position that faces toward the humidification chamber, which increases the friction between the inner surface of the engaging member and the post as the engaging member presses harder against the humidification chamber.

The inner surface of the engaging member may have a circumferential depression that receives the raised notch when the engaging member is positioned in the neutral position.

The interference fit can be overcome by a user manually.

The engaging member may be releasably held in the engaged position by an over-centre action. For example, the cam surface may also include a second enlarged radii section between the first reduced radii section and the first enlarged radii section, in which the second enlarged radii section is greater than the first enlarged section. When moving from the neutral position to the engaging position, the engaging member passes through a maximum pressing of the humidification chamber to reach the engaging position.

An embodiment relates to a holder for a humidification apparatus having a compartment body that receives a humidification chamber, the holder including:

- a support for extending over an opening of a humidification apparatus, and
- an engaging member mounted to the support,
- wherein the holder is operable between a holding position and a non-holding position, and in the holding position the engaging member presses against the humidification chamber so that the heater base is held to the heater plate by a holding force.

The holder described in the paragraph immediately above may include any one or a combination of the features described herein.

The support may be attached to the compartment and movable relative to the compartment.

The holder may be a lid that the can be mounted to the compartment and is operable for opening and closing the opening of the compartment.

The humidification chamber described in the paragraph immediately above may include any one or a combination of the features described herein.

An embodiment relates to a humidification compartment for receiving a humidification chamber having a heater base, the compartment having:

- a heater plate and a body having an opening that receives the humidification chamber, and
- a holder including a support and an engaging member, wherein the support is movable relative to the opening of the compartment, and the holder is operable between a holding position and a non-holding position, and in the holding position the engaging member presses against the humidification chamber so that the heater base is held to the heater plate by a holding force.

The humidification compartment described in the paragraph immediately above may include any one or a combination of the features described herein.

The embodiment under this heading may include any one or a combination of the features described under other headings, including other embodiments described in the section Summary of Invention.

First Embodiment Having a Coupling that Acts Between the Humidification Chamber and the Body of the Compartment An embodiment relates to a humidification apparatus including:

- a humidification chamber having a heater base,
- a compartment having a heater plate and a body that receives the humidification chamber,
- a coupling that acts between the humidification chamber and the body of the compartment, and the coupling is operable to hold the heater base against the heater plate at a holding force.

The coupling may hold the humidification chamber relative to the compartment body.

The coupling may include a shaft that holds the humidification chamber relative to the compartment body.

The coupling may include a recess for holding the humidification chamber relative to the compartment body.

The coupling may include a shaft on the humidification chamber and the recess is on the compartment body. The recess may be an opening or undercut on the wall of the compartment body.

The shaft of the coupling may move between:

- i) an active position in which the shaft acts between the humidification chamber and the body of the compartment, and
- ii) an inactive position.

The coupling may have a button arranged for manually moving the shaft between the active position and the inactive position.

Operating the button may move the shaft from the active position to the inactive position.

The coupling may have a first biasing that can move the shaft from the inactive position to the active position.

The first biasing may be any suitable device including, a compression spring, tension spring, coil spring and so forth.

The biasing may be connected to the shaft.

The coupling may have a translator for translating movement of the button to movement of the shaft. Suitably, the translator translates movement of the button to move the shaft from the active position to the inactive position.

The translator may interconnect the button and the shaft to move the shaft toward the button and away from the button.

The shaft may move toward the button when moving from the active position to the inactive position, and the shaft may move away from the button when moving the inactive position to the active position.

The button may be operably connected to the shaft so that the button moves in a direction laterally to the direction of movement of the shaft.

The translator may be operable in translating movement of the button to move the shaft from the active position to the inactive position, in which the button moves in a normal direction to the direction of movement of the shaft.

The translator may be a linkage that is pivotally connected to the shaft at a first pivot point and pivotally connected to the button at a second pivot point.

The second pivot point may be fixed relative to the button.

The second pivot point may move relative to the button.

The button may be a push button and/or a pull button.

The button may have a lock mechanism that is operable to lock the shaft in the inactive position.

The lock mechanism may operate against the bias of the operating button.

The button may be pressed inwardly to move the shaft from the active position to the inactive position.

The button may be pressed inwardly to move the shaft from the inactive position to the active position.

The button may be pulled outwardly to move the shaft from the active position to the inactive position.

The button may be pulled outwardly to move the shaft from the inactive position to the active position.

The button may be operably connected to the shaft so that side-to-side movement of the button drives the shaft between the active and inactive positions.

The button may be operably connected to the shaft so that rotational or pivotal movement of the button drives the shaft between the active and inactive positions.

The shaft may be configured to hold the humidification chamber relative to the compartment body.

The coupling may include two shafts that are active from opposite sides of the humidification chamber.

The compartment may have two openings or undercuts on opposite sides for receive the shafts.

The coupling may be mounted in a passageway formed in a lid of the humidification apparatus. The coupling may be encapsulated in the passageway.

The passageway may include multiple segments, in which one segment houses the shaft and another segment houses the button.

The holding force may be a pressing force that actively presses the heater base to the heater plate. The holding force may be generated by a second biasing.

The coupling may move in a direction transverse to a direction of insertion of humidification chamber into the compartment body when moving between the active and the inactive positions.

Transverse means a direction at an angle to (that is, at least partially non-parallel to) and preferably (but not limited to) orthogonal to one or more of:

- a direction or axis of the forces causing thermal engagement ("thermal engagement forces")
- a direction or axis of the insertion movement of the humidification chamber into the compartment, and/or
- a wall the compartment and/or humidification chamber when in the upright orientation.

The lid may include an inner cover that is fitted to a humidification chamber. The lid may include an outer cover that is fitted to the compartment. The coupling may be mounted to either one of the inner cover or the outer cover.

An embodiment relates to a humidification chamber that can be received by a body of a compartment having heater base, the humidification chamber including:

- a heater base, and
- a coupling that acts between the humidification chamber and the body of the compartment, and the coupling is operable to hold the heater base relative to the heater element at a holding force.

The humidification chamber described in the paragraph immediately above may include any one or a combination of the features described herein.

The coupling may be mounted to a top cover or lid of the humidification chamber.

An embodiment relates to a humidification compartment including:

a body having a heater plate, and in which the body is configured to receive a humidification chamber having a heater base, and a coupling that acts between the humidification chamber and the body of the compartment, and the coupling is operable to hold the heater base relative to the heater element at a holding force.

The humidification compartment described in the paragraph immediately above may include any one or a combination of the features described herein.

The coupling may be mounted to the lid or outer cover of a humidification compartment.

An embodiment relates to a detachable lid for a humidification apparatus having a heater plate and a body that receives a humidification chamber, in which the lid includes:

a rigid body for closing the humidification apparatus, and a coupling that acts between the lid and the body of the humidification apparatus, and the coupling is operable to hold the heater base relative to the heater element at a holding force.

The lid described in the paragraph immediately above may include any one or a combination of the features described herein.

The embodiment under this heading may include any one or a combination of the features described under other headings, including other embodiments described in the section Summary of Invention.

Second Embodiment Having a Coupling that Acts Between the Humidification Chamber and the Body of the Compartment An embodiment relates to a humidification apparatus including:

a humidification chamber having a heater base, a compartment having a heater element (plate) and a body that receives the humidification chamber, a coupling that acts between the humidification chamber and the body of the compartment to hold the heater base relative to the heater element at a holding force.

Optionally, the coupling forms a snap fit connection that has a projection that is active between the humidification chamber and the body of the compartment.

The coupling could also be described as a detent connection having a projection that resiliently engages the compartment when the coupling engages the compartment.

The projections may resiliently engage the compartment.

The projections may resiliently engage the humidification chamber.

The coupling may include a co-operating profiled formation that contacts the projection when the coupling is engaged.

The coupling may also include a catch piece that engages the projection.

The catch piece may extend inwardly from an inner face of a wall of the compartment.

The co-operating profiled formation may include a peak and a recess, and the projection frictionally engages the peak in passing to the recess when the coupling is engaged.

The peak is any protrusion and may for example, include any lip, crest, rib, ridge, narrowing and so forth.

The recess is any section that does not protrude as far the peak and may for example, include any depression, notch, recess, valley, decline, flat, undercut, widening, opening, aperture and so forth.

The projection may be connected to the humidification chamber and the co-operating profiled formation may be located on the compartment.

The projection may be connected to the compartment and the co-operating profiled formation may be located on the humidification chamber.

The coupling may include a flexible material that allows the projection to shift.

The coupling may include a resiliently flexible section to which the projection is connected that allows the projection to shift.

The coupling may include a finger tab extending from the projection, the finger tab and the projection define a shiftable section, and the shiftable section is connected to a resiliently flexible section, so that a user can manually shift the projection by the tab to move the projection into a release position to decouple the coupling.

In one embodiment, the coupling includes a shiftable section having: i) a projection that is connected to and extends outwardly of the humidification chamber and the finger tab extends from the projection, and ii) a resiliently flexible section that connects the shiftable section to the humidification chamber. A user can shift the projection into a release position by the tab.

In another embodiment, the coupling includes a shiftable section having: i) a projection that is connected to and extends outwardly of the compartment and the finger tab extends from the projection, and ii) a resiliently flexible section that connects the shiftable section to the compartment. A user can shift the projection into a release position by the tab.

The apparatus may include two snap fit couplings that are disposed on opposite sides of the apparatus.

An embodiment relates to a humidification chamber that can be received by a humidification apparatus, in which the humidification chamber includes:

a heater base, and a part of a coupling that acts between the humidification chamber and the body of the compartment to hold the heater base relative to the heater element at a holding force.

The part of the coupling may include a shiftable projection.

The humidification chamber described in the paragraph immediately above may include any one or a combination of the features described herein.

An embodiment relates to a lid for a tub of a humidification chamber that can be received by a body of a humidification compartment, the lid including:

a rigid body for attaching to the tub of the humidification chamber; and a first part of a coupling that acts between the humidification chamber and the body of the compartment to hold the heater base relative to the heater element at a holding force.

The first part of the coupling may include a shiftable projection.

The coupling may include any one of the features of the coupling of the humidification apparatus described herein.

The lid described in the paragraph immediately above may include any one or a combination of the features described herein.

An embodiment relates to a humidification apparatus, comprising:

a compartment with a body and a heater plate for receiving a humidification chamber with a heater base, a part of a coupling that acts between the humidification chamber and the body of the compartment to hold the heater base relative to the heater element at a holding force.

The part of the coupling may include a catch.

The humidification compartment described in the paragraph immediately above may include any one or a combination of the features described herein.

The embodiment under this heading may include any one or a combination of the features described under other headings, including other embodiments described in the section Summary of Invention.

BRIEF DESCRIPTION OF THE DRAWINGS

Embodiments of the invention are illustrated in the attached Figures, of which FIGS. 3A to 4L relate to a preferred embodiment. A brief description of the Figures is as follows.

In FIG. 1A, the gas stream is supplied directly into the humification chamber, whereas in FIG. 1B the gas stream is supplied into the humidification chamber via the humidification compartment.

FIG. 3D is a perspective view of a humidification chamber with a coupling and heater base. FIG. 3E is a perspective view of a sliding member with a sloped edge for use with the recess in the compartment.

FIG. 7A illustrates the lid attached to the compartment in which the lid applies a holding force to the humidification chamber. FIG. 7B illustrates the lid in the process of being detached from the compartment and FIG. 7C illustrates an exploded view.

FIG. 8A shows the lid being attached to the compartment in which the lid applies a holding force to the humidification chamber. FIG. 8B shows the lid detached from the compartment.

DETAILED DESCRIPTION

Figure 1A:
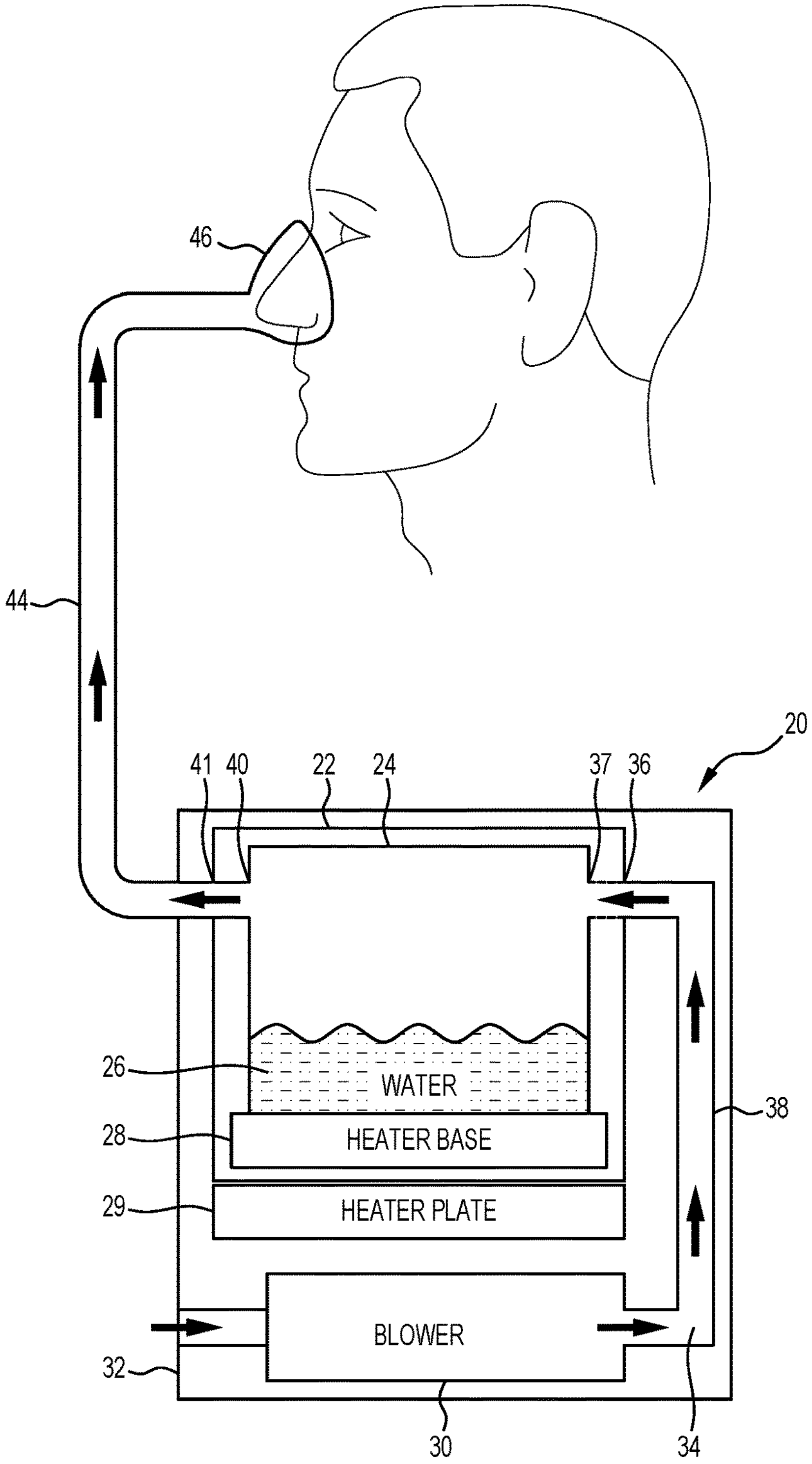
FIGS. 1A and 1B are schematic illustrations of two arrangements including a humidification compartment and a humidification chamber contained within the compartment, in which a gas stream is humidified and supplied to a recipient via a patient interface in the form of a nasal mask.

Embodiments of the present invention will now be described in the following text which includes reference numerals that correspond to features illustrated in the accompanying Figures. Where possible, the same reference numeral has been used to identify the same or substantially similar features in the different embodiments. To maintain the clarity of the Figures, however, not all reference numerals are included in each Figure.

Figure 1B:
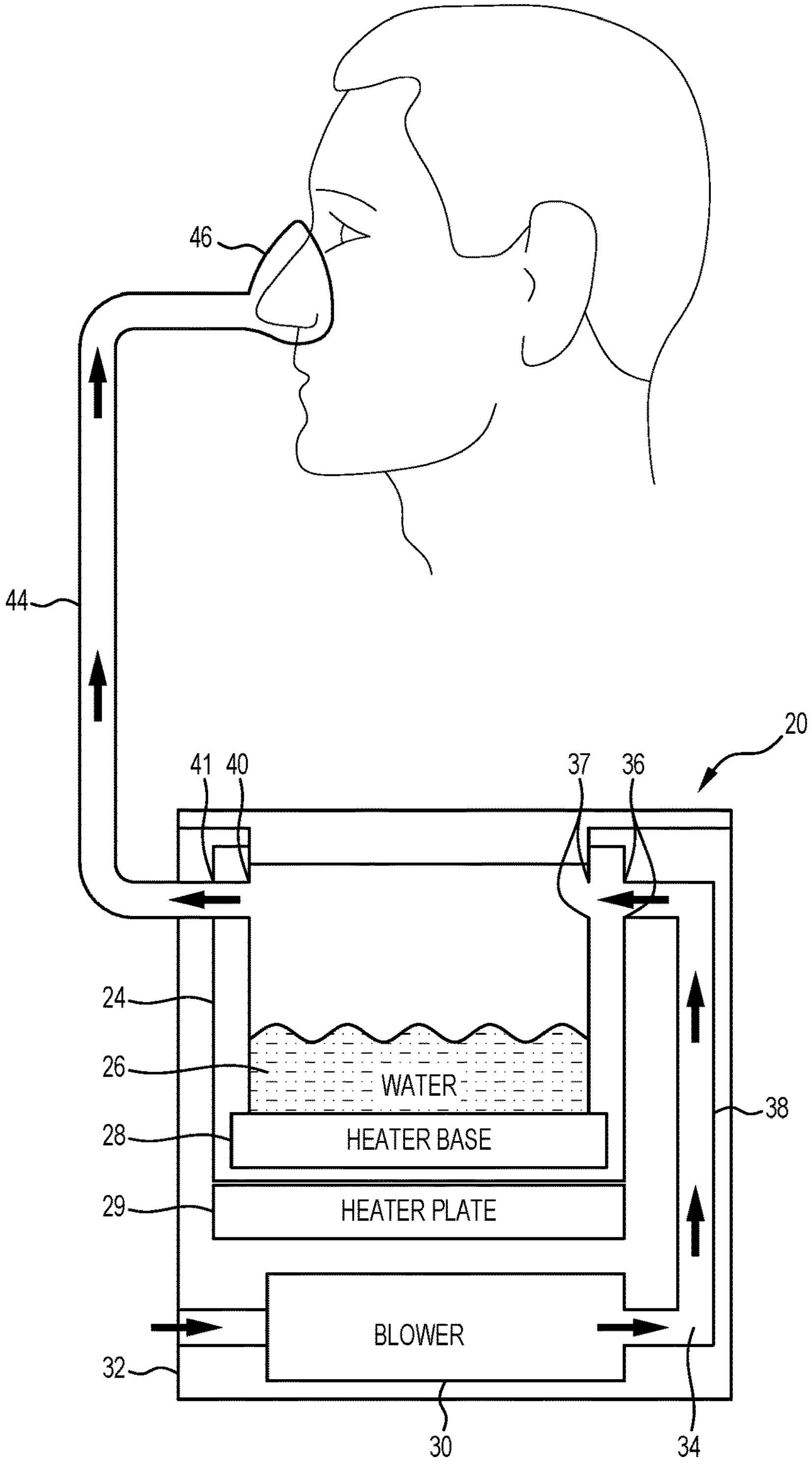

FIGS. 1A and 1B are schematic illustrations of a respiratory device having a humidification apparatus 20 including a humidification compartment 22 and a removable humidification chamber 24 that is inserted into and received by the compartment 22. The humidification chamber 24 is inserted in a vertical direction when the compartment 22 is in an upright state. The compartment 22 has a top opening, through which the chamber 24 is introduced into the compartment 22. The top opening may have a lid so the humidification chamber 24 within the humidification compartment 22 may be accessed for removal for cleaning or filling. But this is optional, and other arrangements can be envisaged. For example, in other embodiments it is possible that the chamber 24 is inserted horizontally into the humidification compartment 22.

Throughout this specification the terms "humidification compartment" and "compartment" are used interchangeably. Similarly, the terms "humidification chamber" and "chamber" are used interchangeably, and the terms "humidification apparatus" and "apparatus" are also used interchangeably.

The compartment 22 has a heater plate assembly 29 comprising among other things, an aluminium (or other suitable material) heat transfer plate, heating element, and optionally a biasing mechanism. In this specification, the heater plate assembly 29 will more generally be referred to as a "heater plate 29", which can mean the entire assembly or just the heat transfer plate as context dictates.

The humidification chamber 24 is fillable with a volume of water 26 and the humidification chamber 24 has, or is coupled to, a heater base 28. The heater plate 29 is powered to generate heat which is transferred to the heater base 28 of the chamber 24 (via the heat transfer plate 29) to heat the water 26 in the humidification chamber 24 during use.

The humidification apparatus 20 has a blower 30 which draws atmospheric air and/or other therapeutic gases through an inlet and generates a gas stream 34 at an outlet of the blower 30. FIG. 1A illustrates an arrangement in which the outlet of the blower 30 is fluidly connected directly to a chamber inlet 37 via connecting conduit 38 and a compartment outlet 36. The chamber inlet 37 and the compartment outlet 36 may have a sealed connection when the humidification chamber 24 is in the operating position.

Throughout this specification, the term "sealed connection" or variations thereof such as "sealingly connected", refers to a gas tight connection that prevents any substantial change in either the flow rate or pressure of the gas stream, as leakage from the sealed connection is minimised. By way of example, the sealed connection may include any one or a combination of a flexible pressure seal, an inflated sealing ring, O-rings, T-shaped seals, tapered fitting seals, friction fitting seals and so forth.

The gas stream 34 passes through the humidification chamber 24, where the humidity of the gas stream 34 is increased and exits via gases outlet 40 of the humidification chamber. The gases stream is delivered via a conduit 44 and a mask, cannula or similar patient interface 46 to a patient.

In the arrangement shown in FIG. 1A, a chamber outlet 40 is sealingly connected to, or sealingly engaged with, a compartment inlet 41 by a sealed connection. In this embodiment, a lid to the compartment may or may not be provided.

Figure 2:
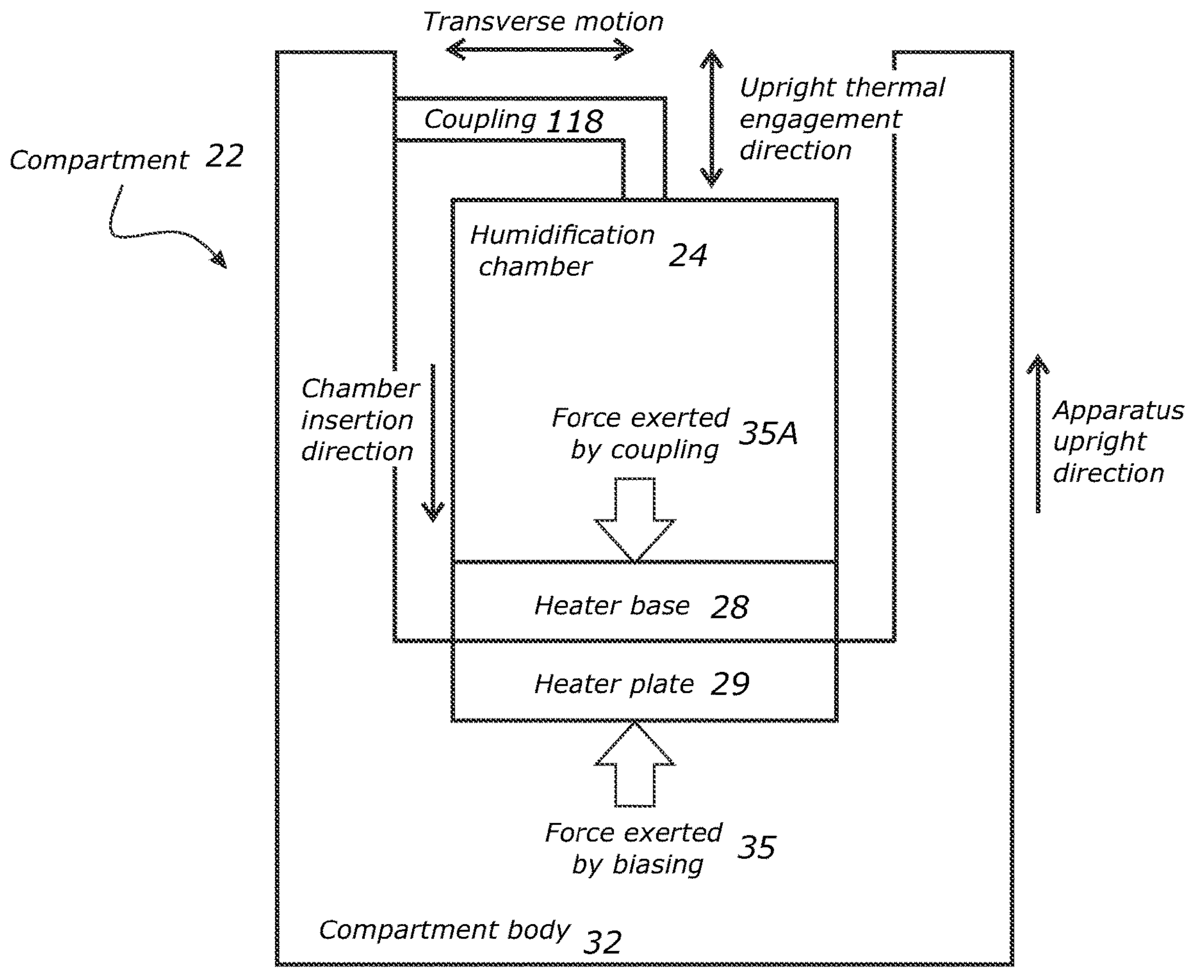
FIG. 2 is a schematic illustration showing the interactions between the heater base and heater plate according to a general embodiment of the present invention.

FIG. 1B illustrates an arrangement in which the outlet of the blower 30 is fluidly connected to a chamber inlet 37 via the compartment outlet 36. Specifically, gases from the outlet of the blower 30 are directed into the humidification compartment 22 and the stream of air and/or other gases flows from the compartment 22 into the chamber inlet 37. One of the advantages of the arrangement shown in FIG. 2 is that there is no or no significant pressure differential between the inside and the outside of the humidification chamber 24. As can be seen, the lids of the compartment 22 and of the chamber 24 may be combined. That is to say, the compartment 22 may have an outer lid and the chamber 24 may have an inner lid, and the inner and outer lids may be mechanically connected in a manner that allows the inner and outer lids to be separated. It is also possible that inner and outer lids may be integrally formed and are not separable.

In the arrangements of either FIG. 1A or 1B, the gas stream 34 passes through the humidification chamber 24, where the humidity of the gas stream 34 is increased, and exits via chamber outlet 40. The chamber outlet 40 is sealingly connected to, or sealingly engaged with, a compartment inlet 41. It will be appreciated that in alternative embodiments, the chamber outlet 40 and the compartment inlet 41 need not be sealingly connected by a connector or otherwise sealingly engaged. The gases stream is delivered via a conduit 44 to a patient interface 46. The patient interface may comprise one of: a nasal mask, an oro-nasal mask, an oral mask, a full face mask, a nasal cannula, and nasal pillows.

It is desirable to have thermal engagement (also known as "thermal coupling") between the heater base 28 and the heater plate 29, so that heat can be transferred to heat the water 26 in the humidification chamber 24. The heater base 28 and heater plate 29 may be said to be thermally engaged when a holding force holds the heater base 28 against the heater plate 29, thus maintaining or improving the face-to-face contact between the heater base 28 and the heater plate 29, which in turn provides efficient heat transfer from the heater plate 29 to the heater base 28. If, for example, the heater base 28 has an uneven or warped surface, heat transfer between the heater plate 29 and the heater base 28 will be inefficient, as the full surface area of the heater base 28 will not be in direct contact with the heater plate 29. However, if a force is applied to push the heater base 28 into contact with the heater plate 29 (or vice versa), this may allow more of the surface area of the heater base 28 and heater plate 29 to be in direct contact.

To provide thermal engagement the heater base 28 and heater plate 29 are held together such that there is some holding force between the two to provide good thermal coupling. For example, the holding force may include one or a combination of:

- the heater base 28 could be pressed down onto the heater plate 29, and the heater plate held in place;
- the heater plate 29 could be pushed up against the heater base 28, and the heater base 28 held in place; and/or
- the heater plate 29 could be pressed up against the heater base 28 and the heater base 28 pressed down against the heater plate 29.

A benefit of the holding force is that thermal engagement can be optimized between the heater base 28 and the heater plate 29 irrespective of the amount of water 26 contained by the humidification chamber 24, or the mass of the humidification chamber 24. Additionally, the holding force can prevent any vibration or other movement of the humidification chamber 24 in the compartment 22 during use.

With reference to FIG. 2, a general arrangement to achieve this thermal engagement is described. FIG. 2 shows a humidification apparatus comprising a humidification chamber 24 (with a heater base 28). The humidification apparatus also comprises a compartment 22 with a compartment body 32 and a heater plate 29 for receiving the humidification chamber 24. The humidification apparatus also comprises a coupling 118 and biasing mechanism that together are configured to act between the humidification chamber 24 and the compartment body 32 to facilitate thermal engagement. The coupling is configured to hold the humidification chamber relative to the compartment body, and holds the heater base relative to the heater plate at a holding force. The coupling and biasing mechanism may be separate or the biasing mechanism may form part of the coupling. For example, the biasing mechanism could be: in or part of the heater plate, or in or part of the heater base, or in or part of the coupling, or in or part of the humidification chamber, or in or part of the compartment body. When considering the interactions between the heater base 28 and the heater plate 29, the biasing mechanism (not shown) applies a force 35 that is opposed by a force 35A from the coupling 118 when the coupling is engaged, thereby holding the heater base 28 against the heater plate 29 at a holding force. That is to say, the two forces 35, 35A oppose each other to facilitate thermal engagement of the heater base 28 and heater plate 29. The coupling could, for example, provide a reaction force to the force from the biasing mechanism. The forces 35, 35A provided by the coupling and the biasing mechanism help maintain the position of the humidification chamber 24 relative to the compartment body, thus holding the heater base relative to the heater plate against the biasing to provide thermal engagement. These forces causing thermal engagement can be termed "thermal engagement forces".

Preferably the coupling is engaged and disengaged by way of a transverse motion, whereby at least a portion of the coupling moves transversely when actuated to activate/engage the coupling. Transverse means a direction at an angle to (that is, at least partially non-parallel to) and preferably (but not limited to) orthogonal to one or more of:

- a direction or axis of the forces causing thermal engagement ("thermal engagement forces")
- a direction or axis of the insertion movement of the humidification chamber into the compartment, and/or
- a wall of the compartment and/or humidification chamber when in the upright orientation.

FIGS. 3A to 3L and FIGS. 4A to 4H—Relate to a Preferred Embodiment Having a Coupling that Acts Between the Humidification Chamber and the Body of the Compartment The apparatus 20 shown in FIGS. 3A to 3L has a compartment 22 and a humidification chamber 24 that can be held together via a coupling 118. The compartment 22 comprises a compartment body 32, a heater plate 29 (shown in hidden lines), and at least one recess 48 that forms part of the coupling 118. The humidification chamber 24 comprises a heater base 28 (shown in hidden lines), and a latch 43 that forms part of the coupling 118. The humidification chamber 24 can be installed in the compartment 22.

Figure 4A:
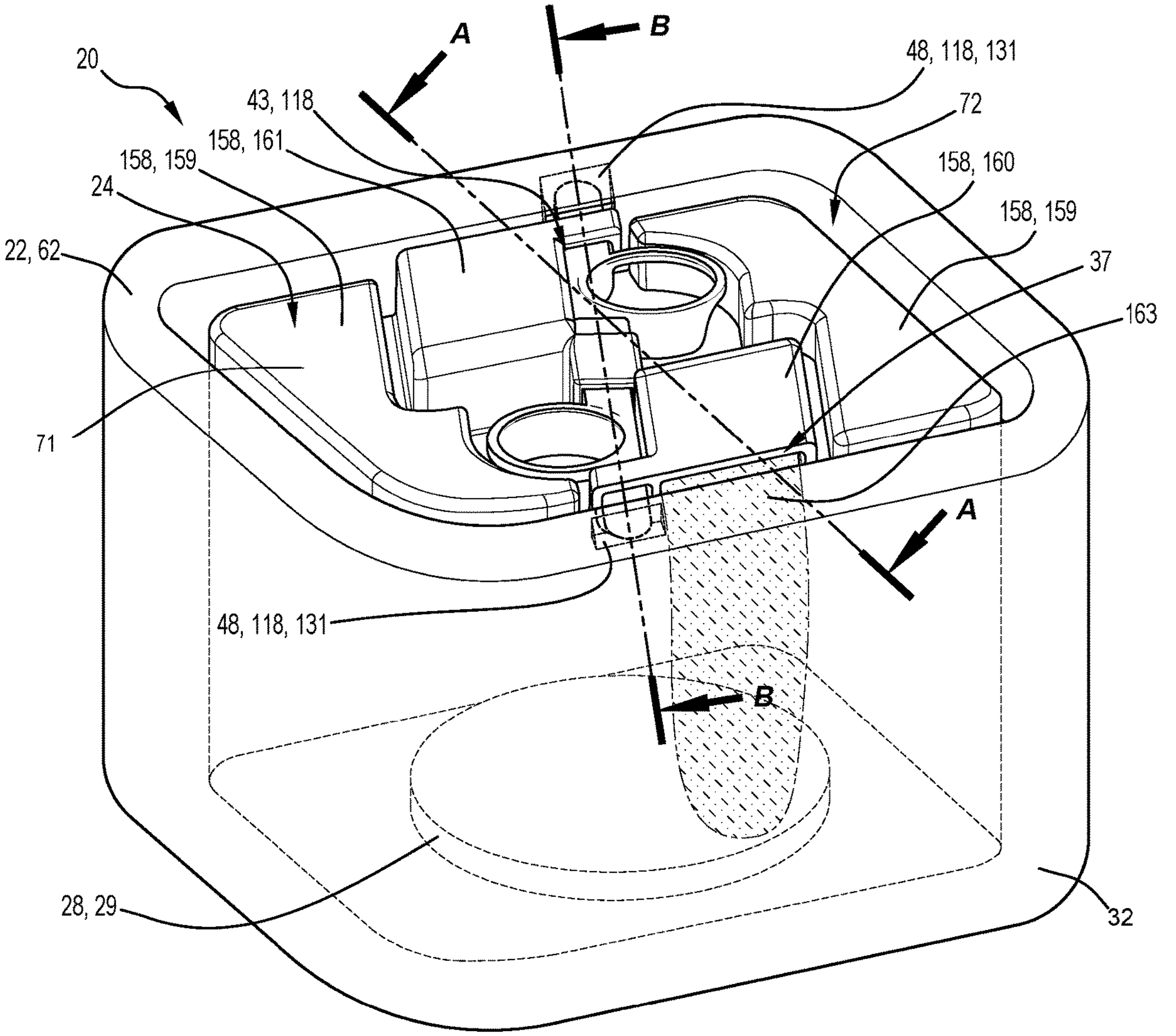
FIG. 4A is a top, front and side perspective view of an apparatus according to a preferred embodiment including a humidification chamber and a compartment that receives the humidification chamber. The humidification chamber having a coupling including shafts that engage the compartment and a chamber inlet for a gas stream on a front of the humidification chamber. The broken lines represent water spilling out of the chamber inlet.

When the humidification chamber 24 is placed in the compartment 22 and the coupling 118 is engaged, the heater plate 29 and heater base 28 can be thermally engaged with each other—such as shown in FIG. 4A. This is made possible because a holding force (or a biasing force) between the heater base 28 and the heater plate 29, can be maintained by the coupling 118 applying a force to the compartment body 32. In this embodiment, the force of the coupling 118 acting on the compartment body 32 is a reaction force. The coupling 118 holds the humidification chamber 24 relative to the compartment 22, such that the heater plate 29 is held relative to the heater base 28.

Although not shown in detail in the Figures, the heater plate 28 is vertically sprung or otherwise biased so that a force 35 (see FIG. 2) can be applied upwards onto the heater base 28 when the humidification chamber 24 is installed and the coupling 118 is engaged. A force 35A can then applied by the coupling 118 in a direction opposite to the direction of the force 35 exerted by biasing. The biasing could be for example that described in WO2010/140903 which is incorporated herein in its entirety. The force 35A provided by the coupling 118 is reactionary, and is created by the coupling 118, which comprises at least one latch 43 being engaged within at least one recess 48. The latch 43 and the recess 48 are configured to be complementary and engageable with each other to create a coupling for holding the humidification chamber 24 relative to the body 32 of the compartment 22.

When the humidification chamber 24 is in the compartment 22 and the coupling 118 is engaged with the chamber 24 in the operative position, the biased heater plate 29 is forced upwards against the heater base 28. The force 35 (see FIG. 2) exerted by biasing also forces the latch 43 in an upwards direction, as the heater base 28 and the latch 43 are part of the humidification chamber 24. A portion of the latch 43 (for example a slidable latching member) is configured to extend into the recess 48 in the compartment body 32. When a portion of the latch 43 comes into contact with an upper edge of the recess 48, the latch 43 and recess 48 are said to be coupled to create a reaction force 35A (see FIG. 2) created by the coupling that acts downwards. The coupling 118 applies a reaction force 35A onto the chamber 24 and the heater plate 29. When the force 35 exerted by the biasing is applied onto the heater base 28, and when an opposing reaction force 35A is applied onto the heater plate 29, there is thermal engagement between the heater plate 29 and the heater base 28.

There may also be no biasing in the heater plate 29, in which case, the coupling 118 is capable of pressing the heater base 28 against the heater plate at a holding force, and the holding force may in part be generated by a biasing of the heater plate 29, but if no biasing is present, the holding force may also be generated by a user pressing the humidification chamber into the compartment, which may be require for the latch 43 to engage the recess 48.

The latch 43 is disposed on the humidification chamber 24 and forms part of the coupling 118. The latch 43 and components associated with the latch 43 will now be described with reference to FIG. 3D. In the context of this specification, reference to a "latch" can generally mean any latching mechanism, which might comprise one or more than one latching member, each of which may operate independently or in unison, and may be mechanically separate or mechanically joined. Each latching member could itself be considered a latch. Therefore, reference to a "latch" could encompass multiple latches. Therefore reference to a "latch" herein should be non-limiting as to the number and nature of the latch.

The latch comprises two slidable latching members 45. In some embodiments, there may be more latching members. Each slidable latching member 45 is configured to extend in opposite directions to protrude into and be received by corresponding recess 48 on the compartment body 32. The latching members 45 move in a direction transverse to the direction in which the humidification chamber 24 moves when inserted into the compartment 22. This movement of the latching members 45 may also be in a motion transverse to the holding forces (or thermal engagement forces) between the heater plate 29 and the heater base 28. Each latching member 45 has a tapered lead-in to assist with installation and engagement. An actuator 39 is also provided on the humidification chamber 24; the actuator 39 is associated with and actuates the latching members 45. The actuator 39 can be considered part of the latch or separate to it, and/or part of the coupling or separate to it as context allows. The latch 43 comprises shafts 120 for connecting the latching member 45 to the actuator 39. The latching member 45 may be integrally formed with the shafts 120 so that the latching member 45 and the shaft 120 are a single piece. The actuator 39 is configured to facilitate movement, such as retracting and extending, of the latch. The actuator 39 comprises finger tabs 49 separated by a biasing spring 50. The biasing spring 50 is configured to operate in a clearance region 51 to bias the finger tabs 49 apart to extend the latching members 45 into a latching/operating position. The biasing spring 50 is a diamond shaped spring and made from a resilient material. Other springs could be envisaged, such as, but not limited to, a helical spring, v-shaped spring, baffle shape spring, or a leaf spring or a combination of the listed types of springs. Desirably the spring 50 is made from plastic, metal, foam, rubber, or a combination of thereof.

The finger tabs 49 can be squeezed or otherwise brought together against the biasing spring 50 to retract the latching members 45. The top surface of the humidification chamber 24 comprises a depression for receiving the latching member(s) 45, shafts 120, finger tabs 49 and spring 50 arrangement (in this context, the arrangement including the actuator tabs will be term the "latch"), and allows for lateral extension and retraction of those components on the top surface of the chamber 24. The recess 48 corresponds to the shape of the latch 43 and is lower than the top surface of the humidification chamber 24 so that the humidification chamber 24 has a flush top surface when the latch 43 is installed.

One or more depressions 52 are also provided, with each depression 52 being associated with a finger tab 49. The depression 52 is located beneath the actuator 39 to allow for easy access and space for fingers to operate on the actuator 39 and grab and insert/remove the humidification chamber 24 with one hand and/or a single movement. In some embodiments, the depression 52 is a finger grip/hole that is associated with one of the finger tabs 49. The actuator 39 comprising the finger tabs 49 in combination with the depressions 52 provide a finger grip arrangement such that a user can manipulate the actuator 39 by squeezing two finger tabs 49 with one hand. This allows for actuation of the latch 43 and removal of the chamber 24 from the compartment 22 without being required to release the actuator 39. One or more retention members 47 are placed throughout the latch 43 for securing the latch 43 to the inner top wall 157 of the humidification chamber 24. In some embodiments, the retention members 47 extend over various portions of the latch 43 to help stabilize the latch 43, including adjacent to the latching members 45, over the actuators 39, and over the shafts 120. Alternatively, the latch 43 could be retained by being enclosed or covered by a full or partial covering.

Figure 3A:
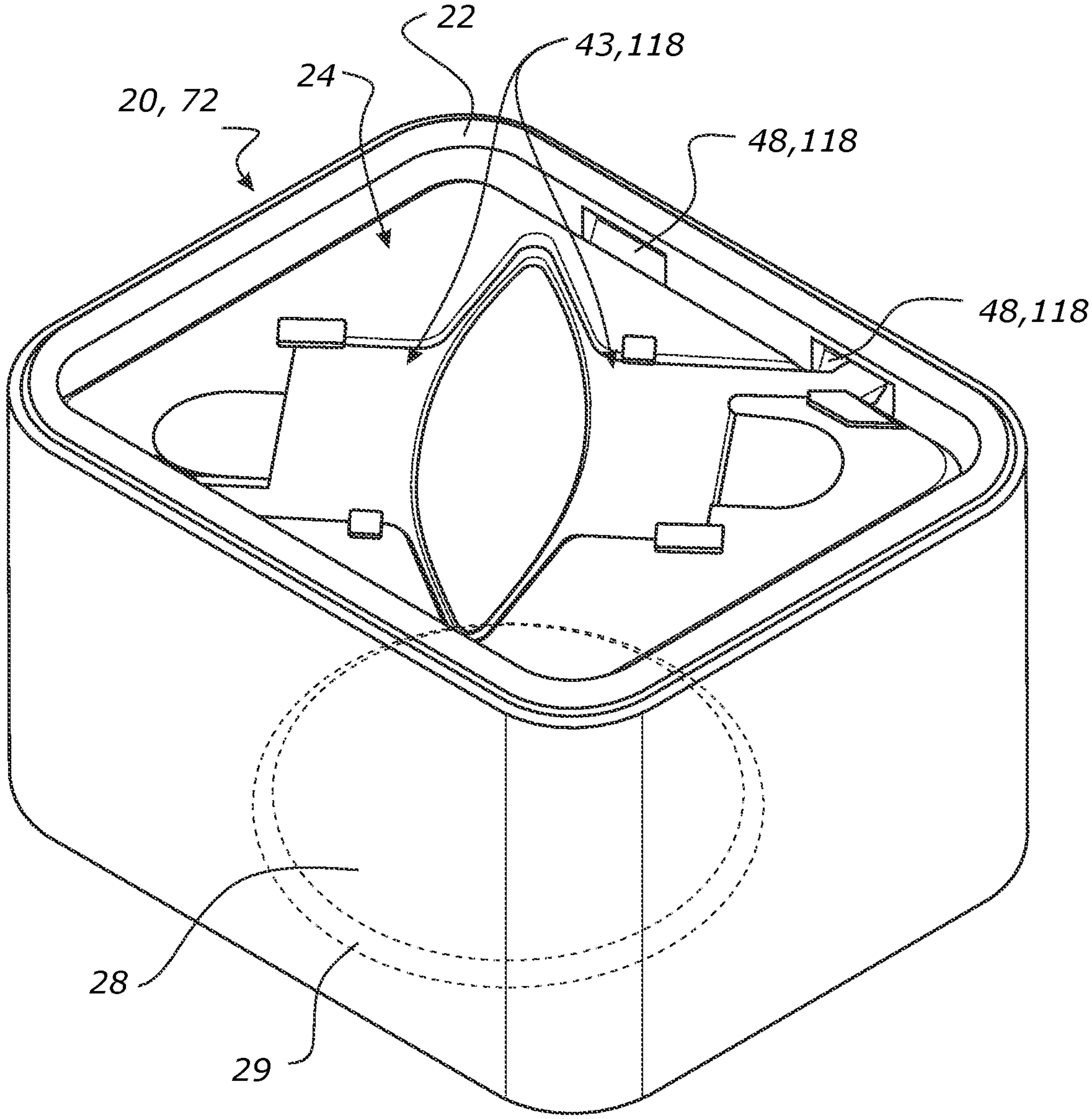
FIG. 3A is a perspective view of an apparatus according to the preferred embodiment including a humidification chamber and a compartment that receives the humidification chamber, in which a coupling on the humidification chamber engages the compartment.
Figure 3B:
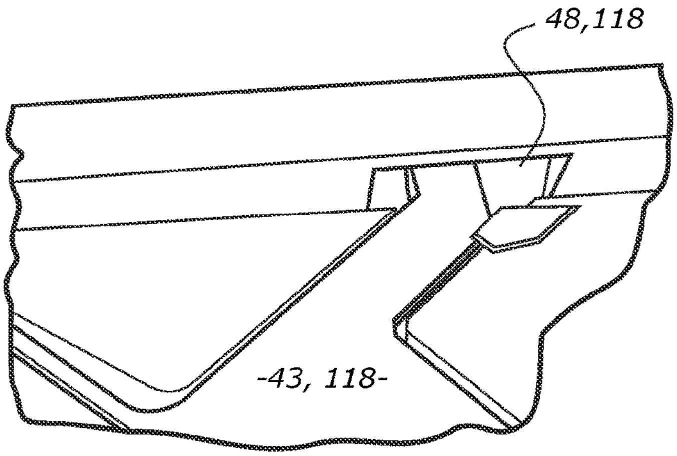
FIG. 3B is an enlarged view of part of the coupling which includes a latch engaging a recess in the compartment.
Figure 3C:
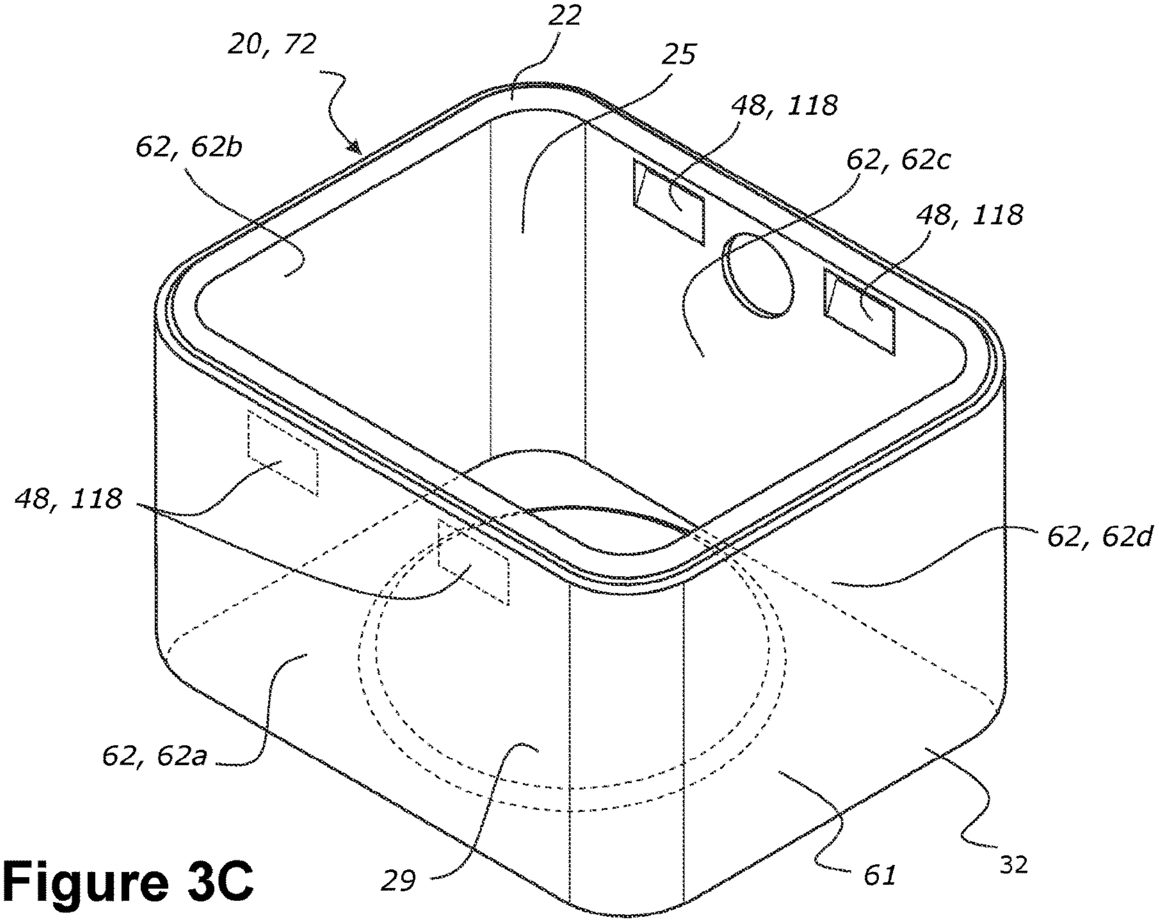
FIG. 3C is a perspective view of a compartment.

With reference to FIG. 3C the compartment 22 comprises a compartment body 32 and the heater plate 29. Optionally, the compartment 22 may have a lid (not shown in FIGS. 3A to 3L) that covers an opening 72 of the compartment 22. If provided, the lid would not be required to press against the humidification chamber 24 as the coupling 118 is operable to provide a holding force between the heater plate 29 and the heater base 28. The compartment 22 has a receptacle 25 defined by side wall 62 of the compartment 22 that receives the humidification chamber 24. For example, the side wall 62 may include for components, namely: a front compartment wall 62*a*, a left compartment wall 62*b*, the rear compartment wall 62*c*, and the right compartment wall 62*d*. Additionally, the receptacle 25 may also be defined by a base wall 61. The heater plate 29 can be considered to form part of the compartment base wall 61 or it can be separate from it. In this embodiment, there is a top opening 72 in the compartment 22 that allows the humidification chamber 24 to be inserted into the receptacle 25. The compartment 22 comprises at least one recess 48 that is configured to receive a portion of the latch 43, which will be described in more detail in the next section with reference to FIG. 3C. The latch 43 is received in a direction transverse to the direction that the humidification chamber 24 moves when inserted into the compartment body 32. This motion may also be transverse to the thermal engagement forces between the heater plate 29 and the heater base 28.

The compartment body 22 comprises at least one recess 48 that is configured to receive a portion of the latch 43. The compartment body 32 may have four recess 48 for instance. The recesses 48 are located on upper regions of the side wall 62 of the compartment 22. The recesses 48 are located on opposing compartment walls, such as a front wall 62*a* and the rear wall 62*c*, or the left wall 62*b* and right wall 62*d*, for example. Some embodiments may have four recess 48, in which both the front 62*a* and rear 62*c* compartment walls each have two recess 48 symmetrically spaced from each other—this helps with balancing the pressure exerted by the latch 43. Optionally, the latch 43 and actuator 39 could be configured to allow for left-handed actuation, or configured for right-handed actuation or configured for both. The recesses 48 are located on opposing corners, such as at the front left corner (corner of front wall 62*a* and left wall 62*b*), and rear right corner (corner of rear wall 62*c* and right wall 62*d*). The recess 48 may feature a sloped surface (decreasing depth from the top to the bottom of the recess) forming an undercut. The recesses 48 having an undercut as opposed to a rectangular pocket allows water residue and dirt build-up to run off easily, making it easier for self-cleaning.

The heater plate 29 comprises a thermal plate member attached to the base wall 61 of the compartment 22. Optionally, the heater plate 29 is connected to the base wall 61 via a biasing member, such as a resilient silicon ring. Other springs or alternative biasing mechanisms can be provided in addition or alternatively. When the biasing member is provided, the heater plate 29 is biased upwards in its natural state, such that when a humidifier chamber 22 is inserted and pushed down onto the heater plate 29, the biasing member will be compressed/forced downwards, but provide a biasing reaction force upwards against the downwards force. When engaged, the coupling 118 holds the heater base 28 in contact with the heater plate 29 at the holding force that may at least in part be exerted by the biasing. When there is no biasing member, the user will be required to press down in the humidification compartment 22 to align the latch 43 with the recess 48, and the coupling 118 is then active for pressing the heater plate 29 against the heater base 28 at a pressing force.

In another example, the heater plate 29 is in a fixed position within the compartment 22 (that is, the heater plate 29 does not include a biasing mechanism), and the force exerted by biasing is provided via another mechanism. For example, the humidification chamber 24 may include a lid and base with a flexible seal located therebetween. When the humidification chamber 24 is inserted into the compartment 22 the flexible seal is compressed via a downward force supplied by a user, and remains in a compressed state providing a (biasing) force when the latch(es) is engaged with the recess(es).

In another example, the force exerted by biasing may be provided by more than one component, for example the heater plate 29 and a flexible seal in the humidification chamber may both provide a (biasing) force.

The biasing can be any suitable mechanism that can be preloaded with compression or alternatively tension.

As can be seen in FIG. 3E, the underside 31 of the slidable latching member 45 may have a chamfered underside 145 so that when the humidification chamber 24 is pushed into the compartment 22, a downwards force is applied onto the tapered portion of the sliding member 45 leading to a retraction of the sliding member 45 as the spring 50 bends, see the arrows in FIG. 3E. The chamfered underside 145 therefore allows for a smoother transition between the unlocked position and locked operating position of the humidification chamber 24 (i.e. less force required to push the humidification chamber in). Without the chamfered underside 145, if the humidification chamber 24 is pushed into the compartment 22, retraction of the sliding members 45 may not occur, and may instead bend (or even break).

Figure 3F:
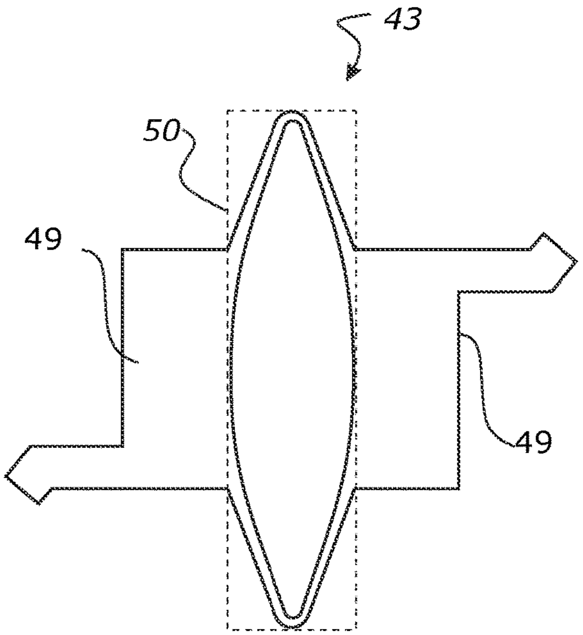
FIGS. 3F to 3J are schematic illustrations of alternative variations of a latch.
Figure 3G:
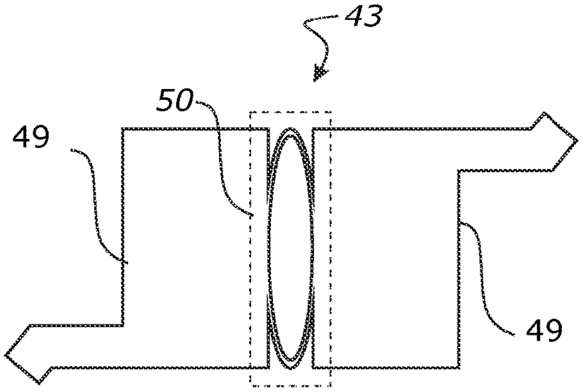
Figure 3H:
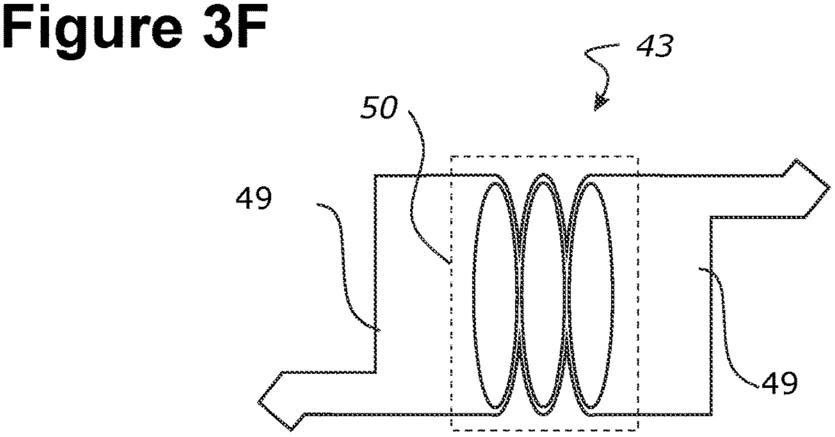
Figure 3I:
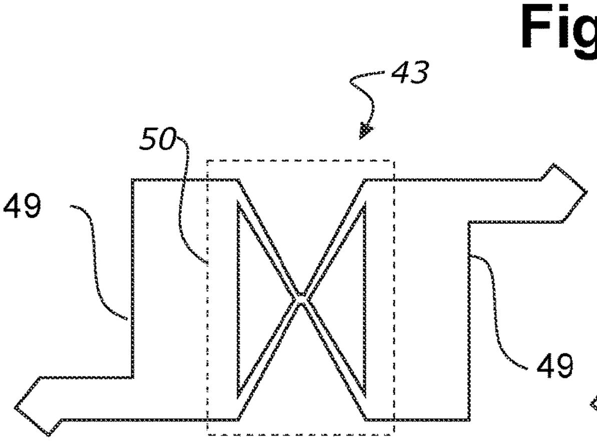
Figure 3J:
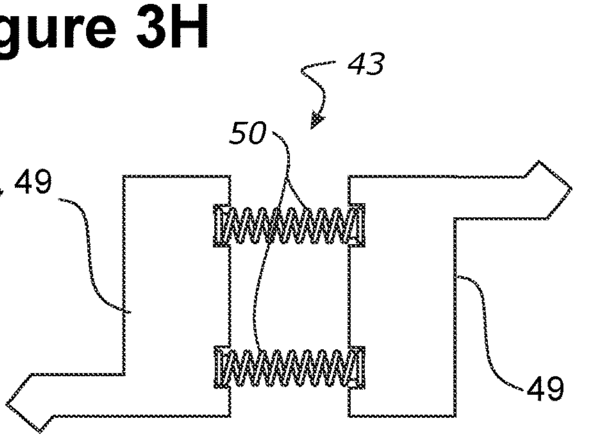
Figure 3K:
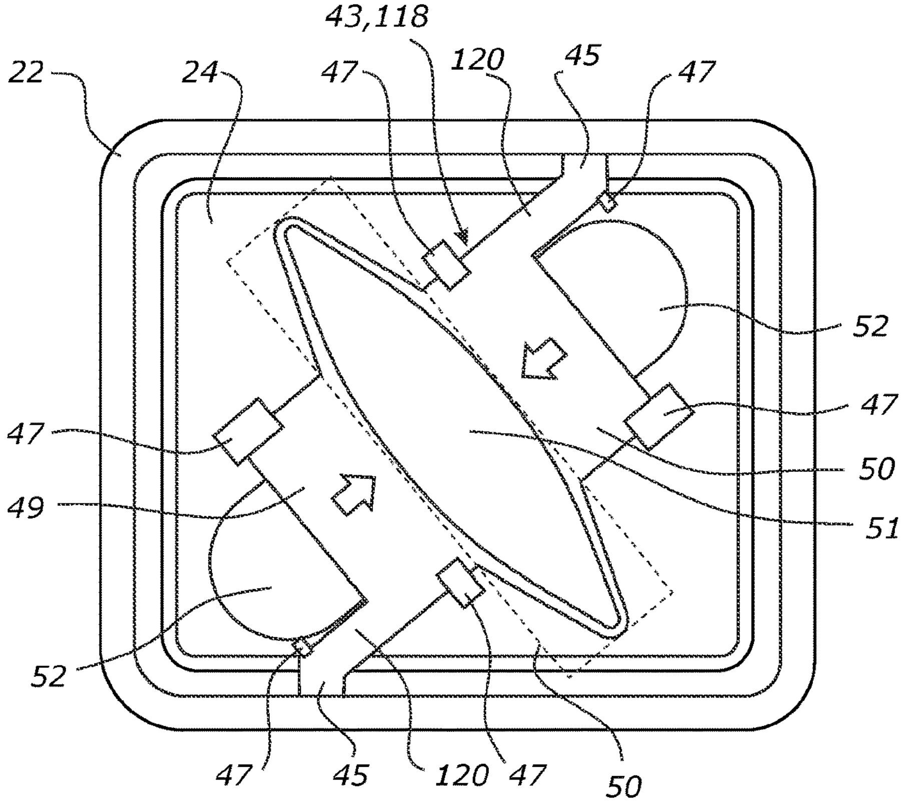
FIG. 3K is a plan view of the apparatus comprising the latch shown in FIG. 3F, in which the latch is in an inactive position.
Figure 3L:
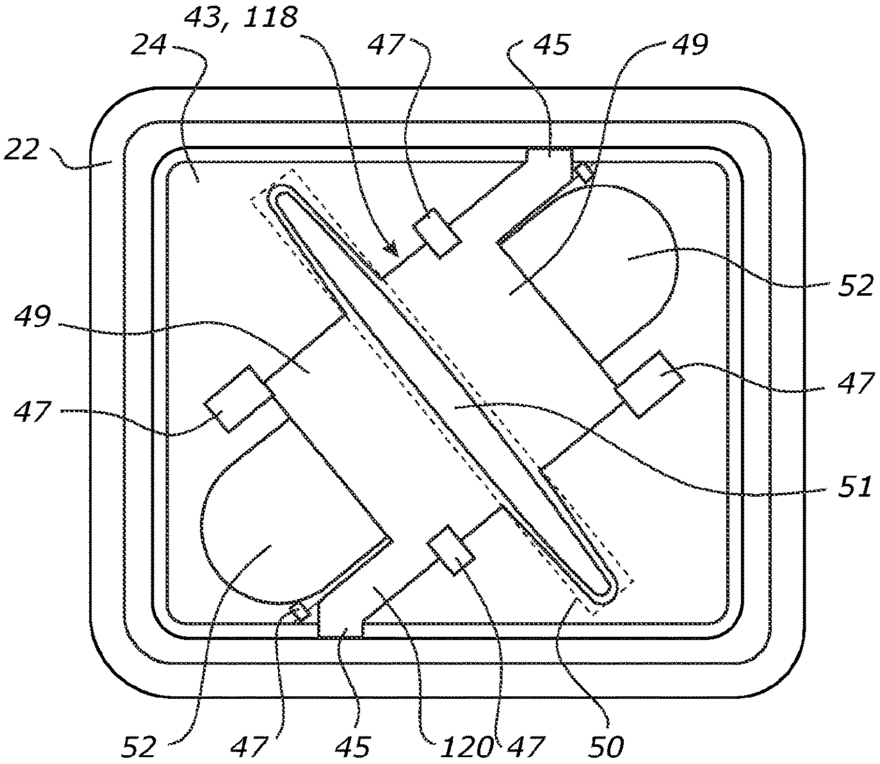
FIG. 3L is a plan view of the apparatus comprising the latch shown in FIG. 3F, in which the latch is in an energized configuration.

FIG. 3K shows the latch 43 in its rest configuration. In its rest configuration the slidable latching members 45 extend over the edge of the top surface of the humidification chamber 24. If the humidification chamber 24 is already inserted into the compartment 22, the slidable latching members 45 move transversely and are received by their respective recess 48 of the coupling 118. For example, recess 48 on the front compartment wall 62*a* receives a first slidable latching member 45, and a recess 48 on the opposing back compartment wall 62*c* receives a second slidable latching member 45. When the slidable latching member 45 is received transversely by the recess 48, a holding force is generated for facilitating thermal engagement of the heater base 28 and heater plate 29. The actuator 39 may be manipulated to transition the latch 43 from its rest configuration to its energized configuration as shown in FIG. 3L. The two finger tabs 49 of the actuator 39 for operating two respective slidable latching members 45 may be pinched in tandem (as shown by the arrows pointing inwards) to transition the latch 43 from its rest configuration to its energized configuration.

FIG. 3L shows the latch 43 in its energized configuration. The latch 43 is in its energized configuration when the slidable latching members 45 are retracted transversely from extending outwards. When the latch 43 is in its energized configuration, the humidification chamber 24 can be inserted to the compartment 22. Likewise, when the latch 43 is in its energized configuration, the humidification chamber 24 can be removed from the compartment 22. In the energized configuration the biasing spring 50 is pre-loaded by absorbing energy from the manipulation of the finger tabs 49. The spring 50 is pre-loaded by compression of the spring 50. When this happens, the spring 50 has spring potential energy and is said to be energized. If the actuators 39 are released, the pre-loaded spring 50 releases its spring potential. This causes the slidable latching members 45 to extend outwards so that the latch 43 transitions back to its rest configuration as shown in FIG. 3K.

The embodiment shown in FIGS. 3K and 3L show a single latch 43, the latch 43 comprising two slidable latching members 45, and each slidable latching member 45 is operated by a single biasing spring 50. The two latches 43 are operated in tandem by pinching the finger tabs 49 in the direction of arrows in FIG. 3K. In an alternative embodiment, the two latching members 45 may be operated independently of the other. That is to say, each latch 43 could have a single slidable latching member 45 that can be operated on independently with a single actuator 39.

FIGS. 3F to 3J illustrate five latches 43 having different forms of biasing springs 50. FIGS. 3F and 3G are examples of a single biasing spring 50. In particular, FIG. 3F illustrates a spring 50 that extends outside the finger tabs 49 and has legs joined at a mid-section. The spring 50 is ideally integrally formed with the finger tabs 49. FIG. 3G illustrates a spring 50 having a single loop that is arranged between, and integrally formed with, the finger tabs 49. The loop has an opened central region. The spring 50 shown in FIG. 3H is similar to the spring in FIG. 3G and comprises three open loops arranged side-by-side and are integrally formed with the finger tabs 49. FIG. 3I illustrates a spring 50 having legs arranged in an X-shape that interconnects, and is suitably integrally formed with, the finger tabs 49. Suitably, the legs can be flexed when the finger tabs 49 a squeezed toward each other. FIG. 3J illustrates a spring 50 comprising a pair of biasing springs and would compress in the usual manner.

The embodiment shown in FIG. 3C shows a compartment 22 comprising a receptacle 25 defined by a side wall 62 and a base wall 61. The cross section of the receptacle 25 is rectangular. However, in an alternative embodiment, the cross section of the receptacle 25 could be any other shape.

For instance, the receptacle 25 could have a circular horizontal cross-section defined by a single compartment wall and a compartment base.

The embodiments shown in FIGS. 3C, 3K and 3L depict a many-to-many relationship between the slidable latching member 45 and the coupling opening 131—the humidification chamber 24 and latch 43 are rotationally symmetrical, and the humidification chamber 24 can be rotated so that the two slidable latching members 45 can each slidingly engage with two coupling openings 131, each coupling opening 131 located on opposing compartment walls 62*a*, 62*c*. In other embodiments, there could instead be a one-to-one relationship—for example, the humidification chamber and compartment cavity could instead be asymmetrical to prevent rotation; if the latch has a single slidable latching member, it can only engage with a particular corresponding coupling opening. A one-to-one relationship would be preferable if the humidification chamber had an inlet and outlet that were not interchangeable, for example if the inlet and outlet and corresponding ports on the compartment were not located in rotationally symmetrical locations. The one-to-one relationship of the latching mechanism could prevent the chamber from being inserted into the compartment unless the chamber were in the correct orientation. In other embodiments, there could instead be a many-to-one relationship—for example, the compartment may have a single coupling opening big enough to receive two or more slidable latching members. In other embodiments, there could instead be a one-to-many relationship—for example, the latch may have a single slidable latching member but can slidingly engage with two or more coupling openings.

The embodiment shown in FIG. 3A shows a compartment 22 receiving a humidification chamber 24 vertically. However in an alternative embodiment, the compartment 22 may be designed so that it is configured to receive a humidification chamber 24 laterally.

FIGS. 4A to 4G illustrate an apparatus 20 that includes a humidification chamber 24 having a water tub 56 with a heater base 28 in which water 26 is evaporated into a gas stream 34, and a compartment 22 having a compartment body 32 with an opening 72 that receives the humidification chamber 24. The compartment 22 has a side wall 62 and a base wall 61 having a heater plate 29 on which the heater base 28 of the humidification chamber 24 is seated. The compartment 22 may have an optional biasing arrangement which mounts the heater plate 29 to the base wall 61 of the compartment 22.

The apparatus 20 also has a coupling 118 that maintains the humidification chamber 24 in an operating position in the compartment body 32 and is operable to hold the heater base 28 against the heater plate 29 at a holding force which promotes thermal engagement therebetween. The coupling 118 is incorporated in a tub cover 57 that is fitted to the water tub 56. In other embodiments, not illustrated in the Figures, it is possible that the coupling 118 could be incorporated in a support that presses against the humidification chamber 24 when in the active position.

The gas stream 34 to be humidified may enter directly into the water tub 56 in accordance with FIG. 1A. Alternatively, it is also possible that the gas stream 34 may enter the humidification compartment 22 before entering the humidification chamber 24 in accordance with FIG. 1B. In any event, the apparatus 20 may also include a lid (not illustrated in FIGS. 4A to 4H) for covering the opening 72 to the compartment 22 which would be fitted to the humidification compartment 22 when the apparatus 20 when operated in accordance with the arrangement in FIG. 1B. However, on account of the operation of the coupling 118, there is no requirement for the lid to apply any downward pressure on to the humidification chamber 24 to facilitate good thermal engagement between the heater base 28 against the heater plate 29.

Figure 4B:
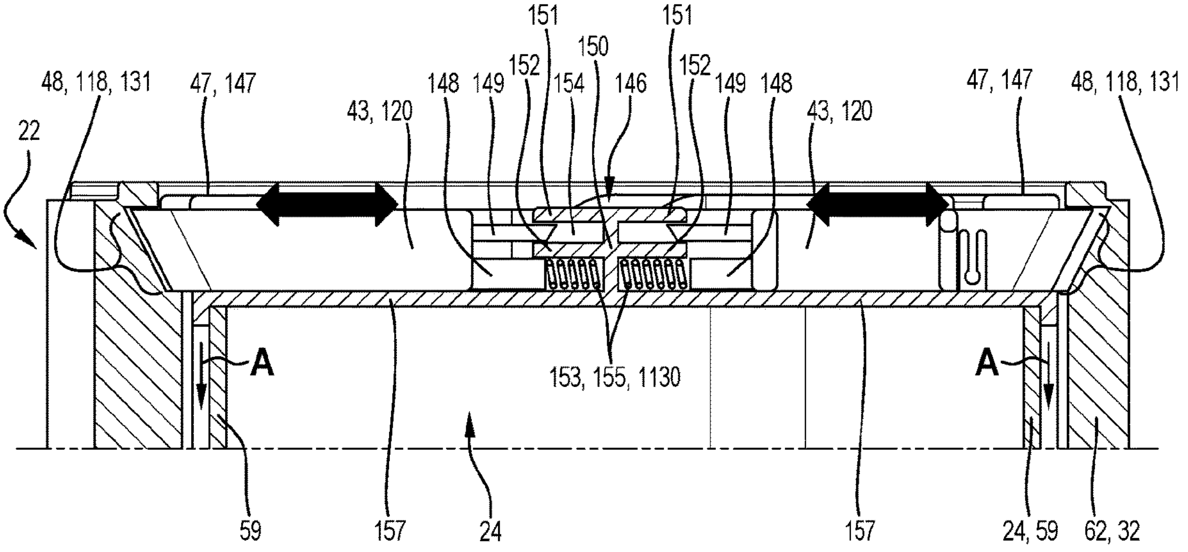
FIG. 4B is a cross-sectional view of an upper portion of the apparatus along the line B-B shown in FIG. 4A.
Figure 4C:
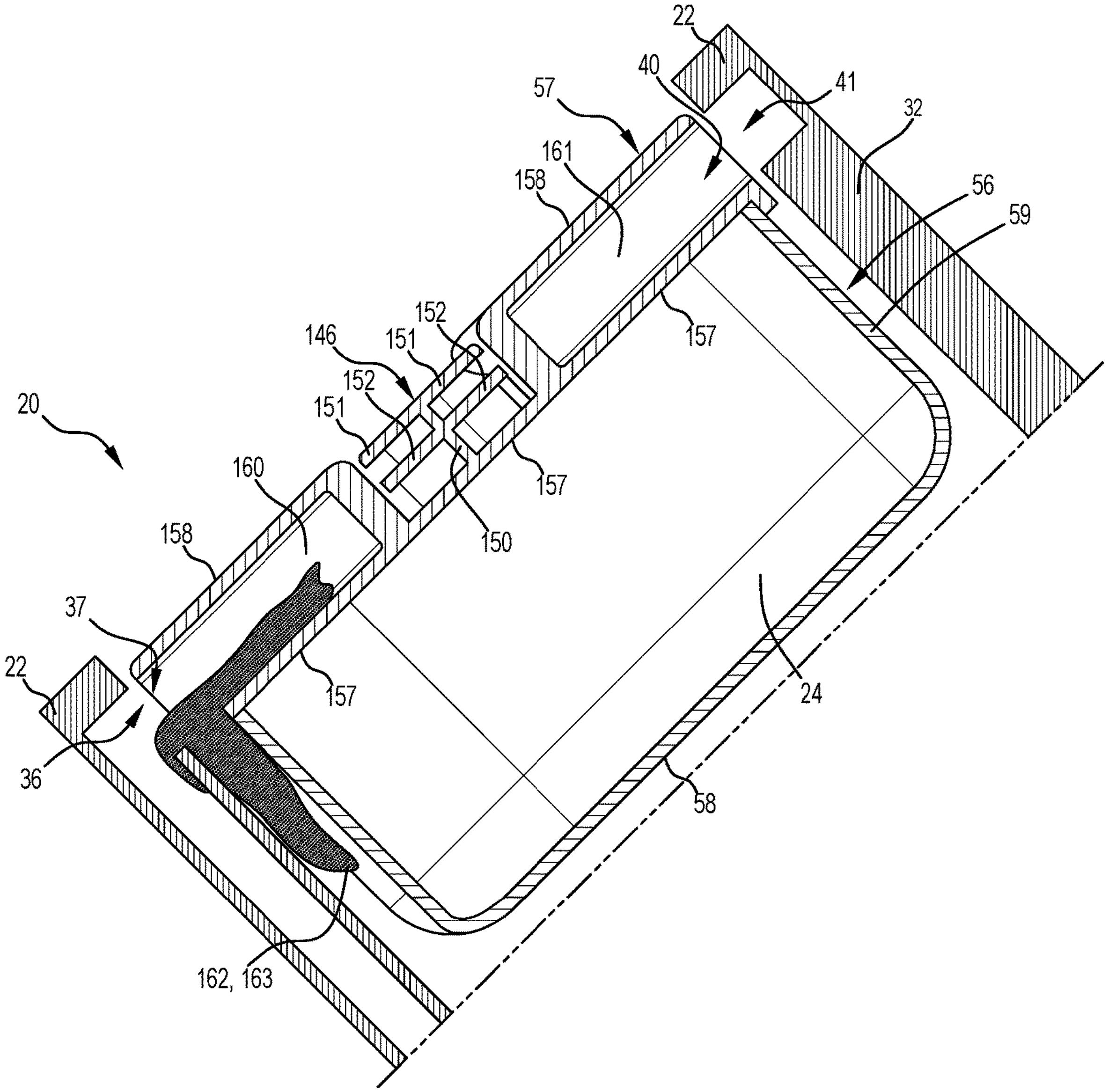
FIG. 4C is a cross-sectional view of the apparatus along the line A-A in FIG. 4A, in which the apparatus is illustrated as tilting forward and spillage of water is substantially contained between the humidification chamber and the compartment.
Figure 4D:
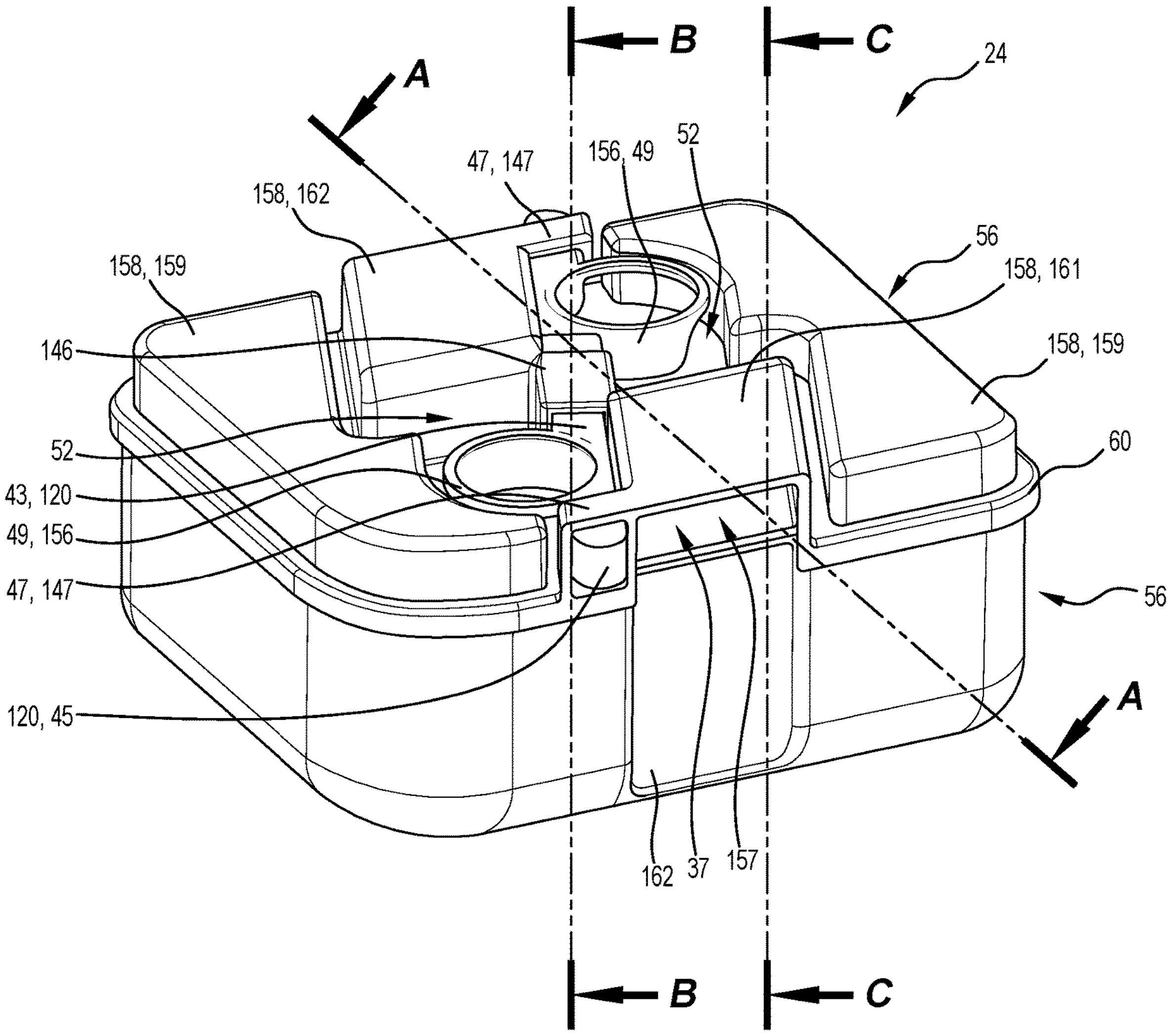
FIG. 4D is a top, front and side perspective view of the humidification chamber shown in FIG. 4A, in which the coupling has shafts for engaging the compartment.

The coupling 118 includes a latch 43 having a pair of shafts 120 having latching members 45 at the outer ends of the shafts 120 that reciprocate in and out and can be operated independently or in unison along an axis, represented by the line B-B in FIGS. 4A and 4D. The couplings 118 also include recesses 48 in the form of coupling openings 131 that receive the shafts 120. FIG. 4B is a cross-sectional view along the line B-B on which the shafts 120 reciprocate. Humidification chamber 24 also has a retention member 47 for the latch 43 including shafts 120, in which the inner ends of the shafts 120 are housed in a central hub 146 and guide sleeves 147 toward the perimeter of the tub cover 57. The inner ends of the shafts 120 include a lower limb 148 and an upper limb 149 that are housed and slide within the central hub 146. As can be seen in FIG. 4B, the central hub 146 includes a middle divider 150 that extends upwardly and a first web 151 and a second web 152 extend outwardly from the middle divider 150 that define a lower slot 153 and upper slot 154 respectively on either side of the middle divider 150. The lower and upper slots 153, 154 receive the lower end upper limbs 148, 149 of the shafts 120 respectively to assist in guiding sliding motion of the shafts 120. The lower slot 153 houses a first biasing member 155 which includes a compression spring 1130 that biases the shafts 120 into an outer position and extend outwardly from the outer periphery of the tub cover 57 of the chamber 24. The upper slots 154 and upper limbs assist in guiding the shafts along the axis B-B.

Each of the shafts 120 also have finger tabs 49 in the form of finger rings 156 extending laterally on opposite sides of the shafts 120 and are spaced on either side of the central hub 146. The finger rings 156 are arranged in an outwardly facing depression 52 in the tub cover 57 which can be seen in FIGS. 4A, 4D and 4E. The depression 52 is formed by an inner top wall 157 of the tub cover 57 and side sections extending from the inner top wall 157 to an outer top wall 158 which form inwardly facing air cavities 159.

The air cavities 159 are positioned on left and right flanks of the tub cover 57 and are formed by a section of an outer top wall 158 extending from an inner top wall 157 of the tub cover 57.

Movement of the shafts 120 in an outward direction along the axis B-B can be limited by the finger rings 156 engaging and being stopped by the outer top wall 158 of the air cavities 159 and/or the guide sleeves 147.

The tub cover 57 also comprises a first passageway 160 that extends from the chamber inlet 37 to a first central opening 37A via which the gas stream 34 enters the water tub 56. The tub cover 57 also comprises a second passageway 161 that extends outwardly from a second central opening 40A through which humidified gas enters to the chamber outlet 40. As can best be seen in FIGS. 4C and 4H, the first and second passageways 160, 161 are formed between sections of the inner top wall 157 and the outer top wall 158.

Figure 4E:
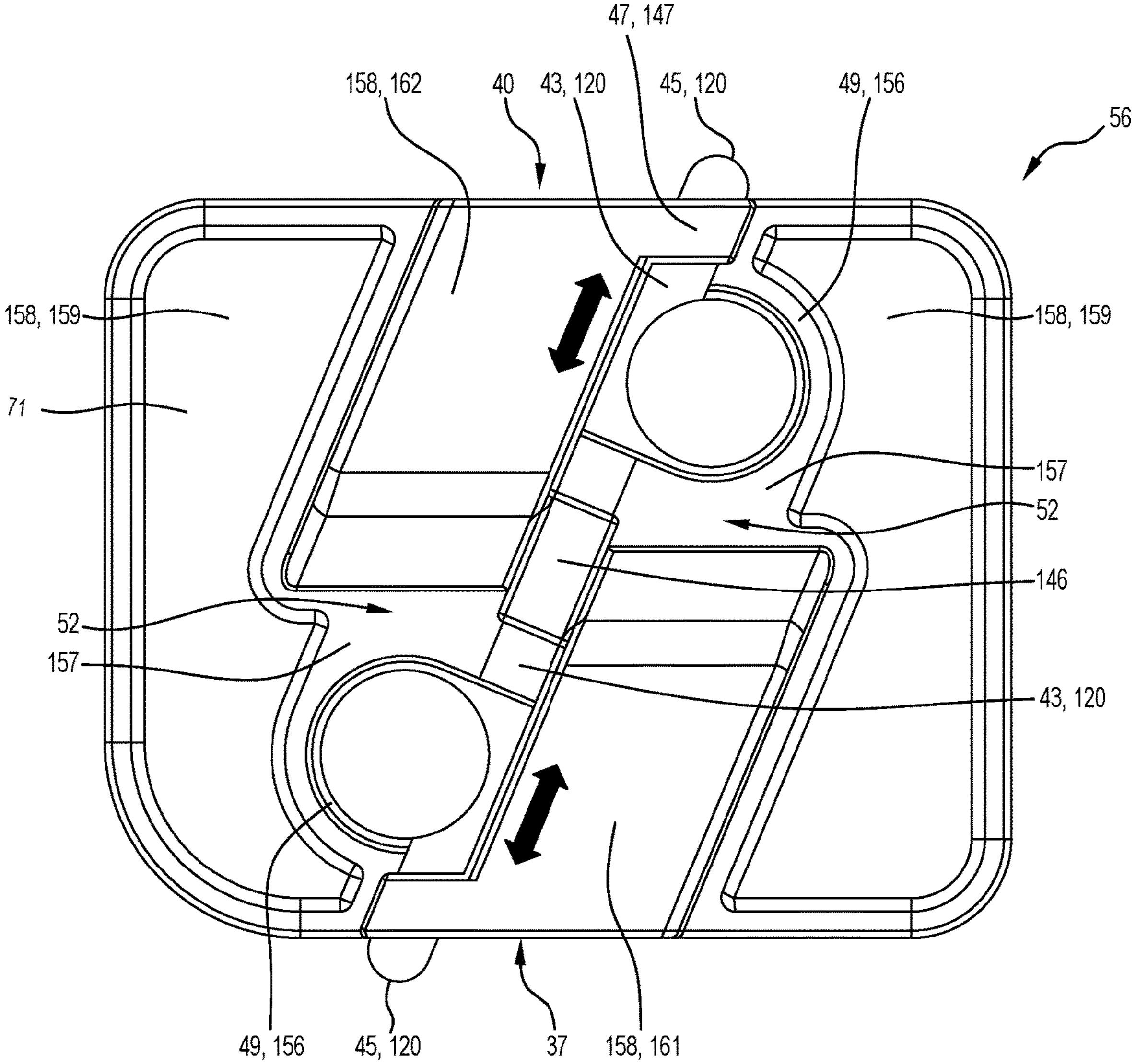
FIG. 4E is a top view of the humidification chamber shown in FIG. 4D, in which the arrows indicate the direction of movement of the shafts of the coupling.
Figure 4F:
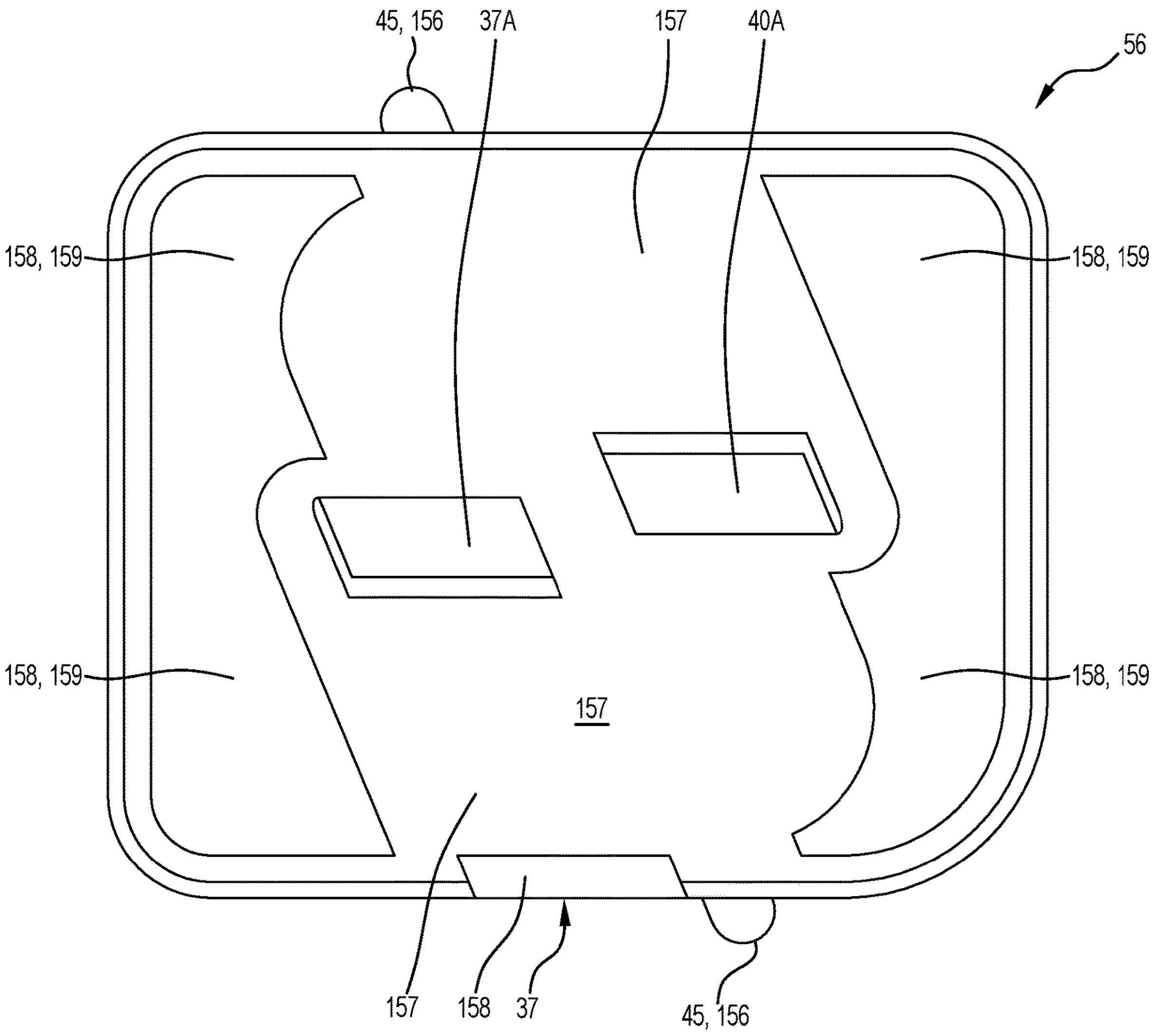
FIG. 4F is an underneath view of a top wall of the humidification chamber shown in FIG. 4A.

As can best be seen in FIGS. 4A, 4D and 4E, the finger rings 156 are spaced apart so that a user can insert a thumb into one finger ring 156 and a finger of the same hand into the finger ring 156. The user can then squeeze the finger rings 156 toward each other in the direction of arrows pointing toward each other, see FIGS. 4B and 4E, to move the shafts 120 into an inactive position. When a user has stopped squeezing the finger rings 156 or simply removes their fingers, the compression springs 1130 move the shafts 120 from the inactive position to an active position in the outward direction of the arrows in FIGS. 4B and 4E.

As can best be seen in FIG. 4A, the side walls 62 of the compartment 22 have recesses 48 which form part of the coupling 118 and which receive the shafts 120 when in the active position. Moreover, the shafts 120 extend laterally out from the tub cover 56 in the active position and the shafts 120 are arranged to transfer forces between the humidification chamber 24 to the compartment body 32. The forces transferred can include reaction forces that are attributable to the holding force between the heater base 28 of the humidification chamber 24 and the header plate 29 of the humidification compartment 22.

The term "laterally" in the paragraph immediately above refers to a direction normal to of the inner faces of the side walls 62 of the compartment 22.

Figure 4G:
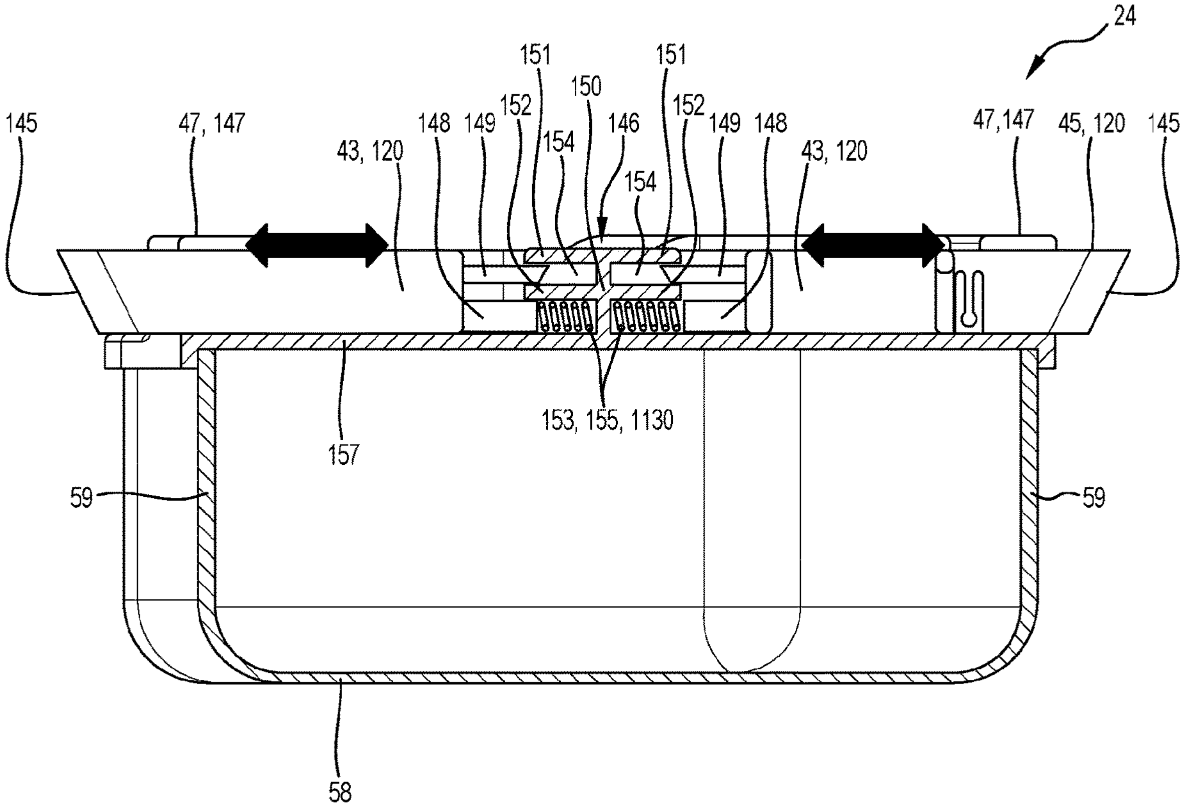
FIG. 4G is a cross-sectional view of the humidification chamber along the line B-B in FIG. 4D, in which the arrows indicate the direction of movement of the shafts of the coupling.

As can be seen in FIGS. 4B and 4G, the latching members 45 form the outer ends of the shafts 120 and have chamfered surfaces on the underside 145 of the latching member 45, which allows a user to manually insert and push the humidification chamber 24 into the compartment 22 while the chamfered surfaces of the shafts 120 engage the interior surface of the side walls 62 of the compartment 22 and move inwardly against the compression springs 1130 until the outer ends of the shafts 120 are received by the recesses 48 of the side walls 62 of the compartment 22. When the humidification chamber 24 approaches its operating position within the compartment 22, the heater base 28 will engage the heater plate 29 and in order for the outer ends of the shafts 120 to be fully received by the recesses 48 in the active position, the user will be required to apply a downward force onto the humidification chamber 24, thereby applying a holding force between the heater base 28 and the heater plate 29 which is then maintained by the shafts 120 of the couplings 118 engaging the recess 48 (or coupling openings 131) when the user stops pressing on the humidification chamber 24.

In order to remove the humidification chamber 24, a user can place their thumb and a finger of one hand into the finger rings 156 and a squeeze the thumb and second finger toward each other, until the outer ends of the shafts 120 are clear of the recesses 48, thereby moving the coupling 118 into an inactive position. The user can then lift the humidification chamber 24 clear of the apparatus 20.

Figure 4H:
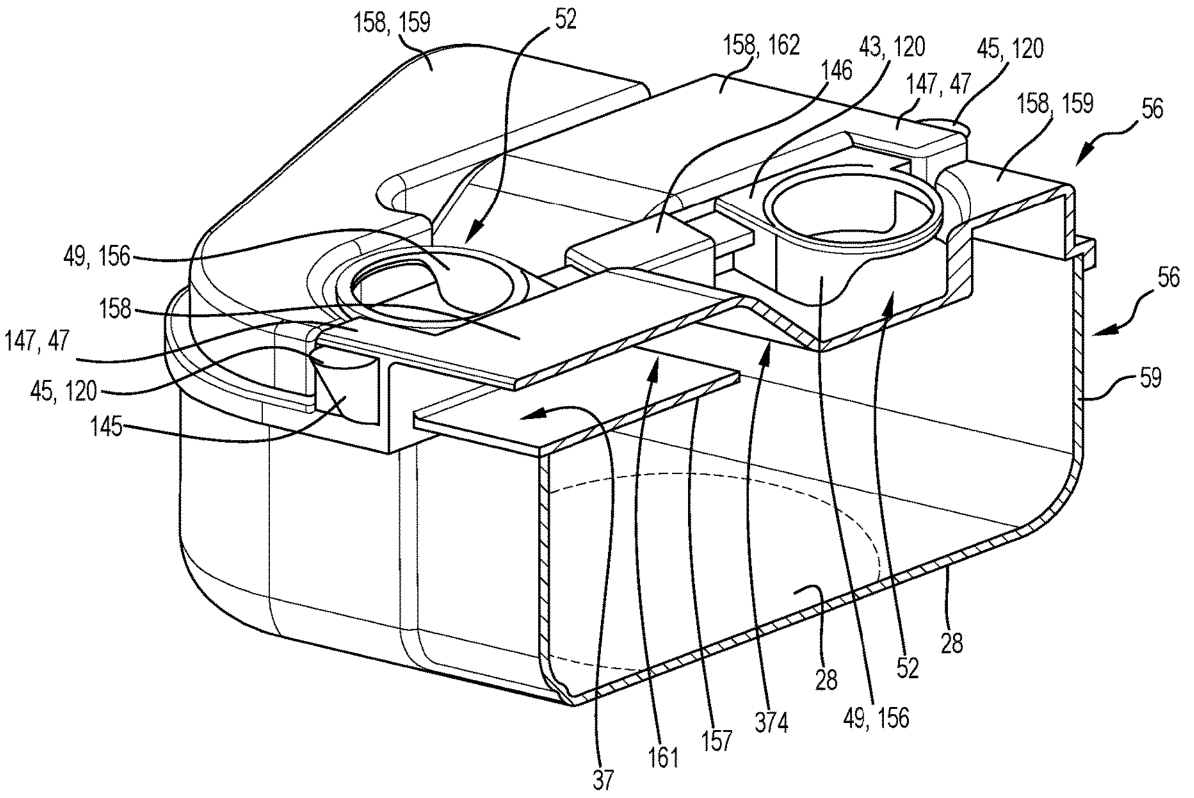
FIG. 4H is a cross-sectional perspective view of the humidification chamber through the line C-C in FIG. 4D.

As can be seen in FIGS. 4C, 4D and 4H, a lower portion of the chamber inlet 37 which forms part of the inner wall of the tub cover 57 is stepped inwardly from the outer perimeter of the water tub 56. In particular, the inner top wall 157 is stepped inwardly relative to the outer top wall 158 that forms part of the chamber inlet 37. In additional, a front aspect of a side wall 59 of the water tub 56 below the chamber inlet 37 has a channel 162 extending vertically over the height of the water tub 56. As can best be seen in FIG. 4C, the chamber inlet 37 and the channel 162 provide a spillway 163 that accommodates overflow of water out of the chamber inlet 37 in the event that the apparatus 20 is tilted with the front side of the apparatus 20 lower than the backside of the apparatus 20. The spillway 163 directs spillage from the humidification chamber 24 into the humidification compartment 22, thereby minimizing the risk of backflow into the electrical components of the apparatus 20 via the compartment outlet 36.

Although not shown in the Figures, the side wall 59 of the water tub 56 below the chamber outlet 40 may also have a channel and the chamber outlet 40 stepped inwardly in a similar manner to the chamber inlet 37.

The chamber outlet 40 forms a substantially gastight seal with the compartment inlet 41 when the humidification chamber 24 is in an operating position in the compartment 22, which in turn minimizes the leakage of the humidified gas stream 24 back into the compartment 22. Conversely, the chamber inlet 37 may be spaced from the compartment outlet 36, and in particular includes a spillway 163 as described above that is arranged to receive water spillage from the humidification chamber 24 in the event that the apparatus 20 is tilted forward, as shown in FIG. 4G.

Although not shown in the figures, the humidification chamber 24 will also include internal baffles to prevent short-circuiting of the gas stream between the central inlet and outlet of the tub cover 57.

As can best be seen in FIG. 4E, the humidification chamber 24 also has an asymmetric profile in which the front left corner has a larger radius of curvature compared to other three corners. The asymmetric profile ensures that the humidification chamber 24 can only be loaded in the compartment 22 with the chamber inlet 37 facing the compartment outlet 36, and similarly the chamber outlet 40 facing the compartment inlet 41.

Although not shown in the figures, it is within the scope of this embodiment that the apparatus 20 may have a support on which the coupling 118 is mounted and the support forms part of the humidification chamber 24 to maintain the humidification chamber 24 in the compartment 22. That is it say, the coupling 118 need not form a direct component of the tub cover 57 as shown in FIGS. 4A to 4H.

It is also within the scope of this embodiment that the apparatus 20 includes a support to which the coupling 118 is mounted and that the support bears directly or indirectly against the humidification chamber 24 to maintain the humidification chamber 24 in position in the compartment 22 and hold the heater base 28 to the heater plate 29 at a holding force. In this example, the support may be mechanically connected to the humidification chamber 24 such that a user can remove the humidification chamber 24 from the compartment 22 when the coupling 118 is inactive.

According to the preferred embodiment illustrated in FIGS. 4A to 4H, the support is in the form of a lid 71 of the humidification chamber 24. The coupling 118 is mounted to the lid 71 by being incorporated in the structure of the lid 71. In addition, as mentioned above, another lid, not shown in the Figures, can be positioned over the opening 72 of the compartment 22.

To facilitate cleaning and refilling with water, the tub cover 57 may be either completely separable from the water tub 56, or pivotally connected to the water tub 56 by a hinge mechanism (not shown in the figures). The hinge mechanism, if present, may be arranged along one side of the humidification chamber 24. In the case of the preferred embodiment, the tub cover 57 can be separated from the water tub 56 and a pull tab (not shown in figures) may be provided on the tub cover 57. When the tub cover 57 is closed onto the water tub 56, a watertight seal is formed about the opening of the water tub 56. The watertight seal maybe formed by either one or a combination of the water tub 56 and the water cover 57 having a flange that is press fit into a channel. For example, the watertight seal may be provided by any suitable sealing members, that may for example, include a compressible silicon or rubber about an opening of a channel that receives a less flexible flange.

FIGS. 5A to 5D—Embodiment Having a Holder for Applying a Pressing Force to the Humidification Chamber FIGS. 5A to 5D illustrate an apparatus 20 including a compartment 22 having a heater plate 29 and a compartment body 32 that receives a humidification chamber 24. The apparatus 20 also includes a holder 53 that presses against a humidification chamber 24, in the direction of arrow "A" (see FIG. 5C) so that the heater base 28 (see FIG. 5B) is held to the heater plate 29 to enhance thermal engagement therebetween.

The compartment body 32 of the humidification compartment 22 has a base wall 61 and a side wall 62 defining an upwardly facing opening 72. The side wall 62 has a front panel that may, for example, have user controls, a rear panel, and opposite side panels.

The humidification chamber 24 has a water tub 56 which receives an amount of water 26 which is used to humidify the gas stream 34 passing through the humidification chamber 24, and a water tub cover 57 which can be fitted to the water tub 56. The water tub 56 includes a bottom wall 58 and a side wall 59 extending from the bottom wall 58, and the side wall 59 defines an open top of the water tub 56. The heater base 28 may form part of the bottom wall 58 and the side wall 59 may also include a lip or flange that extends about the open top.

The water tub cover 57 can be removed from the water tub 56 to facilitate cleaning the inside of the water tub 56. The water tub cover 57 may have a single integrally formed structure, or alternatively the water tub cover 57 may include two or more separable elements. For example, the water tub cover 57 may include outer and inner layers 57A and 57B respectively that are separable or joined together.

Figure 5A:
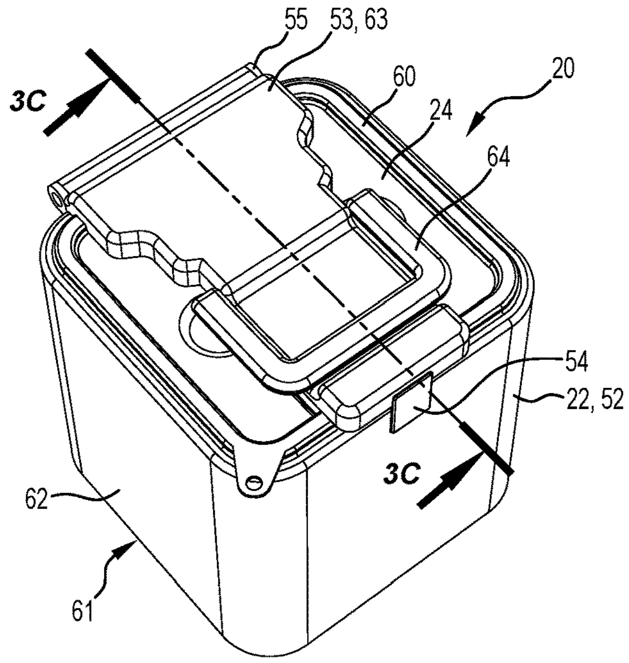
FIGS. 5A and 5B are schematic perspective views of an apparatus having a holder located in an operative position for applying a holding force to the humidification chamber, and an inoperative position, respectively.
Figure 5B:
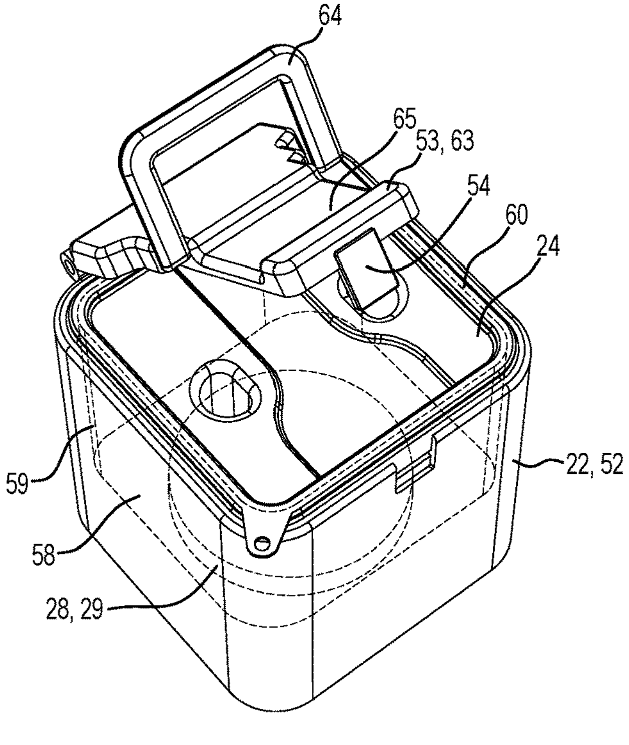
Figure 5C:
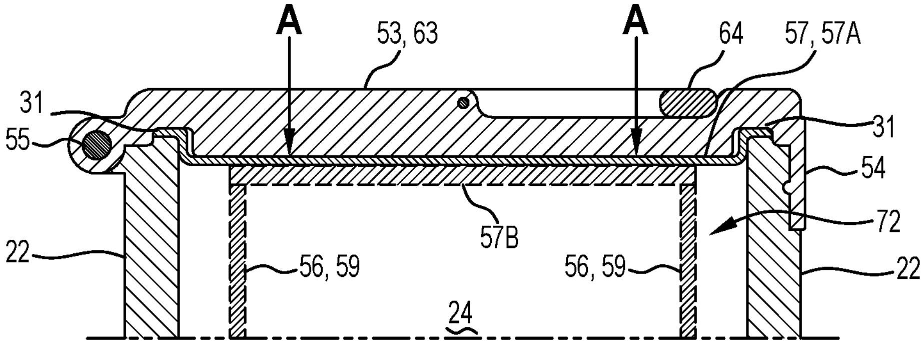
FIG. 5C is cross-sectional views of the apparatus as identified by the arrows in FIG. 5A.

FIG. 5C is an example in which the water tub cover 57 is sealed against the opening 72 of the compartment 22 by a seal 31. The opening 72 of the compartment 22 may be defined by an upper horizontal surface as shown in the figures, or by an inclined surface. The sealing 31 can be provided about the perimeter of the water tub cover 57 and/or the opening of the compartment 22. The sealing 31 may be an O-ring attached to the water tub cover 57 and/or the horizontal surface of the compartment 22, or have an over-moulding structure. To achieve an adequate sealing between the water tub cover 57 and the compartment 22, the water tub cover 57 has sufficient structural rigidity to allow a downward force between the tub cover 57 and the horizontal surface of the compartment 22. The structural rigidity of the tub cover 57 may be provided in different regions or lines across the water tub cover 57, including about a peripheral region of the water tub cover 57. When the compartment 22 is sealed in this manner, the apparatus can be operated according to the apparatus depicted in FIGS. 1A and 1B depending on the manner in which the compartment outlet 36 and chamber inlet 37 (see FIGS. 1A and 1B) are arranged, and the manner in which chamber outlet 40 and the compartment inlet 41 (see FIGS. 1A and 1B) are arranged.

Figure 5D:
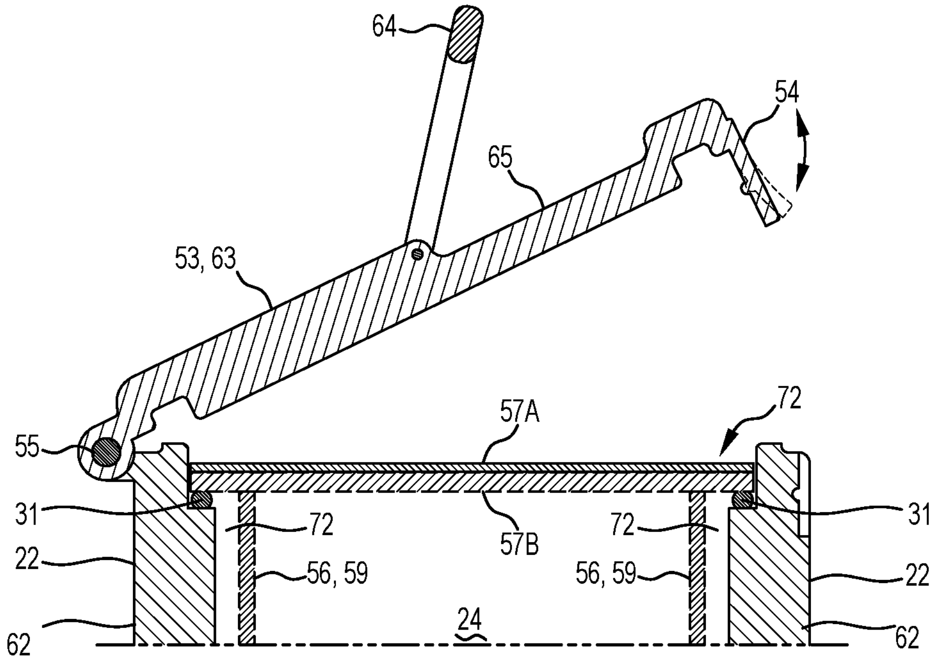
FIG. 5D is a schematic cross-sectional view of another embodiment that has the holder shown in FIGS. 5A and 5B. Features representing an inlet and an outlet of the humidification chamber have been omitted from FIGS. 5C and 5D.

FIG. 5D is an example in which the side wall 62 of the compartment 22 has stepped profile and the seal 31 is positioned on an upper horizontal surface of the stepped profile and/or on an underneath surface of the inner layer 57B of the water tub cover 57. In this example, the compartment 22 is sealed by the seal 31 being engaged. The water tub cover 57 is also positioned inside the opening 72 of the compartment 22. Depending on the manner in which the compartment outlet 36 and the chamber inlet 37 (see FIGS. 1A and 1B) are arranged, and the manner in which the chamber outlet 40 and the compartment inlet 41 (see FIGS. 1A and 1B) are arranged, the gas stream passing through the apparatus can flow according to the arrangement described with reference to FIGS. 1A and 1B.

In one example, the heater plate 29 may be fixed at a relatively stationary position to the base wall 61. In other words, the heater plate 29 may be fixed relative to the humidification compartment 22.

In another example, the heater plate 29 has a biasing arrangement and may be mounted on the base wall 61 or form part of the base wall 61. The biasing arrangement allows the heater plate 29 to move in response to the holding force applied to the humidification chamber 24. Ideally, the biasing arrangement allows a surface of the heater plate 29 to move away from the holder 53. The biasing arrangement may include any suitable biasing mechanism, such as one or more compression springs or a resiliently flexible skirt about the heater plate 29.

The holder 53 includes a strap 63 or belt that extends across the apparatus 20 and engages the compartment body 32 in at least two locations. Specifically, the strap has a rigid body that is connected on a pivot mounting 55 to a rear panel of the compartment 22 and is releasably attached to front wall of the compartment 22 by a latching device 54. The strap 63 can be pivoted forward to engage the latching device 54 in an operative position. In the operative position, an inner surface of the strap 63 engages and presses against the humidification chamber 24 in the direction of the arrow "A", see FIG. 5C. For example, the interface of the strap 63 may have formations that engage and co-operate with load points on the humidification chamber 24. The formations may, for example, align with and be configured to press against the peripheral rim 60 extending about the tub cover 57. The formations may include lugs or indentations. The formations may also include resiliently deformable materials, such as compression foam that assist in cushioning and distributing the pressing force of the holder onto the humidification chamber.

In addition, the humidification chamber 24, the inner surface of the strap 63, and the position of the heater plate 29 which is determined by the biasing arrangement are sized to accommodate the humidification chamber 24 between the heater plate 29 and the strap 63 when the strap 63 is located in the operative position. With the strap 63 in the operative position, the heater plate 29 may move at least to some extent on the biasing arrangement, which may in part generate a biasing force, which may equate, in magnitude, to part of the holding force "A" that holds the heater base 28 to the heater plate 29. Other factors such as when the biasing arrangement has compressed to a maximum, may allow the holding force to be greater than the biasing force of the biasing arrangement. In any event, the holding force will be a function of the degree to which the holder presses against the humidification chamber 24.

By releasing the latching device 54, the strap 63 is free to pivot and can stop applying the holding force to the humidification chamber. In addition, once the latching device 54 has been released, a user 42 can pivot the strap 63 away from the compartment 22 to allow the humidification chamber 24 to be removed from the compartment 22. This may be required for a number of reasons, including cleaning and servicing of the compartment 22 and the chamber 24. In one example, the pivot mounting 55 may be a hinge joint that non-detachably connects the strap 63 to the compartment 22.

In another example, the pivot mounting 55 described in the paragraph immediately above may be a hinge joint that releasably connects the strap 63 to the compartment 22.

In other examples not illustrated, the strap 63 may be releasably attached to the compartment body 32. For example, the strap 63 may be releasably attached by way of two latching devices provided at, or toward, opposite ends of the strap 63.

The strap 63 overlays only part of the humidification chamber 24. Specifically, as can best be seen in FIGS. 5A and 5B, the width of the strap 63 reduces from the back of the strap 63 that is pivotally mounted to the compartment 22, to the latching device 54 at the front of the strap 63. The width of the strap 63 at the rear panel of the compartment 22 extends across the width of the compartment 22, and in particular the width of the strap approximately equates to the width of the opening of the compartment 22, and reduces in width to cover approximately half the opening 72 of the compartment 22 at a central section, and further reduces in width at the front of the strap to approximately one third of the width of the compartment 22.

In other examples, not illustrated in the figures, the strap 63 may have other geometries, such as a constant width from the front to the back of the strap 63, an hour glass shape in which the strap 63 has a narrower width in a central section of the strap 63, or a bulb shape in which the strap 63 has an enlarged width in a central section compared to the ends of the strap 63.

In any event, the strap 63 does not close or seal the humidification compartment 22 when in the operative position because the strap 63 does not extend over and about the opening 72 of the humidification compartment 22. However, the humidification chamber 24 may be arranged to close the opening of the humidification compartment 22. For example, the humidification chamber 24 may close the opening of the compartment 22 when the chamber 24 is received by the compartment 22 without the strap 63 being located in the operative position. For example, as can be seen in FIG. 5C, the humidification chamber 24 and in particular the water tub cover 57 may be sized to protrude from the opening 72 of the humidification compartment 22 and either one or a combination of the following may close and seal the compartment 22:

i) the walls 59 of the water tub 56 may contact and seal against the wall 62 of the compartment 22, ii) the lip or rim 60 of the water tub 56 may contact and seal the walls 62 of the compartment 22, or the opening 72 of the compartment 22, or iii) the lid of the humidification chamber, such as a lip or rim 60 of the water cover 57 may engage the walls 62 or the opening 72 of the humidification compartment 22.

The lip or rim 60 of the humidification chamber 24 may be sized to extend about and beyond the opening 72 of the humidification compartment 22 to enclose the humidification compartment 22.

The contact between the humidification chamber 24 and the compartment 22 mentioned above in items i) to iii) may also only occur when the holder 53 is located in the operative position.

The humidification compartment may not require a separate or additional lid in order to seal the humidification compartment as the sealing can be achieved by the humidification chamber.

The strap 63 may include a rigid handle 64 that is pivotally connected to the top face of the strap 63. An upper face of the strap 63 may also include a recessed section 65 that receives the handle 64 when pivoted toward the strap.

FIGS. 6A to 6D—Embodiment Having a Holder for Applying a Pressing Force to the Humidification Chamber FIGS. 6A to 6D illustrate an apparatus 20 including a compartment 22 having a heater plate 29 and a compartment body 32 that receives a humidification chamber 24. The apparatus 20 also includes a lid 71 that closes the humidification chamber 24. The apparatus 20 also includes a holder 53 that, when in the operative position, presses against a humidification chamber 24 so that the heater base 28 is held to a heater plate 29 by holding force “A” to enhance thermal engagement therebetween.

The holder 53 has a collar structure including a frame 66 that is pivotally connected to the compartment by a hinge mounting 55 and a central opening 70 in which the lid 71 is located when the holder 53 is in the operative position. The frame 66 has a top wall 67, an outer skirt 68 about the outer perimeter of the top wall 67, and an inner skirt 69 that extends about the central opening 70. The outer skirt 68 of the frame 66 aligns or sits flush with an outer surface of the side wall 62 of the compartment 22 when the holder 53 is in the operative position.

Figure 6A:
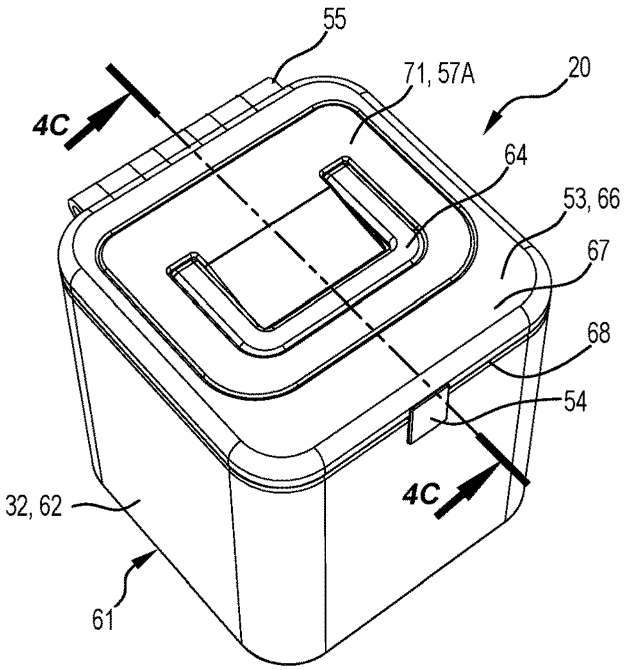
FIGS. 6A and 6B are schematic perspective views of an apparatus having a holder in an operative position for applying a holding force to the humidification chamber, and an inoperative position, respectively.
Figure 6B:
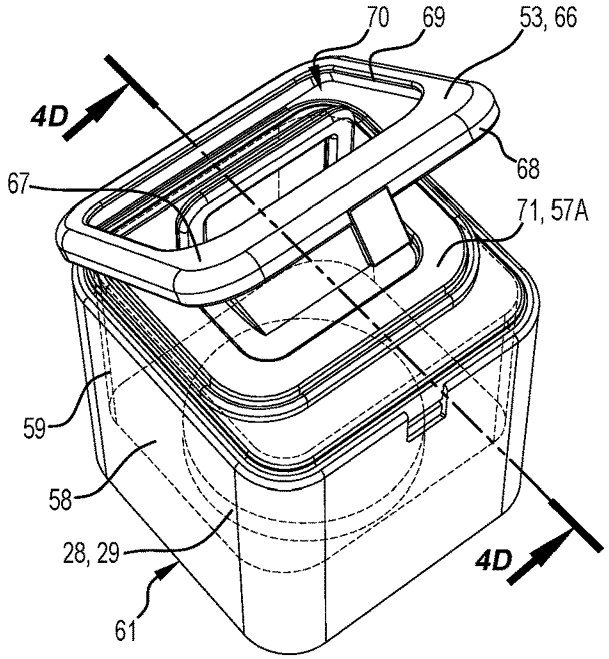
Figure 6C:
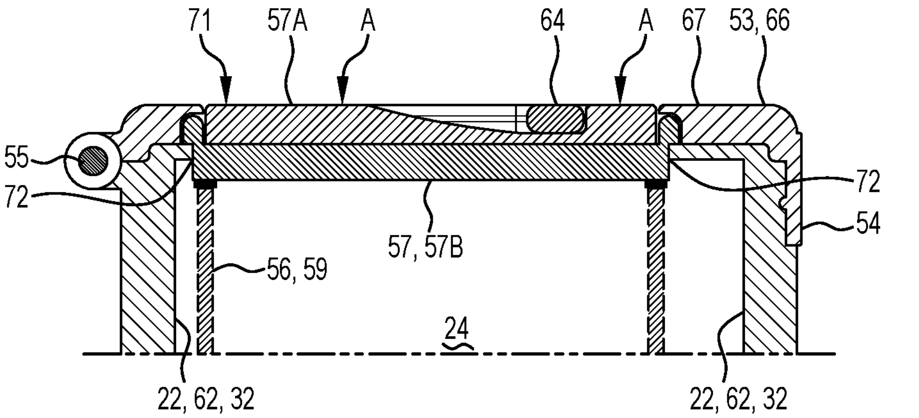
FIGS. 6C and 6D are cross-sectional views of the apparatus as identified by the arrows in FIGS. 6A and 6B.

The top wall 67 of the frame 66 also aligns or sits flush with a top wall 67 of the lid 71, see FIG. 6C.

The hinge mounting 55 non-releasably connects the holder 53 and the frame 66 to a rear panel of the compartment 22. The holder 53 also includes a latching device 54 disposed at a front of the frame 66 for securing the holder 53 in the operative position. The latching device 54 may be any suitable mechanism, including a sliding latch, a press button latch or a rotating latch.

In other examples, not illustrated, the hinge mounting 55 may connect the holder 53 to the compartment 22. During normal operation the hinge mounting 55 remains connected to the compartment 22, but can be disconnected by rotating past the open stop position, i.e. further than its normal range. In other words, the holder 53 may be connected to the compartment 22 and is attached to the compartment 22 in the operative position, but may be disconnected when excess force is applied. To prevent the holder 53 from becoming lost when detached from the compartment 53, the holder 53 may be tethered to the compartment 22, for example, by a lanyard (not illustrated).

The humidification compartment 22 has a compartment body 32 including a base wall 61 and a side wall 62 defining an upwardly facing opening 72. The side wall 62 has a front panel that may, for example, have user controls, a rear panel, and opposite side panels. A heater plate 29 having a biasing arrangement may be mounted to the base wall 61 or form part of the base wall 61. The biasing arrangement allows the heater plate 29 to move in response to the holding force “A” of the heater base 28 on the heater plate 29.

The humidification chamber 24 includes a water tub 56 which receives water for humidifying the stream of gas 34 passing through the humidification chamber 24, and a water tub cover 57. The water tub 56 includes a bottom wall 58 and sidewalls 59 extending from the bottom wall 58. The heater base 28 may form part of the bottom wall 58. In one example the water tub 56 may be configured so that when the water tub 56 is received by the humidification compartment 22, the side walls 59 of the water tub 57 may extend above the opening of the compartment. In another example, the water tub 57 may be configured so that the side wall 59 of the water tub 57 is within the opening of the compartment 22.

The lid 71 of the apparatus 20 may consist of the water tub cover 57 which fits onto the water tub 56 and is engaged by the holder 53. The water tub cover 57 has a peripheral flange 60 that extends about the lid 71 and engages the opening 72 of the compartment 22 in order to seal the compartment 22. The peripheral flange 60 may have a sealing lip for sealing the engaging the opening of the compartment 22 and does not prevent the holder 53 from applying a holding force “A”

to the humidification chamber 24. As shown in FIG. 6C, the outer face of the lid 71 of the apparatus sits flush with the top wall 67 of the holder 53.

The lid 71 of the apparatus 20 may consist of inner layer 57B in the form of a water tub cover 57 and an outer cover 57A that sits on the water tub cover 57. When the lid 71 includes an outer cover 57A, the outer cover 57A and the water tub cover 57 may be fitted together, for example, by way of press fitted friction formations.

The water tub cover 57 may have a single integrally formed structure, or alternatively, the water tub cover 57 may include two or more separable elements, such as plugs for sealing water filling apertures. The water tub cover 57 also allows the humidification chamber 24 to be sealed.

Figure 6D:
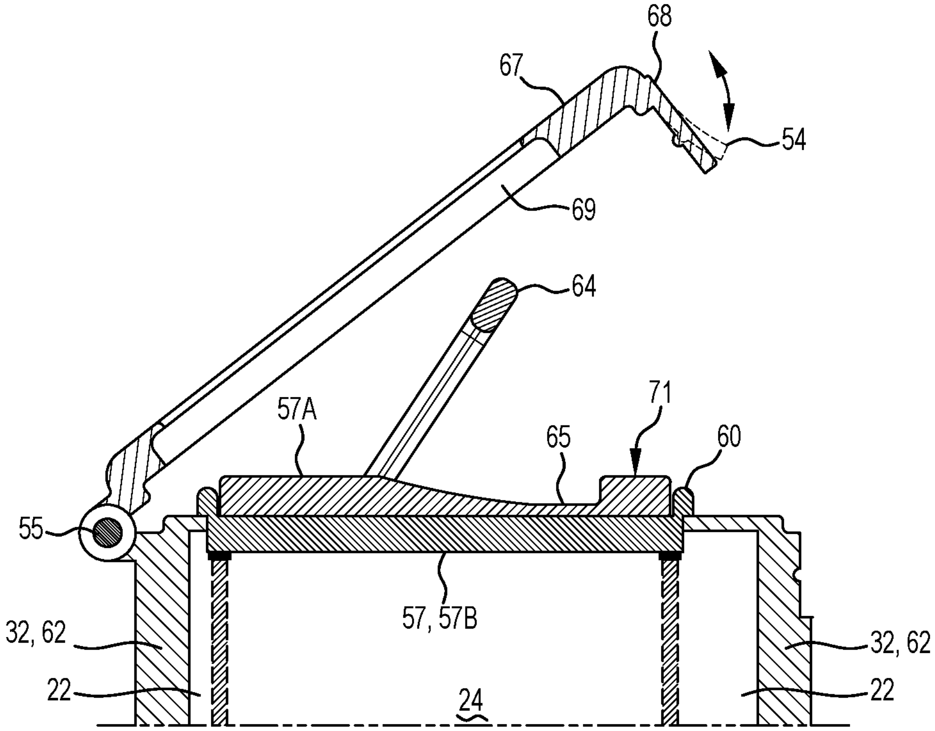

FIGS. 6B to 6D illustrate the water tub cover 57 extending about the opening of the compartment 22 and the outer cover 57A being centrally located on top of the water tub cover 57 which forms the inner layer 57B. When the holder 53 is located in an operative position, the holder 53 presses against either one or a combination of the water tub cover 57 and the outer cover 57A. By pressing against the water tub cover 57 and/or the outer cover 57A, the holder 53 either directly or indirectly presses against the humidification chamber 24 which holds the heater base 28 against the heater plate 29 by the holding force "A". The holding force assists in completing a face-to-face contact between the heater base 28 and the heater plate 29.

The holder 53 does not itself close or seal the humidification compartment 22 when in the operative position because the holder 53 does not extend over the opening of the compartment. However as described above, at least one of the water tub 56 or the water tub cover 57 may extend from the opening of the compartment 22. For example, the water tub cover 57 illustrated in FIGS. 6C and 6D includes the rim 60 that extends about the water tub cover 57 and may engage the wall of the compartment 22 about the opening 72 to seal and close the compartment 22 when the holder 53 presses against the lid 71. The flexible rim 60 can flex in response to the holder 53 pressing against the lid 71, and in turn, the holder 53 applying the holding force "A" to the humidification chamber 24.

As the humidification compartment 22 and the chamber 24 can be sealed which allows the gas stream 34 to be conveyed through the humidification chamber 24 in either one of the arrangements shown in FIGS. 1A and 1B, and in particular, FIG. 1B in which the gas stream 34 can be supplied directly into the chamber 24, or supplied indirectly into the chamber 24 via the compartment 22.

An outer face of the lid 71 also includes a handle 64 that moves between a stowed position as shown in FIGS. 6A and 6C, and in use position in which the handle 64 is pivoted away from the outer cover 57A. The handle 64 can be used for lifting the humidification chamber 24 from the compartment 22 when the holder 53 has either been released and pivoted away from the compartment 22 or has been detached from the compartment 22.

FIGS. 7A to 7G—Embodiment Having a Detachable Lid

FIGS. 7A to 7G illustrate an apparatus 20 including a compartment 22 having a heater plate 29 and a compartment body 32 having an opening 72 that receives a humidification chamber 24 having a heater base 28. The apparatus 20 includes a detachable lid 71 that can be attached to the compartment 22 in a sliding motion and moved between opened and closed positions. When the lid 71 is in the closed position, the lid 71 presses against the humidification chamber 24 so that the heater base 28 of the humidification chamber 24 is held against the heater plate 29 to enhance thermal engagement therebetween. When the lid 71 is in the closed position, the lid 71 closes the humidification compartment 22 and may seal the compartment 22.

When the lid 71 is in the open position, the lid 71 can be detached from the compartment 22 to allow the humidification chamber 24 to be removed from the compartment 22.

The lid 71 and the compartment 22 have a closure mechanism 73 (see FIG. 7D) that allows the lid 71 to be attached to the compartment 22 by sliding the lid 71 on compartment 22 and thereby closes the compartment 22. The closure mechanism 73 includes a first engagement formation 74 (see FIGS. 7E to 7G) on the lid 71 and a co-operating second engagement formation 75 (see FIGS. 7D to 7G) on the compartment 22. The first engagement formation 74 of the lid 71 includes an elongated limb, such as a lip, flange, ridge or tongue, which will be hereinafter be referred to as the lip 76, which is received by the second engagement formation 75 of the compartment 22 such as an elongate cavity such as an overhang, slot, groove, channel, or recess, which will hereinafter be referred to as the groove 77.

Figure 7A:
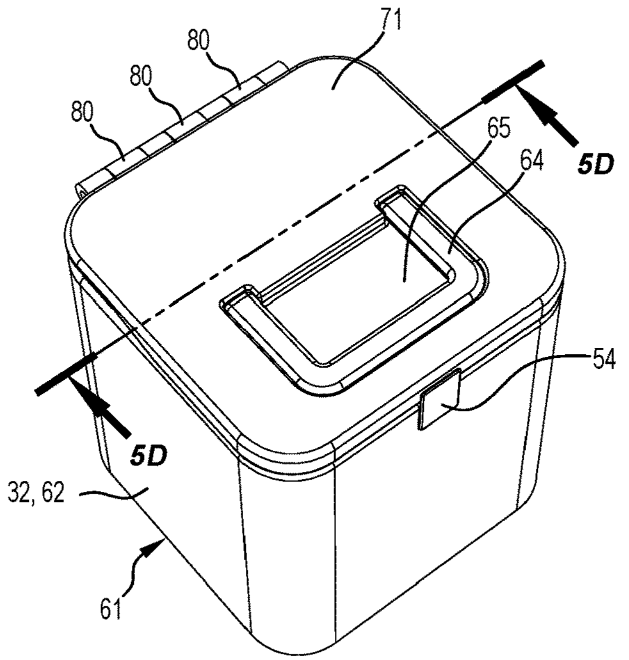
FIGS. 7A to 7C are schematic perspective views of an apparatus having a detachable lid.
Figure 7B:
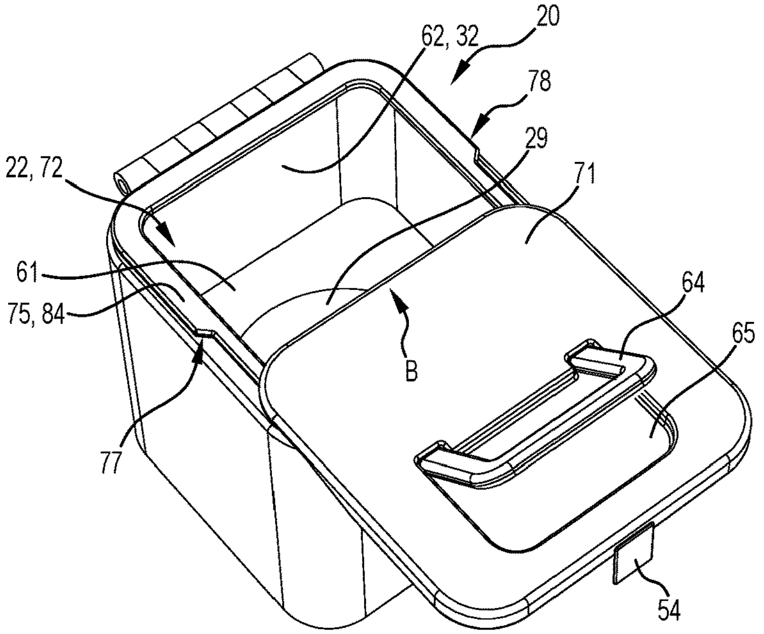
Figure 7C:
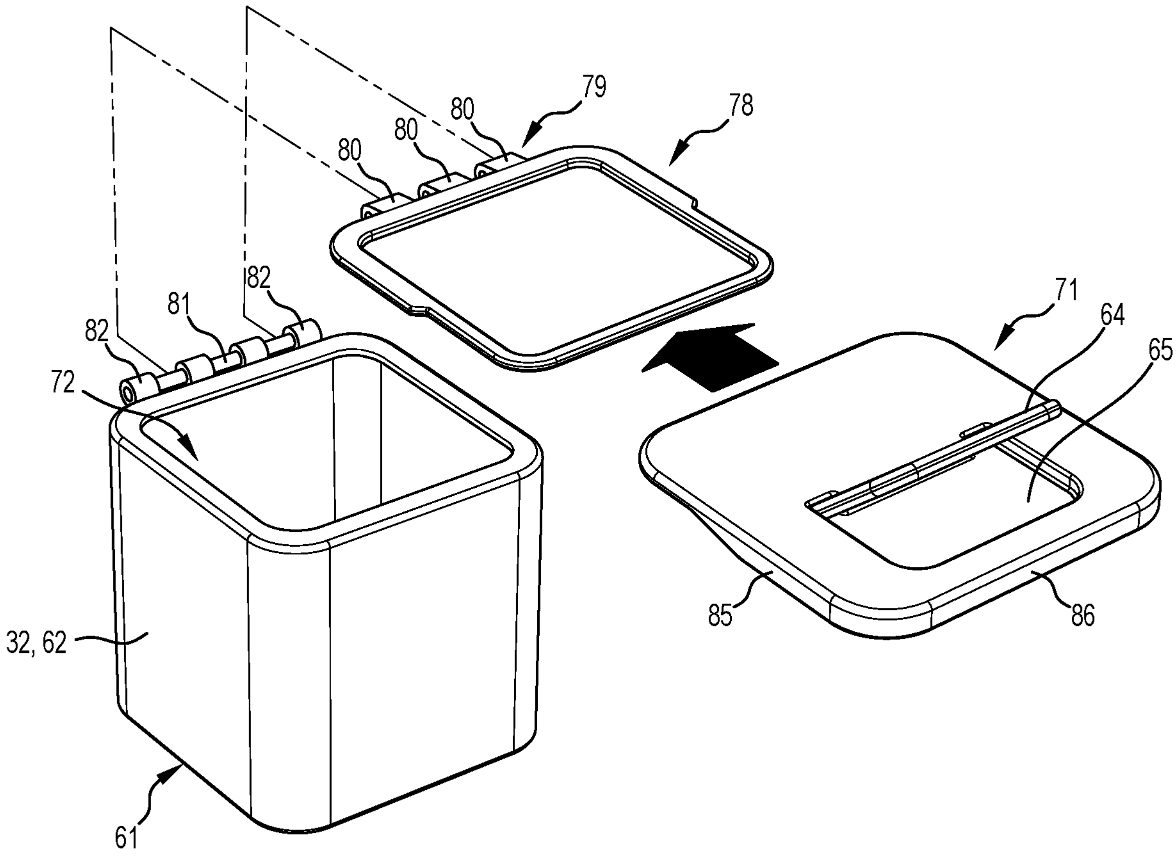

The closure mechanism 73 is arranged to allow the lid 71 to be attached to the compartment 22 by sliding the lid 71 in a rearward direction from a front panel of the compartment 22 toward a rear panel of the compartment 22, as shown by arrow "B" in FIG. 7B. However, it will be appreciated that the closure mechanism 73 may be arranged in a number of other configurations which allows the lid to be attached to the compartment 22 by sliding the lid 71 in a direction from back-to-front and in a direction from side-to-side.

The second engagement formation 75 may be retrofitted to an upper edge of an existing compartment 22, or alternatively, the second engagement formation 75 may be integrally formed with the compartment body 32 of the compartment 22. As can best be seen in FIG. 5C, the second engagement formation 75 can be provided by a ring body 78 that can be retrofitted to the opening 72 of a compartment 22, in which the ring body 78 provides the second formation 75 for engaging with a first engagement formation 74 of the lid 71.

The ring body 78 can be fitted about the upper edge of the opening 72 of the compartment 22 and includes an attachment formation 79 for connecting to an existing hinge mounting 55 at the rear of the compartment 22. The attachment formation 79 may include a set of separated fingers 80 that are interconnected by a rod 81 that is received by a set of sleeves 82 positioned along the rear panel of the compartment 22.

The ring body 78 also has a bottom surface which sits on the upper edge of the opening 72 of the compartment 22. The bottom surface may be adhered to the upper edge of the opening 72 using any suitable adhesive including a pressure adhesive that is pre-applied to the bottom surface and protected by a removable peel strip prior to application, or a multicomponent adhesive that is mixed and applied in situ.

The ring body 78 may be made of any suitable material including plastic moulded materials, silicon materials and so forth. Suitably, the ring body 78 extends about the opening 72 of the compartment 22 and is made of a resiliently flexible material that can engage the inside face of the lid 71 and form a seal against the inside face of the lid 71 to seal the compartment 22 when the lid 71 is in the closed position.

In another example, not shown in the Figures, the second engagement formation 75 may be integrally formed with the body of compartment 22. In this situation, it will be appreciated that attachment formation 79 and the various parts thereof can be omitted.

Irrespective of whether the second engagement formation 75 is integral with the body of the compartment or provided as a ring body 78, the second formation 75 includes a riser section 83 and the top flange 84 extends from the riser section 83, in which the top flange 84 overhangs the riser section 83. This arrangement forms the groove 77 that faces sideways of the opening 72 of the compartment 22. As can best be seen in FIG. 5D the groove 77 has a rectangular cross-section which is formed between an upper edge of the sidewall 62 of the compartment 22, the riser section 83 extending upward from the upper edge and the top flange 84 extending outward from the riser section 83. The cross-section also shows that the top flange 84 has a tapering profile that provides a declined surface heading in a direction toward the outer extremity of the flange 84. The inner surface of the lid 71 provides a corresponding tapered surface.

It will be appreciated that the groove 77 may have any suitable cross-section, such as a tapered cross-section, a dovetail cross section, or a circular cross-section.

The first engagement formation 74 is a lip 76 that extends inwardly on a part of the side skirt 85 of the lid 71. As can be best seen in FIG. 7C, the lid 71 has a top wall 76, a front skirt 86, side skirts that extend from the front skirt 86 toward the rear, but there is no rear skirt.

Figure 7D:
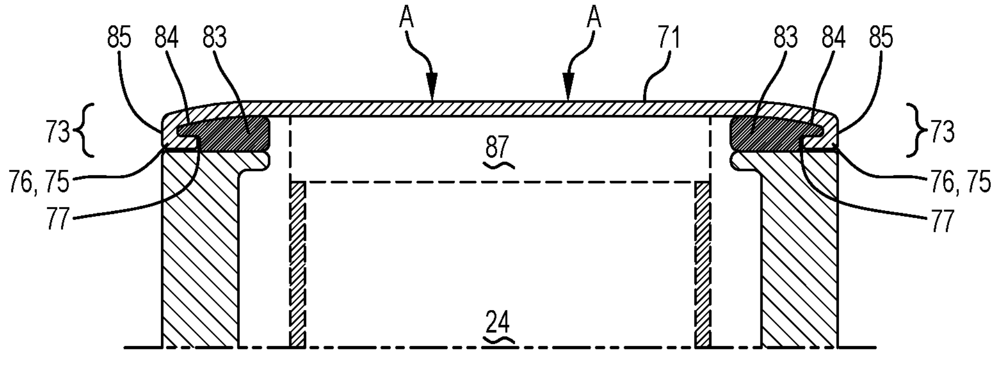
FIG. 7D is a cross-sectional view of the apparatus as identified by the arrows in FIG. 7A.
Figure 7E:
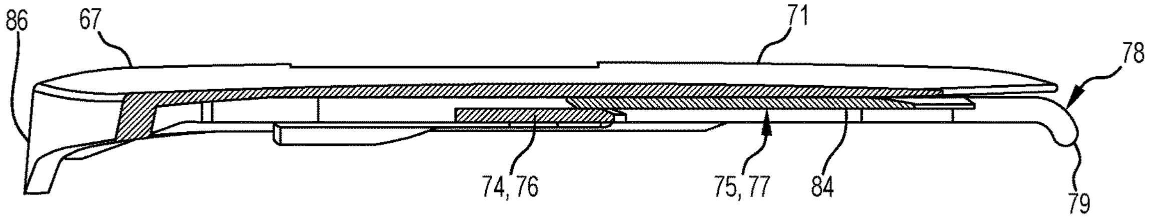
FIGS. 7E to 7G are schematic cross-sectional views illustrating the engagement formations for attaching the lid to the compartment at various stages, including engaged, aligned to be engaged and detached, respectively.
Figure 7F:
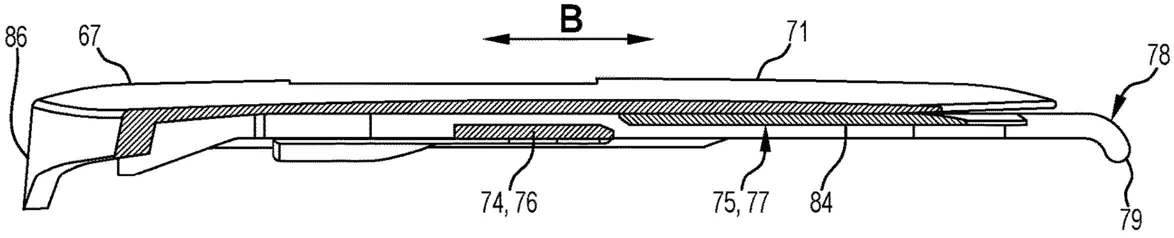
Figure 7G:
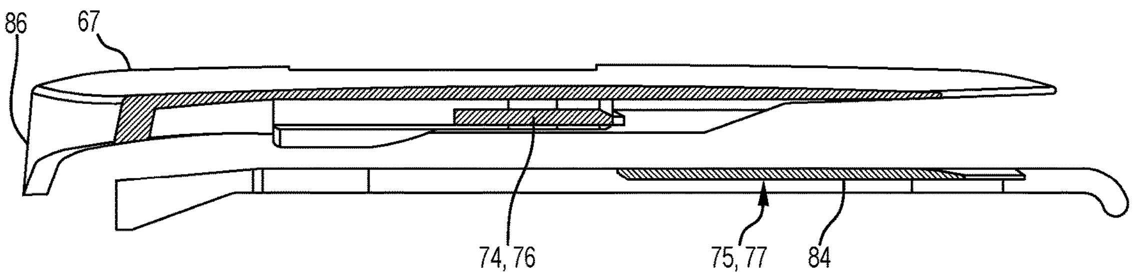

FIGS. 7E, 7F and 7G illustrate cross-sectional views of the lid 71 including the lip 76, and the groove 77 of the ring 78. FIG. 7G illustrates a situation in which the lid 71 is positioned over the opening 72 of the compartment 22, the closure mechanism 73 is not engaged and the lid 71 is separated. FIG. 7F illustrates the lid 71 being seated down onto a sealing surface of the compartment 22 with the lip 76 of the first engagement formation 74 of lid 71 facing the groove 77 of the second engagement formation 75, however, the closure mechanism is yet to be engaged. FIG. 7G illustrates the lip 76 and groove 77 of the closure mechanism 73 engaged which attaches the lid 71 to the compartment 22 and position the lid 71 so as to press against to the humidification chamber 24. The lid 71 can also seal the opening 72 of the compartment 22 by, for example, the ring body 78 about the opening 72. When the lid 71 is in the closed position, the lip 76 underlies the top flange 84 and is received by the groove 77 by a closing distance which is positioned intermediate of the front and rear panels of the compartment 22. In the case of FIG. 7E, the closing distance is in the range of 10 to 50 millimetres in length. However, it will also be appreciated depending on the location of the top flange 84 and the lip 76, the position of the closing distance and the length of the closing distance can be varied. For example, the closing distance may be located closer to the rear panel of the compartment 22. In another example the length of the closing distance may extend over half the length of the sidewall of the compartment. In other example, the closing distance may be in the range of 10 to 80 millimetres, suitably in the range of 30 to 70 millimetres.

As can be seen in FIGS. 7E to 7G, the leading edge of the lip 76 is tapered and the leading edge of the top flange 84 which faces the leading edge of the lip 76 is also tapered to assist in the lip 76 being guided into the groove 77 as the lid is slid into the attached and closed position.

By inter-fitting the first and second formations 74 and 75, which for embodiment illustrated is completed by sliding the lip 76 of the lid 71 along the groove 77 of the compartment 22 or the ring body 78 attached to the compartment 22, the inner face of the lid 71 engages and presses against the humidification chamber 24 in order to hold the heater base 28 of the humidification chamber 24 to the heater plate 29 of the compartment 22 by the holding force. Block 87 shown in FIG. 7D represents contacting formations between the inner face of the lid 71 and the humidification chamber 24. For example, although not illustrated in detail, the inner face of the lid 71 may include contact points, rails formations or other engagement formations that press against the humidification chamber when the lid is attached and located in the closed position.

Block 87 can also represent a water tub cover 57 or an additional component between the water tub cover 57 and the humidification chamber 24. In any event, the humidification chamber 24 can be sealed by the block 87, in which case the gas stream 34 can be supplied to the humidification chamber 24 in accordance with FIG. 1A. Alternatively, the lid 71 can also seal the compartment 22, in which case the gas stream 34 can be supplied to the chamber 24 via the compartment 22, or directly to the chamber in accordance with FIG. 1B.

The lid 71 includes a top wall 67 that can span over the opening 72 of the compartment 22 and as described above, a side skirt 85 and front skirt 86 extends from the top wall 67 about the front and opposite sides of the lid 71, and no skirt is provided on the rear edge of the lid 71. By maintaining the back region of the lid 71 free of the skirt, a user can more easily observe the first and second closure formations 74 and 75 inter-fitting as a lid is being slid into a closed attached position. In other words, by omitting the skirt from the rear edge of the lid 71, a user is provided with a visual cue for engaging the lid to the compartment 22.

In other arrangements it will be appreciated that the side skirt 85 may extend from the front skirt 86 to the rear edge of the lid 71. In any event, when the lid 71 is in the closed position, the side skirt 85 aligns with an outer face of the side wall 62 of the compartment 22. In other words, the side skirt 85 sits flush with the outer face of the side wall 62 of the compartment 22 when the lid 71 is attached to the compartment 22.

An outer face of the lid 71 also includes a handle 64 that moves between a stowed position as shown in FIG. 7A, and in use position, in which the handle 64 is pivoted away from the lid, as shown in FIG. 7B. The handle 64 can be used for sliding the lid between the open and closed positions, and in particular for sliding the lid 71 forwardly to detach the lid 71.

The lid 71 has a latching device 54 for securing the lid 71 in the attached closed position. The latching device 54 may have any suitable structure including a sliding lock, press button lock or a pivoting lock, and may be located within a housing located within the top wall and/or the skirt of the lid. Preferably the latching device may be located at the front of the lid. An additional latching device or an alternative latching device may also be located at the rear of the lid or at the sides.

FIG. 8A to 8D—Embodiment Having a Detachable Lid

FIGS. 8A to 8D illustrate an apparatus 20 including a compartment 22 having a heater plate 29 and a compartment body 32 having an opening 72 that receives a humidification chamber 24 having a heater base 28. The apparatus 20 includes a detachable lid 71 that can be moved in a sliding motion between opened and closed positions. When the lid 71 is in the closed position, the lid 71 presses against the humidification chamber 24 so that the heater base 28 of the humidification chamber 24 is held against the heater plate 29 to enhance thermal engagement therebetween.

The lid 71 and the compartment 22 have a closure mechanism 73 that allows the lid 72 to be attached to the compartment 22 by sliding the lid 71 over the opening to close the compartment 22. Specifically, the closure mechanism 73 (see FIG. 8A) includes a first engagement formation 74 (see FIGS. 8B and 8D) on the lid 71 and a co-operating second engagement formation 75 (see FIGS. 8B and 8D) on the compartment 22. The first engagement formation 74 of the lid 71 has an elongated limb at the rear of the lid 71, such as a lip, flange, ridge or tongue, which will be hereinafter be referred to as the lip 76 (see FIGS. 8B and 8C), that is received by the second engagement formation 75 of the compartment 22 that has a forwardly facing elongate cavity at the rear compartment 22, such as a slot, groove, channel, or recess, which will hereinafter be referred to as an overhang 88, best seen in FIG. 8D.

Figure 8A:
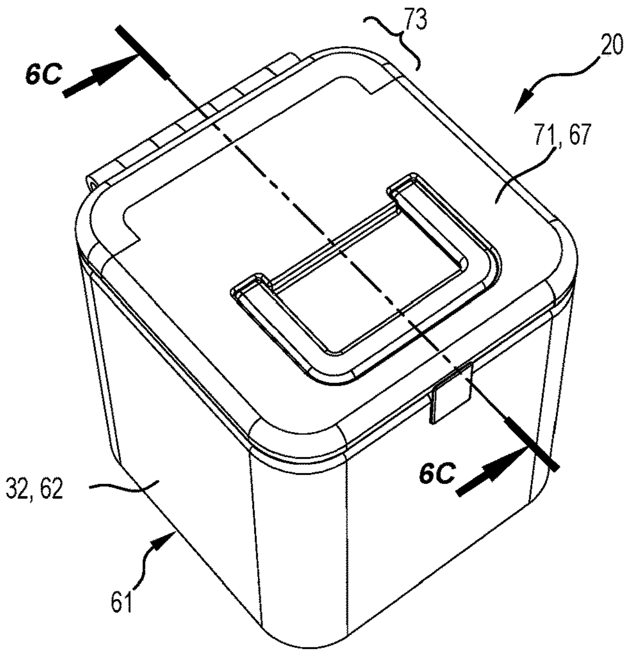
FIGS. 8A and 8B are schematic perspective views of an apparatus having a detachable lid.
Figure 8B:
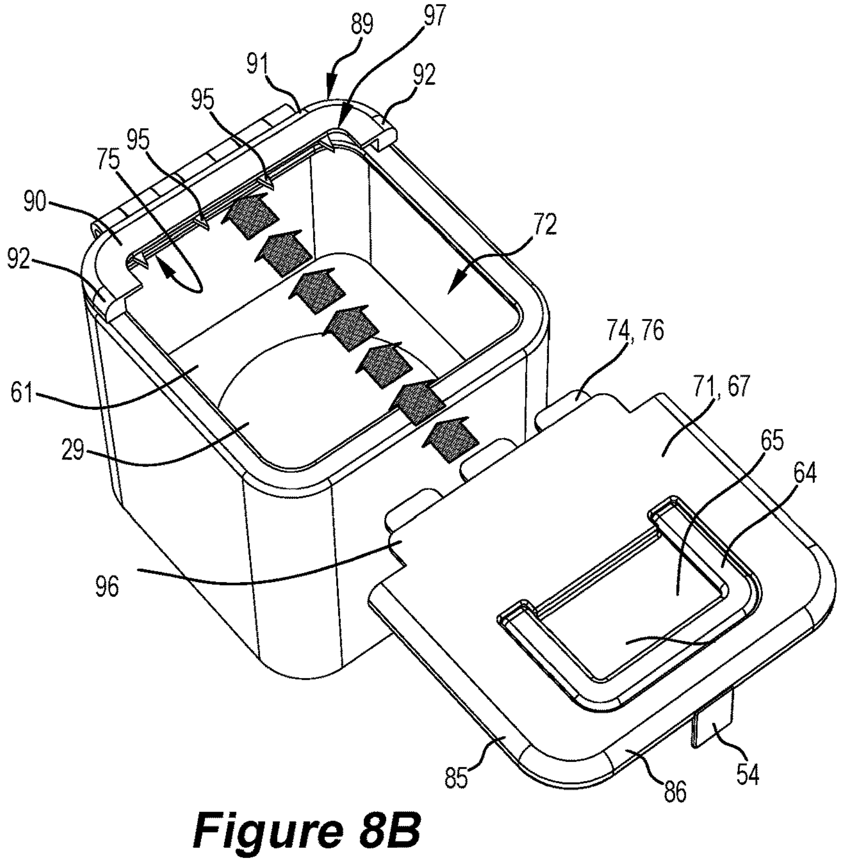

The closure mechanism 73 is arranged to allow the lid 71 to be attached to the compartment 22 by sliding the lid 71 in a rearward direction, as shown by the arrows in FIG. 8B. However, it will be appreciated that the closure mechanism 73 may be arranged in other configurations that allows the lid 71 to be attached to the compartment 22 by sliding the lid 71 in a direction from back-to-front and in a direction from side-to-side.

The lid 71 includes a top wall 67, a front skirt 86 and a side skirt 85 extending about the lid 71. The rear of the lid 7 includes the lip 76 that is rebated below the top wall 67 of the lid 71. The lip 76 extends across over at least half the width of the compartment 22, and suitably approximately three quarters of the width of the compartment 22.

The overhang 88 forms a cavity across the rear of the compartment 22 and includes an outer shell 89 that is spaced from an upper surface 93 of the rear wall of the compartment 22. The outer shell 89 has a top panel 90, rear panel 91, and side panels 92 that define the forwardly facing cavity. As can best been in FIGS. 8A and 8B, the top wall 67 of the lid 71 has an extension 96 (see FIG. 8B) that is received by a complimentary shaped reduction 97 in the top panel 90 of the overhang 88. Inter-fitting or mating the extension 96 and the reduction 97 provides a visual cue as to when the lip 76 has been properly received by the cavity. The height of the cavity between the top panel 90 and the upper surface 93 of the rear wall of the compartment 22 is sized to receive the lip 76 and press the lip 76 of the lid 71 toward the humidification chamber 24.

The overhang 88 is also segmented into three sections by dividers 95 that extend between the top wall 90 and the upper surface 93 of the compartment 22. Similarly, the lip 76 of the lid 71 has cut out sections that receive the dividers 95 which help guide the lid 71 into the correct position as the lid 71 is being slid in a rearward motion during closing.

The outer shell 89 in FIGS. 8A to 8D illustrates that the outer shell 89 is attached to the rear the compartment 22 by a coupling, such as a finger joint or hinge mounting 55. In other examples, the outer shell 89 may be joined to the compartment 22 via an adhesive or integrally formed with the side wall 62 of the compartment 22. In this situation, it will be appreciated that finger joint or hinge mounting 55 can be omitted.

When the lip 76 is fully received within the cavity, the front portion of the lid 71 may be pushed toward the humidification chamber 24 by a user to close and seal the lid 71 against the body of the compartment 22. The lid 71 can be secured in the closed and sealed position by a suitable latching device 54. In this instance, the latching device 54 can prevent a front of the lid 71 from moving away from the compartment 22 and prevent the lid 71 from sliding forward. However, it will be appreciated that the degree to which the lid 71 needs can be pushed downward will depend on the fit between the lip 76 and the cavity. In some instances, the fit between the lip 76 and the cavity may be such that the lid 71 does not require or cannot be pushed toward to the lid 71 by the user. In other situations, the fit between the lip 76 and the cavity may provide some downward movement.

Figure 8C:
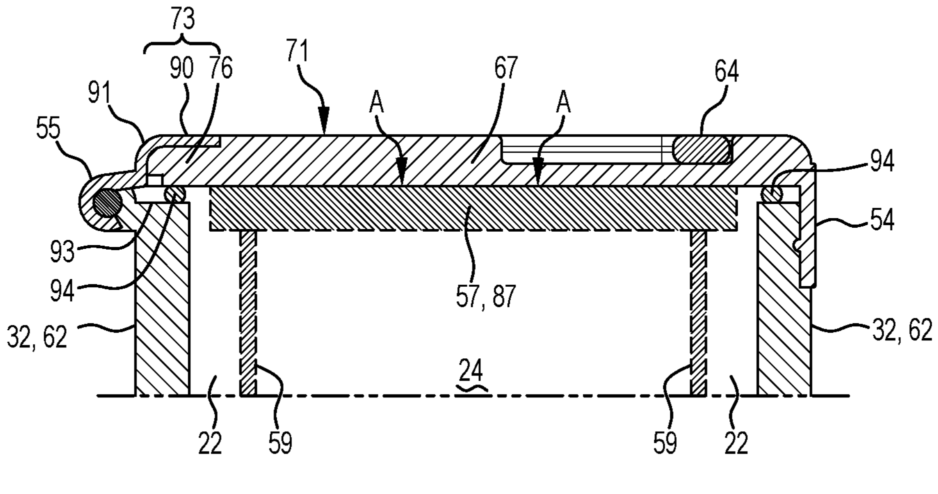
FIG. 8C is a schematic cross-sectional view through the apparatus identified by the arrows in FIG. 8A
Figure 8D:
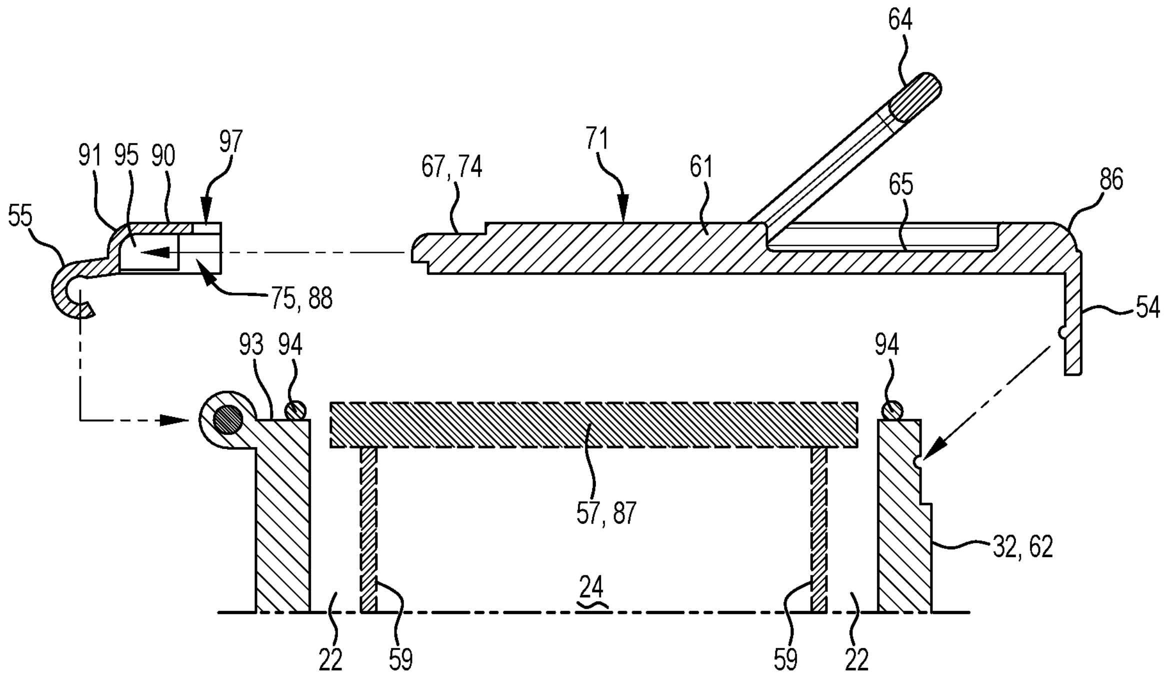
FIG. 8D is an exploded view of the components shown in FIG. 8C.
Figure 9A:
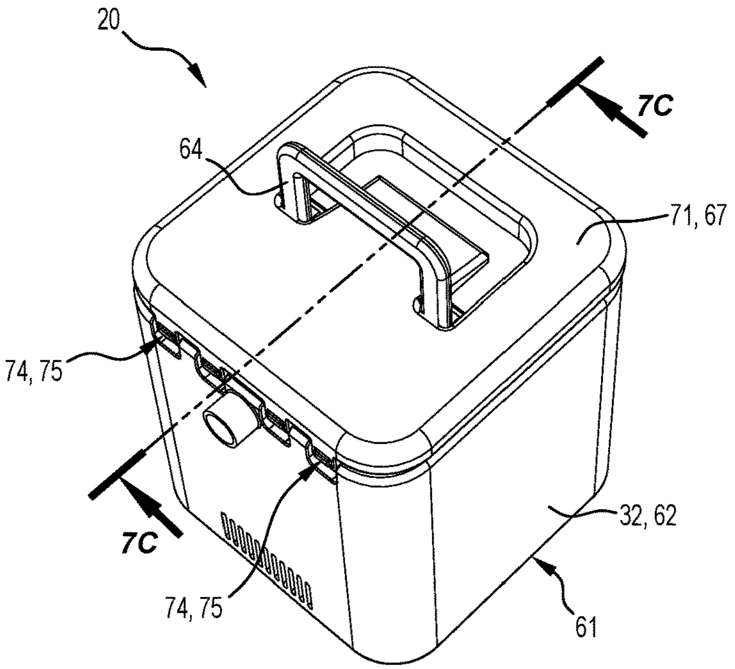
FIGS. 9A and 9B are schematic perspective views of an apparatus having a detachable lid, in which the lid is attached to the compartment and applies a holding force to the humidification chamber, and the lid is detached from the compartment, respectively.
Figure 9B:
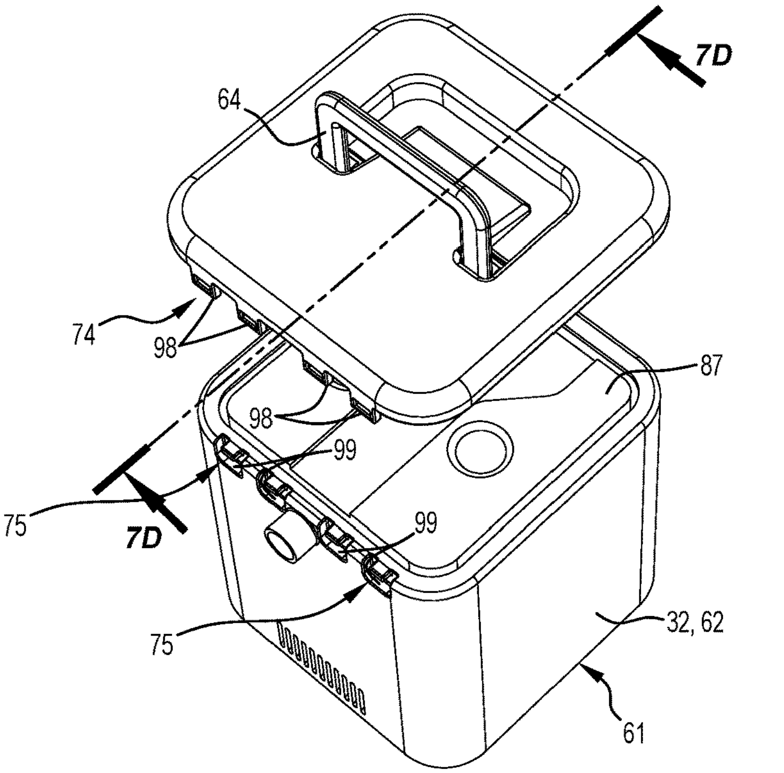
Figure 9C:
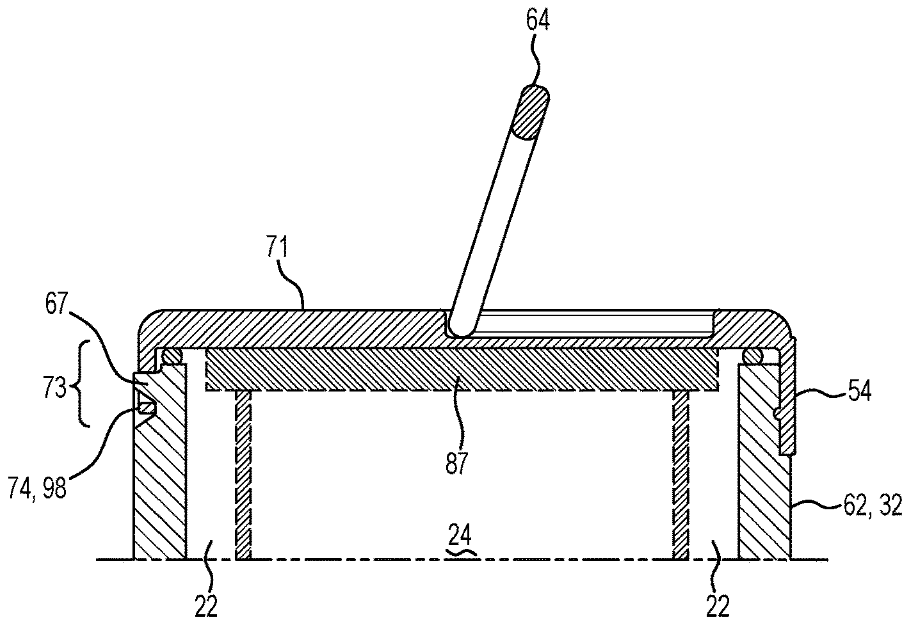
FIGS. 9C and 9D are schematic cross-sectional views through the apparatus identified by the arrows in FIGS. 9A and 9B respectively.
Figure 9D:
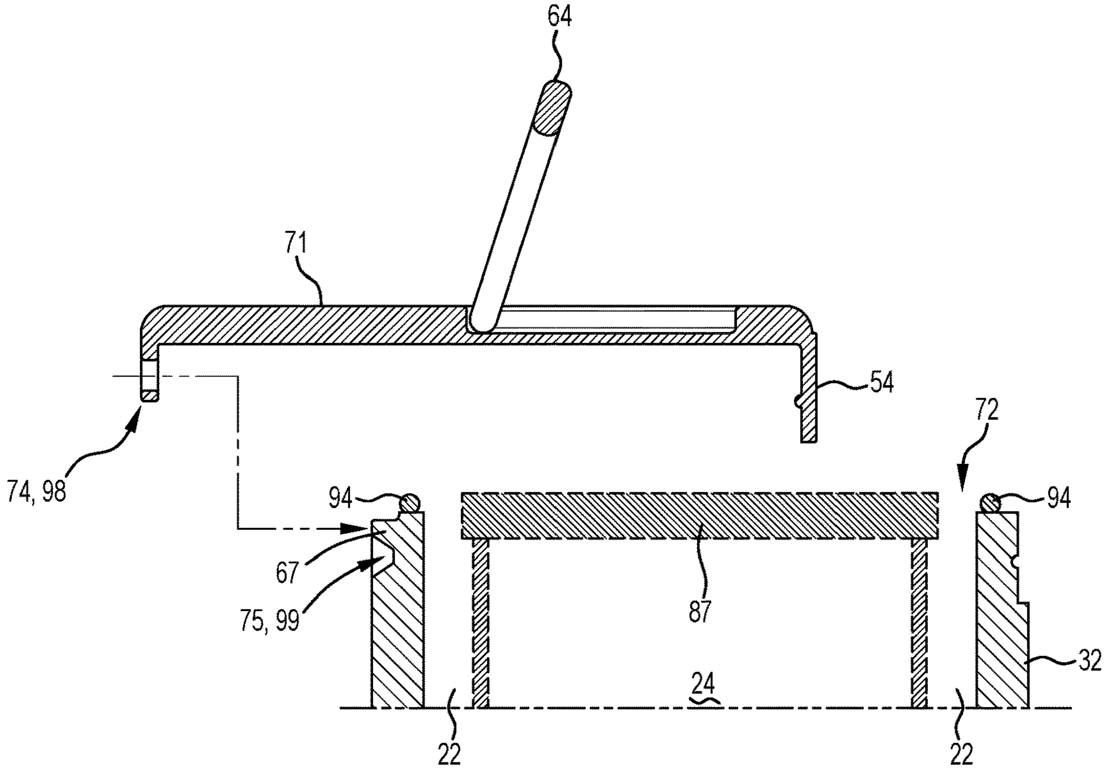

When the lip 76 has been fully received within the cavity, the fit between the overhang 88 and the lip 76 may prevent any upward movement of the lid 71, and applies a downward force to the lid 71 which in turn applies a pressing force to the humidification chamber 24 in the direction of arrows "A", see FIG. 8C. The lid 71 may also form a seal with the compartment 22 by engaging a sealing gasket 94. That is to say, the lid 71 lies flat and does not require a user to push the front of the lid downward.

The apparatus 20 also includes a water tub cover 57, represented by block 87, that seals the humidification chamber 24. The inner surface of the lid 71 pressed directly against the water tub cover 57 of the humidification chamber 24.

The latching device 54 may be any suitable latch, such as a press button latch, sliding latch or a rotating latch.

An outer face of the lid 71 also includes a handle 64 that moves between a stowed position as shown in FIGS. 8A and 8C, and in use position in which the handle 64 is pivoted away from the lid 71. The handle 64 can be used for sliding the lid between the open and closed positions and for handling the lid 71 when the lid 71 has been detached from the compartment 22.

When the lid 71 is in the open position, the lid 71 can be detached from the compartment 22 so as not to obstruct the opening so the humidification chamber 24 can be removed from the compartment 22.

The lid 71 may be tethered to the compartment, for example, by using any suitable lanyard to prevent the lid from becoming lost when the lid 71 is detached from the compartment.

FIG. 9A to 9D—Embodiment Having a Detachable Lid

FIGS. 9A to 9D illustrate an apparatus 20 including a compartment 22 having a heater plate (not shown) and a compartment body 32 having an opening 72 (see FIG. 9D) that receives a humidification chamber 24. The humidification chamber 24 has a heater base (not shown). The apparatus 20 also has a detachable lid 71 that can be moved in a sliding motion between opened and closed positions. When the lid 71 is in the closed position, the lid 71 presses against the humidification chamber 24 so that the heater base of the humidification chamber 24 is held against the heater plate to enhance thermal engagement therebetween.

The lid 71 and the compartment 22 have a closure mechanism 73 (see FIG. 9C) that allows the lid 71 to be attached and detached to open and close the compartment 22. The closure mechanism 73 includes a first engagement formation 74 on the lid 71 and a co-operating second engagement formation 75 on the compartment 22. The first engagement formation 74 includes a limb, which will be hereinafter be referred to as claws 98, which is received by a cavity of the second formation 75 of the compartment 22, which will hereinafter be referred to as the saddle formations 99. As can be seen, the rear of the lid includes two pairs of claws 98. Two of the claws 98 are located on each half of the lid 71 of the apparatus 20. The compartment 22 comprises two pairs of saddle formations 99 that have a rearwardly facing opening.

The lid 71 is attached to the compartment 22 by locating the claws 98 of the lid 71 in the saddle formations 99. The saddle formation 99 have a top wall 67 that is declined and presses down on the claws 98 as the claws 99 move deeper into the saddle formations 99. In turn, the lid 71 of the compartment 22 presses down on the humidification chamber 24 located in the compartment 22.

A latching device 54 is located at the front of the lid 71 which secures the front of the lid to the compartment 22. Operating the latching device 54 may also pull the lid 71 forwardly, which pulls the claws 98 deeper into the saddle formation 99 and increases the pressing force of the lid 71 on the humidification chamber.

As can be seen the lid 71 has a top wall 67 and skirt extending about the top wall 67. The outer surfaces of the skirt and the side walls 62 of the compartment align flush when the lid is attached to the compartment 22.

The lid 71 may engage a sealing gasket 94 to the seal the compartment 22, and the humidification chamber 24 may have a water tub cover, presented by the block 87. The water tub cover closes the humidification chamber, allowing the apparatus to be operated in accordance with FIGS. 1A and 1B.

The lid 71 also has a pivotally mounted handle 64 that can be used for lifting and moving the lid 71. Although not shown in the Figures a lanyard may also tether the lid to the compartment 22, even when the lid has been detached from the compartment 22.

In another example not illustrated in the Figures, the first engagement formation of the lid may be a rearward facing saddle formation located toward the rear of the lid and the second engagement formation of the compartment may be a positioning rod mounted on a support on the rear edge of the compartment.

FIGS. 10A to 10H—Embodiment Having a Holder that Includes a Support and Engaging Member FIGS. 10A to 10H illustrate an apparatus 20 including a humidification chamber 24, such as a water tub having a heater base 28 in which water is volatilized, and a compartment 22 having a compartment body 32 with an opening 72 that receives the humidification chamber 24. The compartment 22 has a side wall 62 and a base wall 61 having a heater plate 29 that may or may not be supported on the biasing arrangement.

When it is supported on a biasing arrangement, the heater plate 29 is mounted on springs such as compression springs or a resilient skirt that compress when subjected to a force and provide a reaction force that provides a reaction force.

The apparatus 20 also includes a holder 53 having a support 101 in the form of a lid 71 (best seen in FIGS. 10A, 10B, 10D to 10F) attached to the rear of the compartment 22 on a pivot mounting 55, and an engaging member 100 mounted on the lid 71. The holder 53 is operable between a holding position and a non-holding position, when in the holding position the engaging member 100 presses against the humidification chamber 24 so that the heater base 28 is held against the heater plate 29 by a holding force.

In this embodiment, the lid 71 which forms part of the support 101 can be moved between opened and closed positions to seal the compartment 22. As can be seen, the lid 71 is pivotally mounted to a rear wall of the compartment body 32 on a hinge mounting 55. The lid 71 has a top wall 67, and skirt extending from the top wall, and latching device 54 that is operable to secure the lid 71 closed to the compartment 22.

It will be appreciated that in other embodiments the support 101 may form other parts of the compartment, such as a side wall 62 or a top wall of the compartment that has a fixed orientation. That is say, in other embodiments the support 101 may not be moved between opened and closed positions, however, the engagement member 100 will still be operable to engage and disengage from the humidification chamber 24.

With reference to the holder 53 illustrated in FIGS. 10A to 10H, the holder 53 is operable between the holding position and the non-holding position by at least two actions. Firstly, the support 101 of the apparatus 20 which forms part of the lid 71, can be pivoted from an open position to a closed position. In the closed position, the lid 71 closes and, ideally, seals by engaging a gasket 94 about the opening 72 of the compartment 22. However, the lid 71 is configured so that it does not press against the humidification chamber 24, and suitably does not contact the humidification chamber 24 when the lid 71 is in the closed position. Secondly, the engaging member 100 of the holder 53 can then be moved from the holding position to the non-holding position by operating the engaging member 100, in which the engaging member 100 presses against the humidification chamber 24.

The engaging member 100 can be disengaged from the humidification chamber 24 by at least one of the following actions: moving the holder 53, and in the case of the illustrated embodiment by opening the lid 71 of the apparatus 20 into an opened position which moves the engaging member 100 away from the humidification chamber 24, and/or moving the engaging member 100 away from the humidification chamber 24 without moving the lid 71.

The holder 53 has a handle 64 having a hand grip connected to a lever 102 that is connected to a cam 103 having an outer cam surface 142. More specifically, the hand grip spans between two levers 102 and is connected to the levers 102 at right angles. Each lever 102 is connected to a cam 103 such that operating the handle 64 moves both of the cams 103 simultaneously. Although it is possible that the cam surfaces 142 could move in a sliding motion along a path, in this embodiment the cam surfaces 142 move in a pivoting motion about a pivot axis 104. The cam surfaces 142 are asymmetric about the pivot axis 104 and are configured so that the cam surfaces 142 are spaced from the humidification chamber 24 when the lever 102 is oriented away from the lid 71 in an upright direction, and conversely, the cam surfaces 142 presses against the humidification chamber 24 when the lever 102 is pivoted toward the lid 71.

The inside face of the lid 71 may be arranged so that lid 71 does not engage the humidification chamber 24 when the lid 71 is located in the closed position. Specifically, the only engagement between the holder 53 and the humidification chamber 24 is by the engaging member 100 when in the holding position. That is to say, the lid 71 preferably does not engage the humidification chamber 24 in either the open position or the closed position.

Figure 10A:
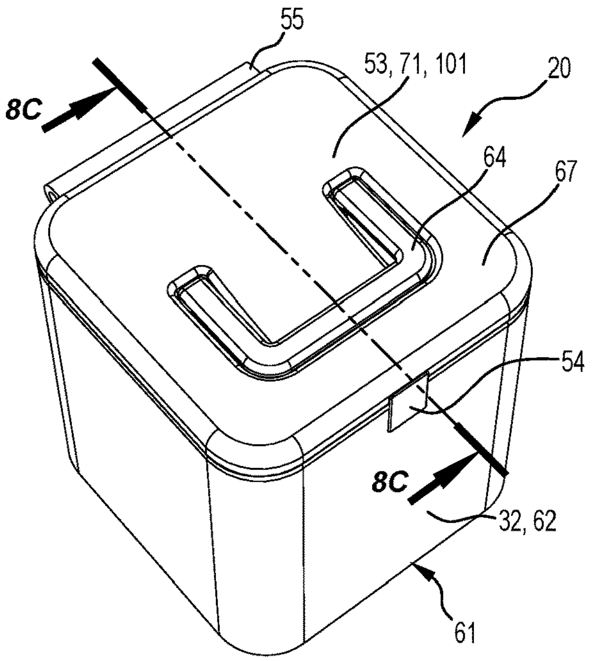
FIGS. 10A and 10B are schematic perspective views of an apparatus having a holder including a support that has a pivoting lid, and an engaging member that has a cam member, in which the holder is in a holding configuration in FIG. 10A and a non-holding configuration in FIG. 10B.
Figure 10B:
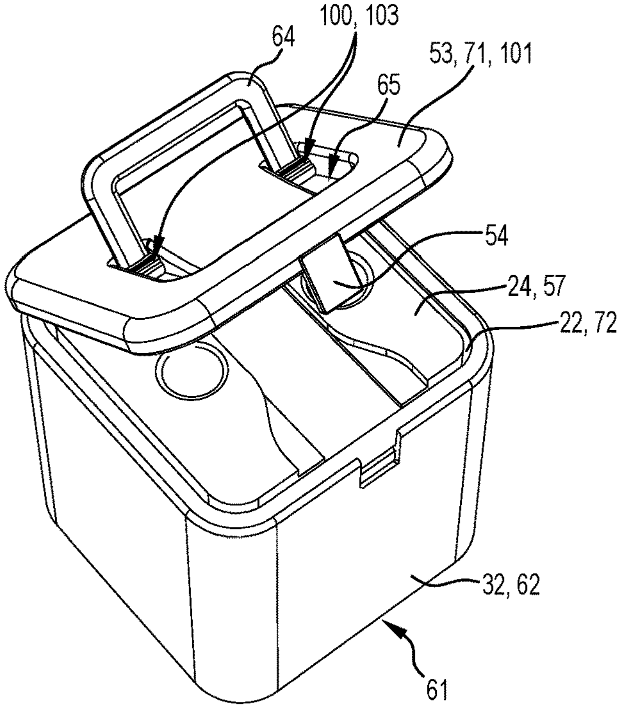
Figure 10C:
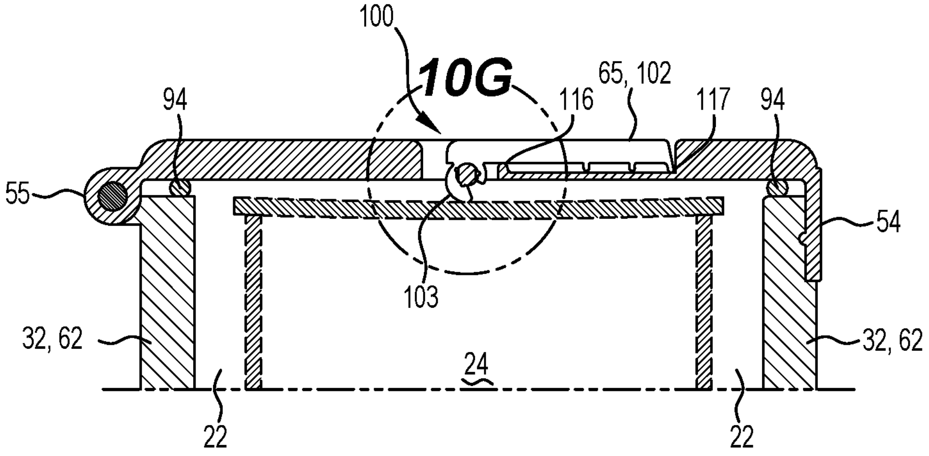
FIG. 10C is a schematic cross-sectional view through the arrows identified in FIG. 10A.
Figure 10D:
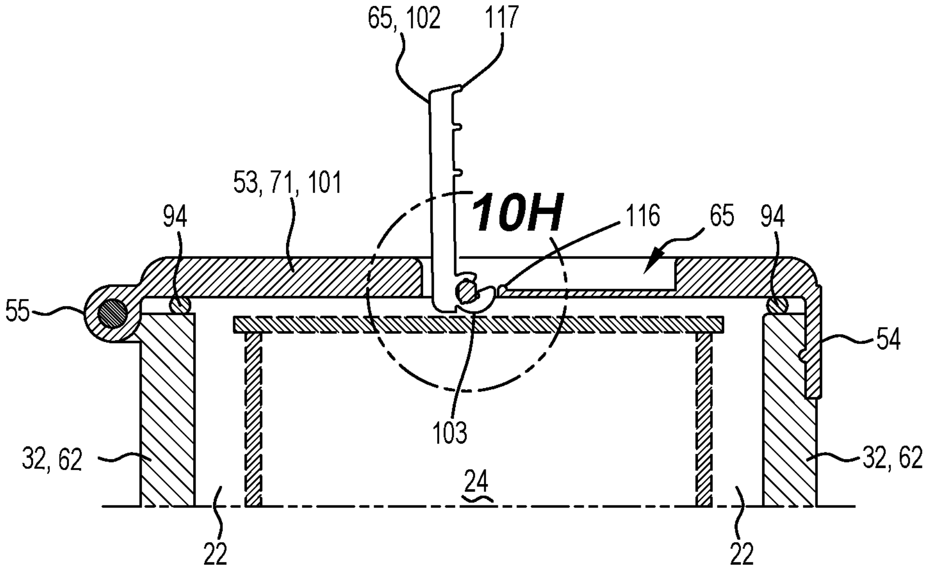
FIG. 10D is a schematic cross-sectional view in which the holder is in a first non-holding configuration and FIG. 10E is a schematic cross-sectional view of the apparatus in which the holder in the non-holding configuration as shown in FIG. 10B.
Figure 10E:
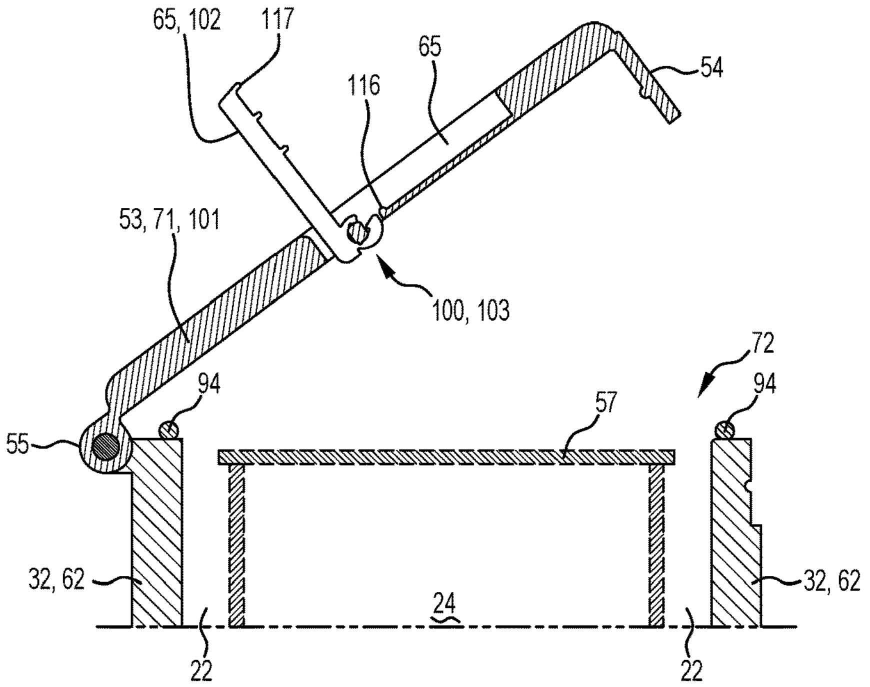
Figure 10F:
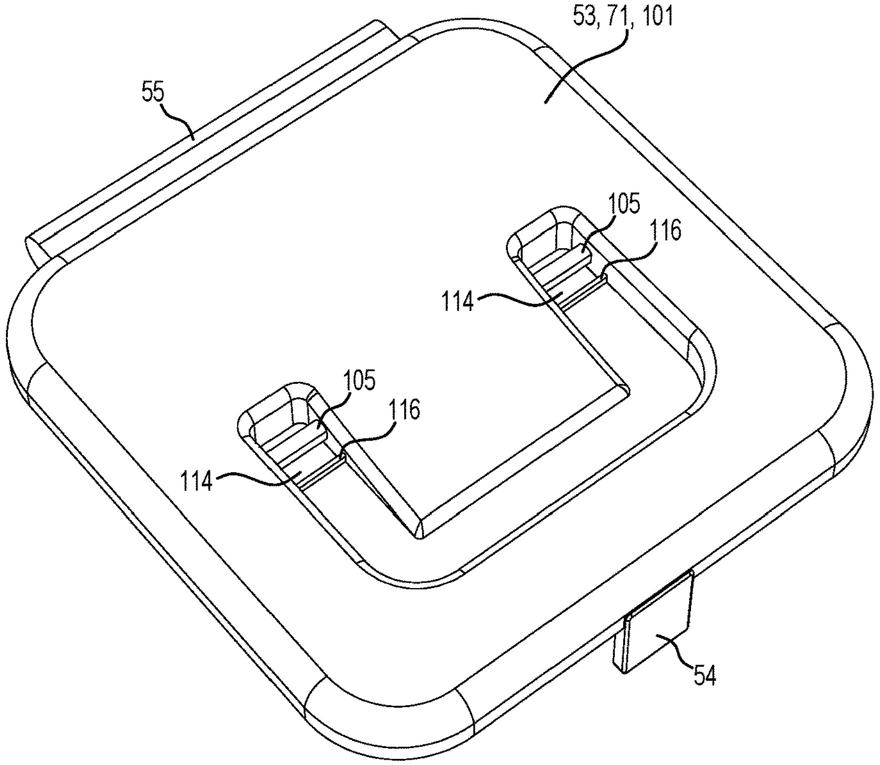
FIG. 10F is a schematic perspective view of the support of the holder.
Figure 10G:
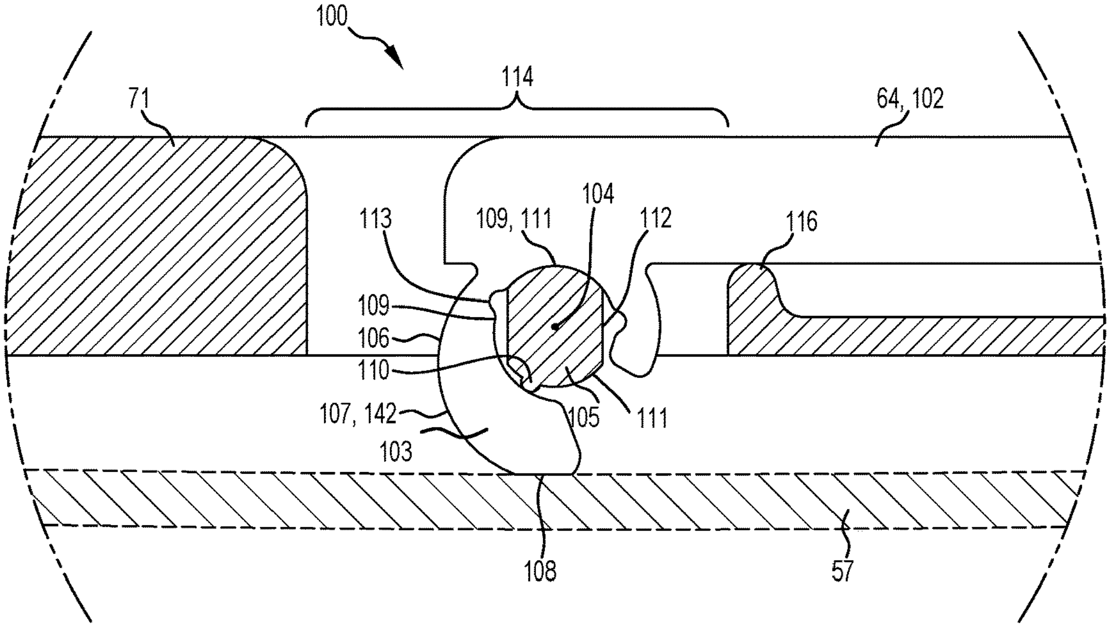
FIGS. 10G and 10H are enlarged views of the portion identified by the circles in FIGS. 10C and 10D respectively. The engaging member is in a holding configuration in FIG. 10G, in which the engaging member is operative for applying holding force, and a non-holding configuration in FIG. 10H, in which the engaging member is in a neutral position.
Figure 10H:
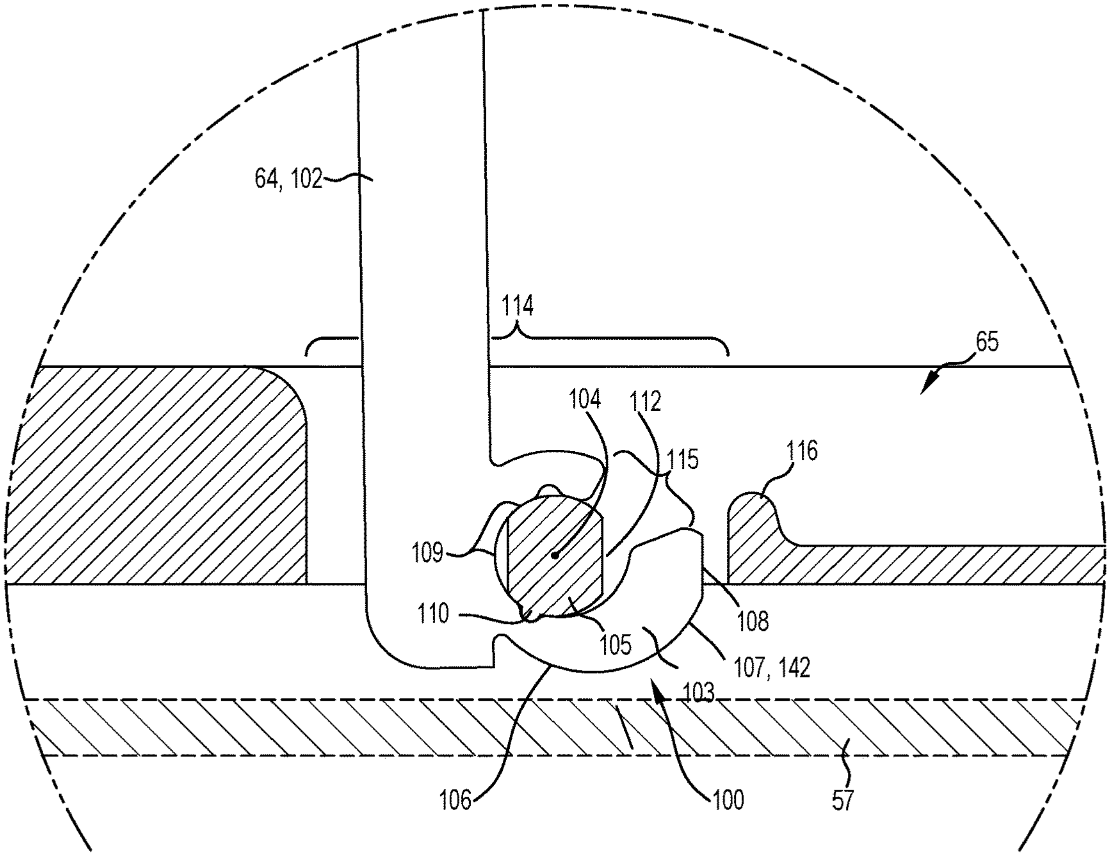

As can be best seen in FIGS. 10C, 10D, 10G and 10H, the cams 103 are pivotally mounted on posts 105 and have a radius of curvature that varies about the pivot axis 104 which is central to a longitudinal axis of the posts 105. The cam surfaces 142 have a reduced radii section 106 from the pivot axis 104 which faces the humidification chamber 24 when the engaging member 100 is pivoted into a neutral position, which is denoted by the lever 102 being pivoted away from the lid 71, see FIGS. 10D, 10E and 10G. When in the neutral position, the cam surfaces 142 are ideally spaced from the humidification chamber 24, as shown in FIGS. 10D and 10H, with the lid 71 closed.

However, it also possible that the cam surfaces 142 could contact, without pressing against, the humidification chamber 24. The cam surfaces 142 also have a first enlarged radii section 107 which faces and engages the humidification chamber 24 when the engaging member 100 is pivoted into an operating position, which is denoted by the lever 102 being pivoted toward the lid 71.

The cam surfaces 142 also includes a linear section 108 located toward an end of the cam surfaces 142, in which the linear section 108 engages the humidification chamber 24 when the engaging member 100 is moved into the operating position, see FIGS. 10C and 10G. The linear section 108 assists in stabilizing the cams 103 in the operating position when the lever 102 is pivoted downwardly toward the lid 71. In other words, the linear section 108 assists in preventing slippage of the cam surfaces 142 out of the operating position.

The engaging member 100 also includes an inner surface 109 on which the engaging member 100 pivots on the posts 105. As can be seen, the inner surface 109 of the engaging member 100 has upper and lower curved sections 111 of constant radius about the pivot axis 104 and oppositely disposed flat surfaces 112. In addition, the posts 105 have a raised notch 110 that preferably faces toward the humidification chamber 24, which bears against the inner surface 109 of the engaging member 100 and increases the friction between the inner surface 109 of the engaging member 100 and the post 105 when the cam surface 103 is moved into the operating position and presses against the humidification chamber 24. In other words, the notch 110 and the inner surface 109 of the engagement member 100 provide an interference fit that further assists in preventing slippage of the cam surfaces 142 out of the operating position.

In addition, the inner surface 109 of the engagement member 100 includes a indentation 113 that is located on the inner surface 109 of the engagement member 100 to receive the raised notch 110 when the engagement member 100 is pivoted into the neutral position, that is, with the handle is oriented away from the lid 71. When the notch 110 is received by the indentation 113, this can provide initial resistance to help maintain the handle 64 in the neutral position without any outside influence. However, a user can readily move the engaging member 100 by placing the hand on the lever 102.

As can be seen in the Figures, the cams 103 are mounted on posts 105 that extend across openings 114 in the lid 71, in which the cam surfaces 142 protrude out of the openings 114 to press against the humidification chamber 24 in the operating position and moves toward the opening in the neutral position.

In other words, the cams 103 are mounted in openings 114 and move between the neutral and operating positions in the openings 114.

As can best be seen FIGS. 10G and 10H, the posts 105 on which each engaging member 100 is mounted has a width defined between the flat surfaces 112 that interconnects the upper and lower curved surfaces 111. In addition, as can be seen in FIGS. 10G and 10H, the cams 103 includes a gap 115 that approximates the width of the posts 105, which allows the engaging member 100 to be assembled on the posts 105.

The support 101, and in particular, the top surface of the lid 71 has a recessed section 65 that receives the handle 64 including the levers 102 thereof, and suitably completely receives the handle 64 such that the handle 64 sits flush with the top surface of the lid 71 when the handle 64 is pivoted toward the lid 71 to locate the engaging member 100 in the operating position.

The recessed section 65 of the lid 71 has a lug 116 adjacent to the engaging member 100 that engages the lever 102 when the handle 64 is pivoted toward the lid to locate the engaging member in the operating position. In addition, an outer end 117 of the handle 64 also engages a contact point in the recessed section 65 of the lid 71 of the when the handle 64 is pivoted downwardly to the full extent.

Although not shown in detail in the Figures, the heater plate 29 of the humidification compartment 22 may include a biasing arrangement that biases the heater plate 29 toward the opening 72 of the humidification compartment 22. Operating the engaging member into operating position presses the humidification chamber against the heater plate which generates a holding force between the heater base 28 and the heater plate 29 which is at least in part equal to a biasing force of the biasing arrangement.

In addition, the humidification chamber 24 has a water tub cover 57 that is engaged by the engaging members 100. The water tub cover 57 may have reinforced sections that are engaged by the engaging members 100. The reinforced sections are not specifically shown in the Figures.

FIGS. 11A to 11H—Embodiment Having a Coupling that Acts Between the Humidification Chamber and the Body of the Compartment FIGS. 11A to 11H illustrate an apparatus 20 including a humidification chamber 24, such as a water tub 56 having a heater base 28 in which water 26 is evaporated into a gas stream 34, and a compartment 22 having a compartment body 32 with an opening 72 that receives the humidification chamber 24. The compartment 22 has a side wall 62 and a base wall 61 having a heater plate 29 on which the heater base 28 of the humidification chamber 24 is seated. The compartment 22 may have an optional biasing arrangement which mounts the heater plate 29 to the base wall 61 of the compartment 22. The apparatus 20 also has a coupling 118 that maintains the humidification chamber 24 in a position in the compartment body 32 and is operable to hold the heater base 28 against the heater plate 29 at a holding force which promotes thermal engagement therebetween.

It is within the scope of this embodiment that the apparatus 20 includes a support on which the coupling 118 is mounted and the support forms part of the humidification chamber 24 to maintain the humidification chamber 24 in the compartment 22.

It is also within the scope of this embodiment that the apparatus 20 includes a support to which the coupling 118 is mounted and that the support bears directly or indirectly against the humidification chamber 24 to maintain the humidification chamber 24 in position in the compartment 22 and hold the heater base 28 to the heater plate 29 at a holding force. In this example, the support may be mechanically connected to the humidification chamber 24 such that a user can remove the humidification chamber 24 from the compartment 22 when the coupling 118 is inactive.

According to this embodiment the support is in the form of a lid 71, and the coupling 118 is mounted to the lid 71 by being incorporated in the structure of the lid 71. The coupling 118 also has recesses in the form of coupling openings 131 on the inside face of the side walls 62 of the compartment 22 that receive the shafts 120 when in the active position.

Figure 11A:
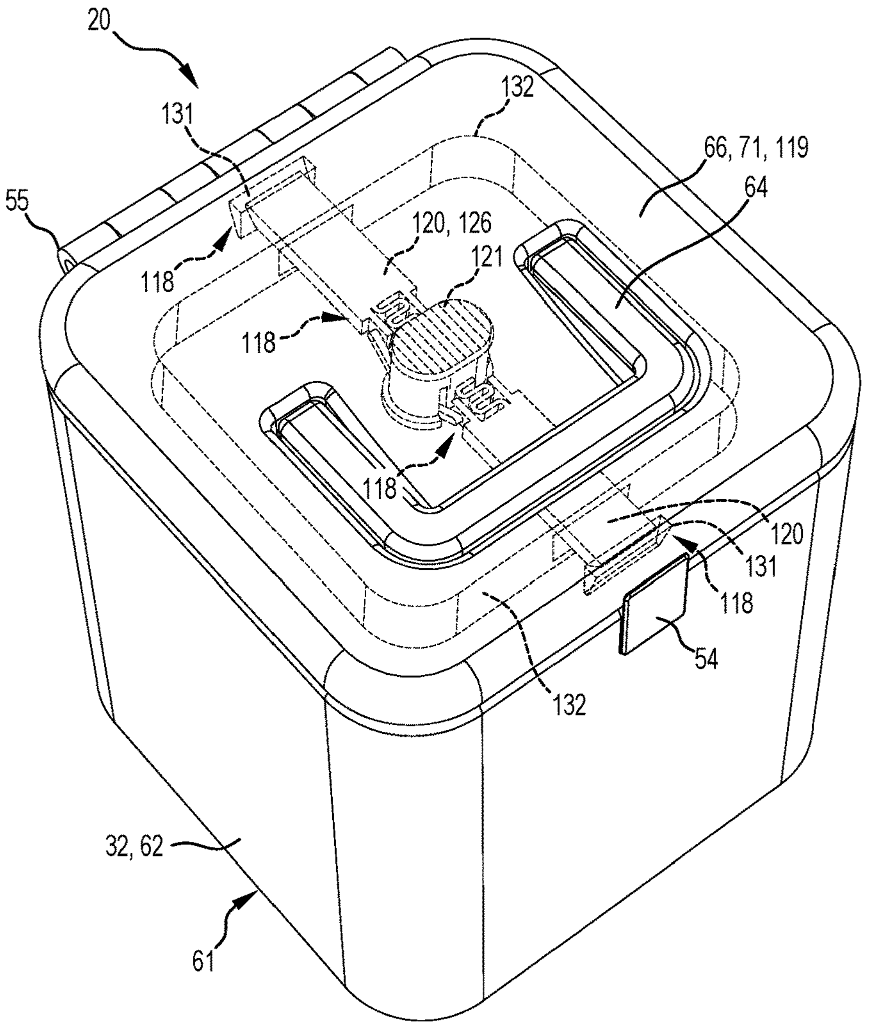
FIG. 11A is a schematic perspective view of an apparatus having a coupling including a push-button and a pair of shafts that act in a lateral direction between the humidification chamber and the compartment.
Figure 11B:
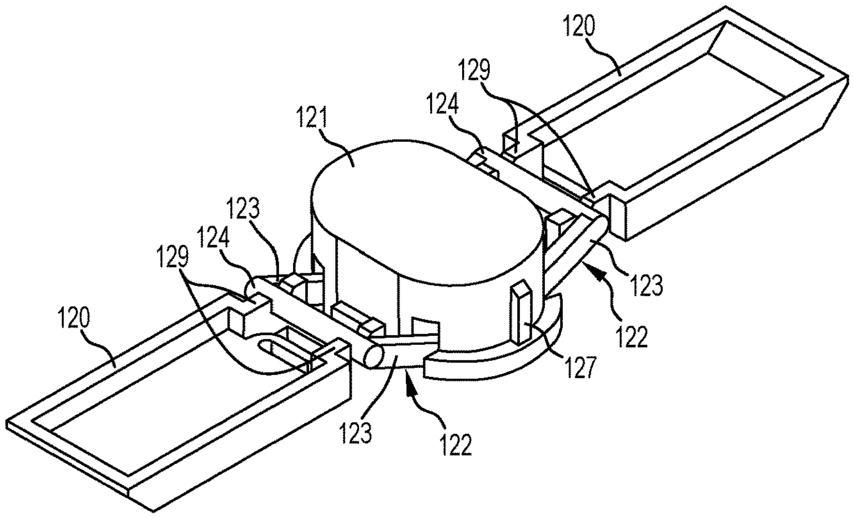
FIG. 11B is an enlarged view of the push-button and the shafts.
Figure 11C:
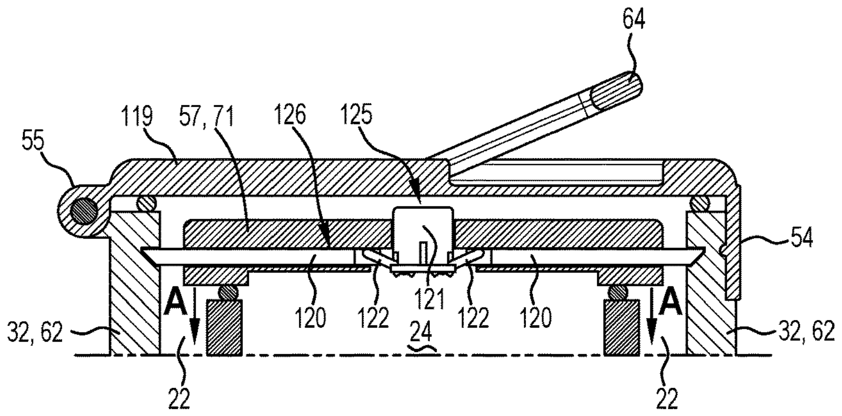
FIGS. 11C and 11D are schematic cross-sectional views of the apparatus in which the coupling is supported on an inner lid that presses against the humidification chamber, and the apparatus also has an outer lid that closes the compartment.
Figure 11D:
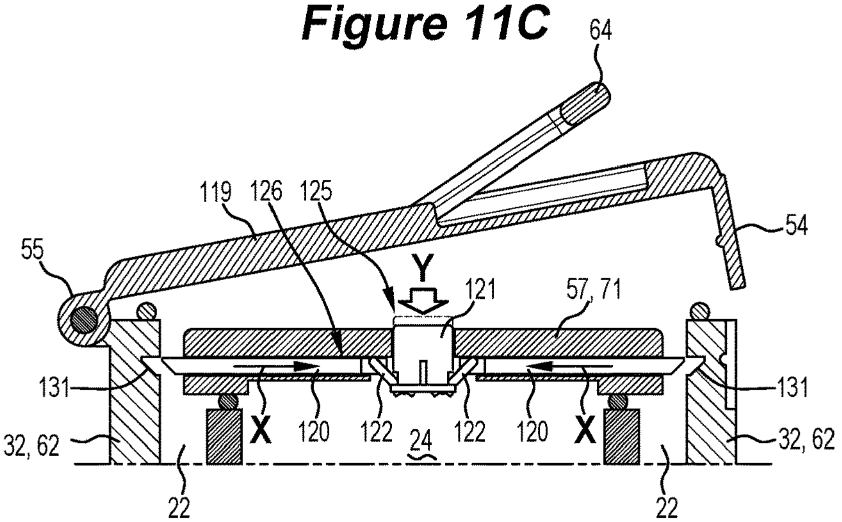

FIGS. 11C and 11D illustrate an example in which the lid 71 forms part of a water tub cover 57 of the humidification chamber 24. The gas stream 34 to be humidified may enter directly into the water tub 57 in accordance with FIG. 1A. Alternatively, it is also possible that the gas stream 34 to be humidified may enter the humidification compartment 22 before entering the humidification chamber 24 in accordance with the mode of operation of FIG. 1B. In this later situation, a separate outer cover 119, as shown in FIGS. 11C and 11D covers the opening 72 of the compartment 22.

Figure 11E:
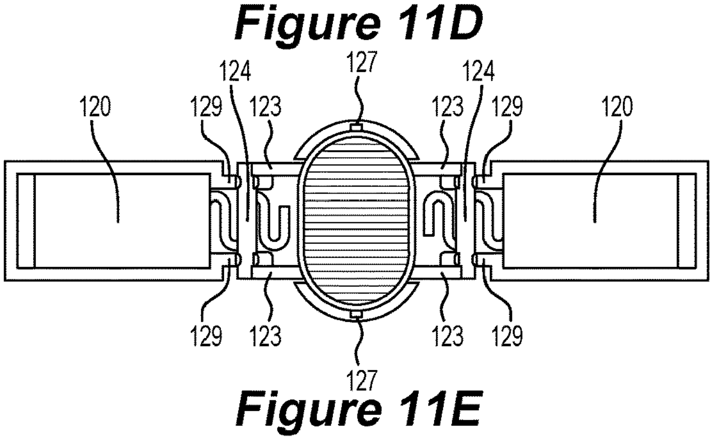
FIG. 11E is a plan view of the push-button shown in FIG. 11B.
Figure 11F:
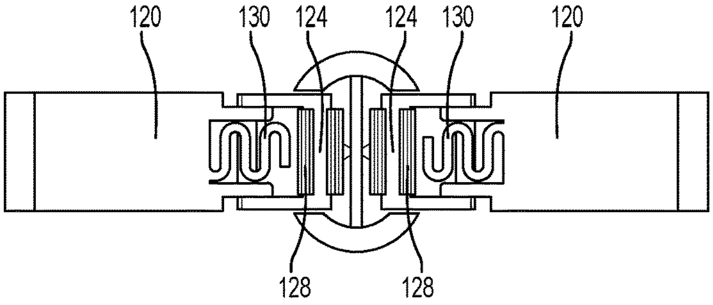
FIG. 11F is an underneath view of the push-button shown in FIG. 11B.
Figure 11G:
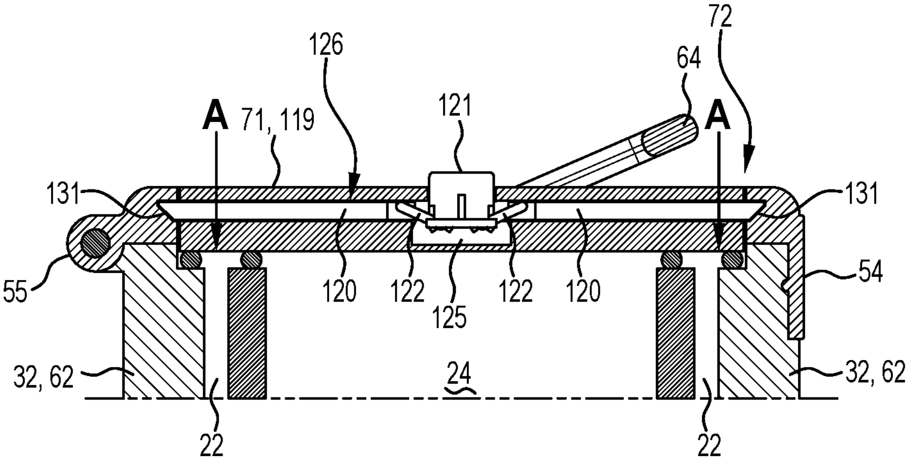
FIGS. 11G and 11H are schematic cross-sectional views of the apparatus in which the coupling is supported on a lid that presses against the humidification chamber and closes an opening of the compartment. The coupling is in an active position in FIGS. 11C and 11G and in an inactive position in FIGS. 11D and 11H.
Figure 11H:
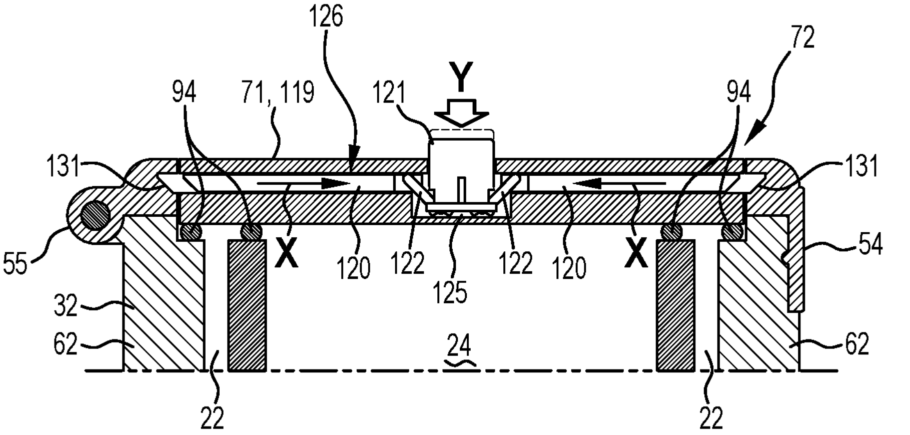

FIGS. 11G and 11H illustrate an example in which the lid 71 forms part of an outer cover 119 of the compartment 22 and presses against the humidification chamber 24. In this situation, the lid 71 may also include a sealing ring 94 for forming a seal. In any event, the coupling 118 is arranged to act on the compartment body 32 to maintain the humidification chamber 24 in position in the compartment body 32 and thereby hold the heater base 28 relative to the heater plate 29 at a holding force which promotes thermal engagement therebetween.

FIG. 11A represents the two examples mentioned above, wherein the coupling 118 may be incorporated in a lid in the form of the water tub cover 57 is illustrated in FIGS. 11C and 11D, or wherein the coupling 118 may be incorporated in a lid in the form of the outer cover 119 as illustrated in FIGS. 11G and 11H. In either example, the coupling 118 is operable such that the respective lid applies a pressing force, represented by the arrow "A" to the humidification chamber 24.

The lid 71 according to either one of the examples illustrated in FIGS. 11C, 11D, 11G and 11H is releasably connected to the compartment body 32 by the coupling 118.

The coupling 118 has a pair of shafts 120 that reciprocate in and out, a push-button 121 that moves up and down, and two linkage members 122 interconnecting the push-button 121 and the shafts 120. The linkage members 122 having a pair of spaced apart side plates 123 and cylindrical rods 124 at opposite ends. The coupling 118 is operable to move the shafts 120 in a reciprocating motion between an active position as shown in FIGS. 11C and 11G, in which the shafts 120 extends between and interconnects the lid of the humidification chamber 24 and the compartment body 32, and an inactive position as shown in FIGS. 11D and 11H in which the shafts 120 and do not engage the compartment 22. The lid 71 is joined to, or forms part of, the humidification chamber 24 so that when the coupling 118 is in the inactive position, a user can remove the humidification chamber 24 from the compartment 22 by the handle 64 pivotally mounted to the lid 71.

The push-button 121 is positioned in a first channel 125 (see FIGS. 11C, 11D, 11G and 11H) that is centrally located on the lid 71 and extends from an upper surface of the lid 71 so that the push-button 121 can be pressed in a direction away from the upper surface, in an up-and-down motion. The shafts 120 are positioned in second channels 126 that extend laterally to the push-button 121 and extend to opposite edges of the lid 71.

As can best be seen in FIGS. 11A, 11B and 11E the push-button 121 has a flat oval shape having a maximum cross-section at its curved ends, and a minimum cross-section at its flat sides. The oval shape maintains the pushbutton 121 in alignment within the first channel 125. In addition, the push-button 121 has two guide rails 127 on the outside surface of the push-button 121 at its maximum cross-section. The guide rails 127 are received by cooperating grooves in walls of the first channel 125 which help align the push-button 121 in the first channel 125. It will be appreciated that the push-button 121 could have any suitable geometry, including a body having circular or quadrangular shapes.

The coupling 118 includes an assembly in which the push-button 121 has two elongate socket formations 128 that are located on the underside of the push-button 121 at its minimum cross-section. The pivot rods 124 at one end of the linkage members 122 are snap fitted into each of the socket formations 128. In addition, the shafts 120 include a yoke formation 129 adjacent to the push-button 121 which have flexible openings into which the pivot rods 124 of the respective linkage members 122 are snap fitted, thereby interconnecting the shafts 120 to the push-button 121 via the linkage members 122. In use, pressing the push-button 121 downwardly in the direction of arrow is "Y" draws the linkage members 122 into an upright orientation which pulls both of the shafts 120 inwardly toward the push-button 121 in the direction of the arrows "X" and into the inactive position.

The coupling 118 also has compression springs 130 extending from the proximal ends of the shafts 120, which can best be seen in FIGS. 11E and 11F. The compression springs 130 engage either the body of the push-button 121 and/or the linkage 122 when the push-button 121 is pressed. The compression springs 130 bias the shafts 120 outwardly into the active position such that upon releasing the push-button 121, the shafts 120 will automatically move into the active position, as shown in FIGS. 11C and 11G.

The push-button 121 could also be held or locked in at least one of the active and inactive positions by a friction fit, detent, latch and so forth.

As best shown in FIGS. 11D and 11H, the inside face of the side walls 62 of the compartment 22 has coupling openings 131 which receive the shafts 120 when in the active position. Moreover, the shafts 120 extend laterally from the lid 71 of the humidification chamber 24. The shafts 120 are arranged to transfer forces from the humidification chamber 24 to the compartment body 32. The forces transferred can include reaction forces that are attributable to the holding force between the heater base 28 of the humidification chamber 24 and the header plate 29 of the humidification compartment 22.

The term "laterally" in the paragraph immediately above refers to a direction normal to the direction of the inner face of the side walls 62 of the compartment 22.

In addition, distal ends of the shafts 120 include chamfered surfaces, which allow a user to manually insert and push the humidification chamber 24 into the compartment 22 so the distal ends of the shafts 120 engage the interior surface of the side walls 62 of the compartment 22 and move into the coupling openings 131 of the side walls 62 of the compartment 22 when the humidification chamber 24 has been located with a holding force between the heater base 28 and the heater plate 29.

As described above, the apparatus 20 may have an optional biasing arrangement that mounts the heater plate 29 to the base wall 61. The biasing arrangement may urge the heater plate 29 upwards at a biasing force. The upwards biasing force could be greater than the downward force required to operate the push-button 121, so as soon as the shafts 120 are disengaged the humidification chamber 24 moves upward, and the shafts 120 away from the coupling opening 121. The user can then release the push-button 121 and the shafts 120 will not reengage because the humidification chamber 24 has moved upwardly.

The dashed line 132 in FIG. 11A represents a junction between the outer cover 119 and an outer frame 66 of the lid 71 that extends about the opening 72 of the compartment 22. The outer frame 66 can be fitted or retrofitted to the compartment body 32 in which the outer frame 66 has a separate body. For example, the outer frame 66 is connected to a rear wall of the compartment 22 by a hinge mounting 55, and a suitable latching device 54 is operable to attach the fun of the lid to the compartment, thereby allowing the outer frame to be hinged open if required. The coupling openings 131 arranged in an inner perimeter of the outer frame 66 or directly to the inside face of the side walls 62 of the compartment 22. As can be seen in FIGS. 11G and 11H, the top surface of the outer frame 66 is flush with the top surface of the outer cover 119.

Although not illustrated in the Figures, it will be appreciated that the outer frame 66, or at least the profile of the outer frame 66 may be integrally formed with the body of the compartment 22 to form an outer frame region. In this situation, the hinge mountings 55 and the latch device 54 will be omitted.

In addition, although not shown in the Figures, the coupling 118 could have a pull-button in addition, or instead of, the push-button 121 described above. The pull-button may have each of the features of the push-button described above, including to move the shafts 120 in reciprocating motion. Specifically, it will be appreciated that the pull-button can be operably connected to the shafts 120 so that pulling the pull-button outward moves the shafts inward, and releasing the pull-button allows the pull-button to move toward the lid and the shafts outward.

FIGS. 12A to 12D and FIGS. 13A and 13B—Embodiment Having a Coupling that Acts Directly Between the Humidification Chamber and the Humidification Compartment FIGS. 12A to 13B illustrate an apparatus 20 including a humidification chamber 24, such as a water tub 56 having a heater base 28 in which water 26 is volatilized, and a compartment 22 having a compartment body 32 with an opening 72 that receives the humidification chamber 24. The compartment 22 has a side wall 62 and a base wall 61 having a heater plate 29 that may or may not be supported on a biasing arrangement (not illustrated). The humidification apparatus 20 also has a coupling 118 that acts between the humidification chamber 24 and the compartment body 32 which holds the heater base 28 relative to the heater plate 29 by a holding force, denoted by the arrows "A" that is transferred to the side wall by the coupling 118. The coupling 118 promotes good thermal engagement between the heater base 28 and the heater plate 29.

In this embodiment, the coupling 118 is a snap fit connector, which may also be called a detent coupling. The snap fit connector includes a projection 132 that acts between the humidification chamber 24 and the compartment body 32. In the embodiment illustrated, the projection 132 may extend from the humidification chamber 24 which engages a catch piece 133 of the compartment 22. The catch piece 33 is located on an interior face of the side wall 62 of the compartment 22 and the projection 132 extends from the water tub 56. Suitably, the projection 132 extends from an upper region of the water tub 56 and may extend from the water tub cover 57.

Figure 12A:
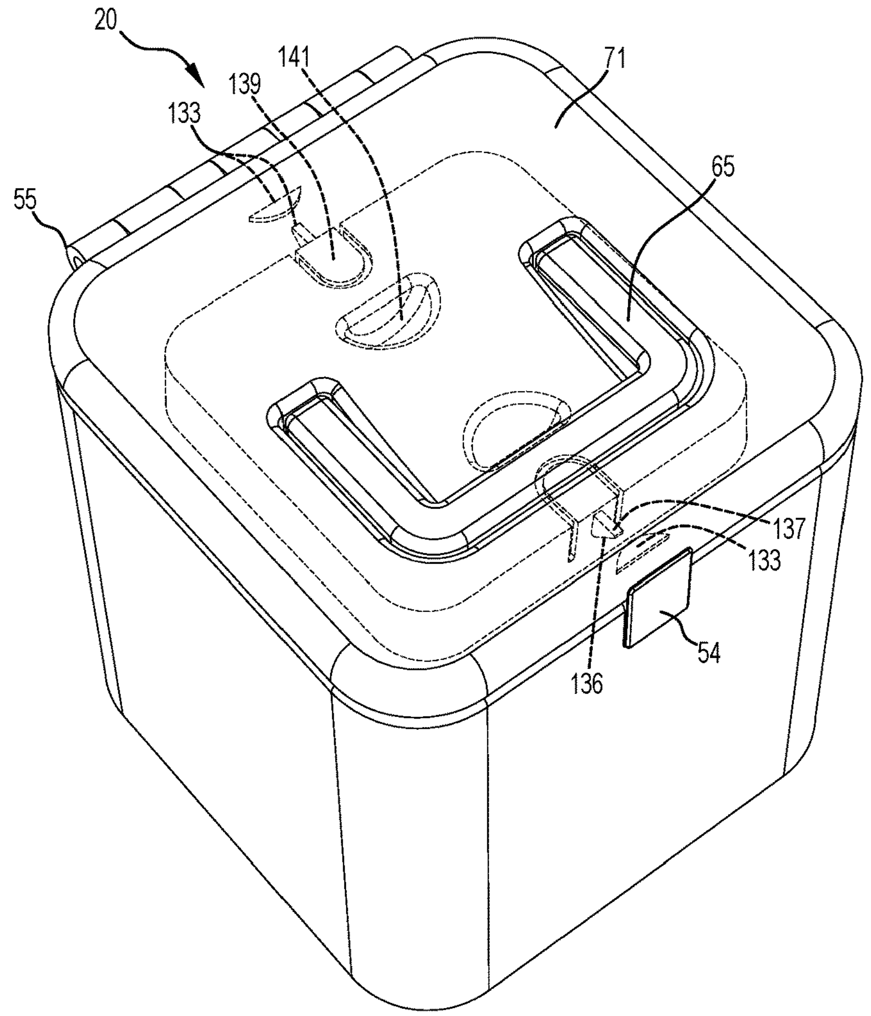
FIG. 12A is a schematic perspective view of an apparatus including a coupling having a snap fit connection that acts between humidification chamber and the compartment.
Figure 12B:
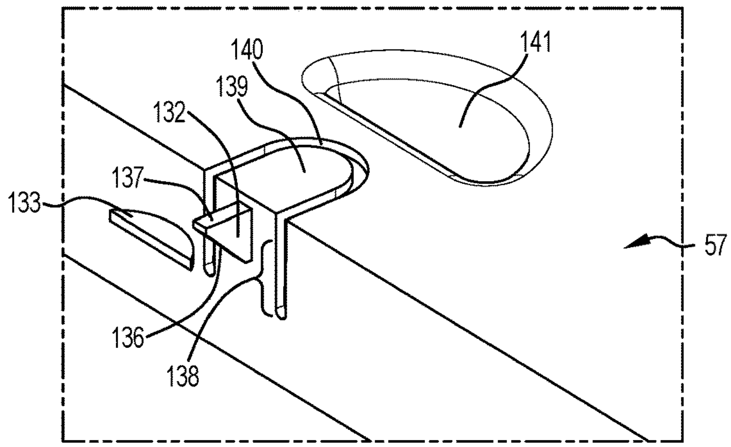
FIG. 12B is an enlarged view of the snap fit connection and a thumb rest.
Figure 12C:
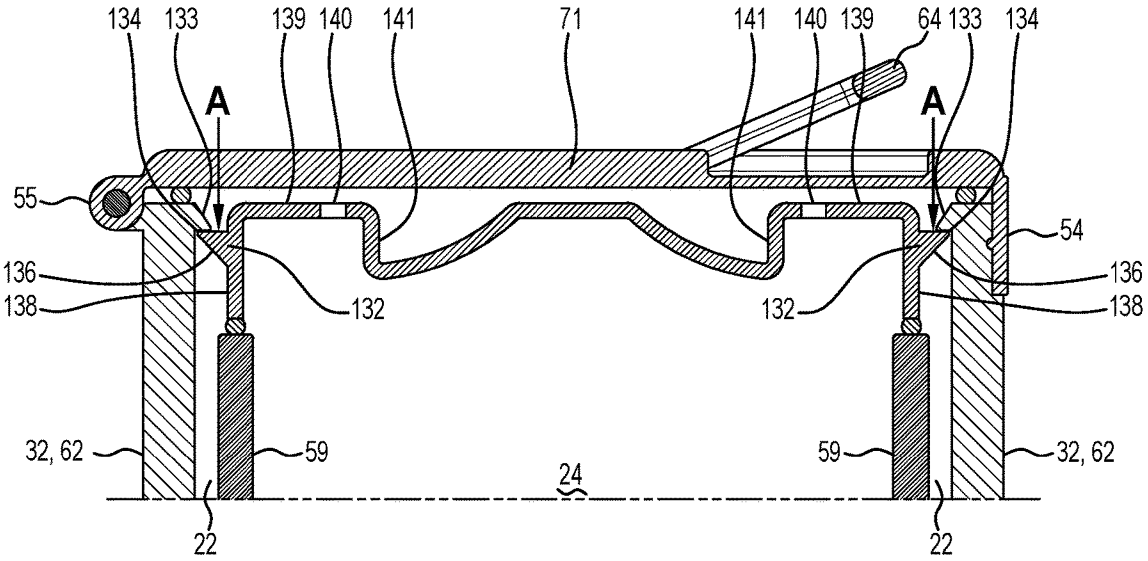
FIGS. 12C and 12D are cross-sectional views in which the coupling is in active and inactive positions respectively.

The apparatus 20 includes at least two snap fit connectors which are oppositely disposed. Although it is possible that the snap fit connectors maybe positioned on the front and rear walls, ideally, the snap fit connectors are disposed on, and act between opposite sides of the compartment 22. FIGS. 12A, 12B and 12C illustrate the snap fit connectors on front and rear sides of the compartment 22 that engage catch pieces 133 on the front and rear surfaces of the compartment 22, alternatively or additionally, the snap fit connectors may also be located to the left and right sides of the compartment 22 and the humidification chamber 24.

The catch pieces 133 may include at least one peak, and possibly a series of peaks arranged consecutively in a direction moving away from the opening 72 of the compartment 22. Each peak has an adjacent recess. FIGS. 12C, 12D, 13A and 13B illustrate embodiments in which the catch pieces 133 include a single peak.

When the humidification chamber 24 is installed in the compartment 22, the projection 132 frictionally engages and passes over the peak and moves into the adjacent recess. In the situation where a series of peaks are provided, the humidification chamber 24 can be located in an operative position at one of the recesses. However, the multiple peaks allows the humidification chamber 24 to be positioned in multiple operating positions and optionally at different holding forces between the heater plate 29 and the heater base 28 depending on which recess is engaged.

Each peak may be a lip, crest, rib, ridge, narrowing and so forth on the interior surface of the side wall of the compartment 22. Similarly, the recess may be any trough, valley and or plane that does not protrude as far as the peak.

Each peak has an upwardly facing tapered surface 134 that extends further into the compartment 22 moving away from the opening 72 of the compartment 22, and a downwardly facing undercut 135. As illustrated in FIGS. 12C, 12D, 13A and 13B, the undercut 135 steps inward from the peak of the catch piece 133. In other examples, however, the undercut may recede or decline from the peak. Although not illustrated, the peak may also have a planar surface that is substantially parallel or flush to the side wall 62 of the compartment 22.

The projection 132 extends at a normal angle from humidification chamber 24 and includes an inclined surface 136 that faces downwardly which has an outermost extremity, and an upwardly facing reaction surface 137. The reaction surface 137 is substantially horizontal.

To install the humidification chamber 24 into the apparatus 20, the projection of the humidification chamber 24 slides over the upwardly facing tapered surface 134 which causes the projection 132 to progressively shift inward until the projection 132 aligns with the recess of the catch piece 133. At this alignment, the projection 132 snaps or recoils into the adjacent recess so that the reaction surface 137 of the projection 132 engages the undercut 135 of the catch piece 133 in an active position. In the active position, the projection 132 extends laterally between the humidification chamber 24 and the compartment 22, and is active in providing a reaction force that counteracts the holding force between the heater plate 29 and the heater base 28. As described above with reference to other embodiments, the holding force may counteract part of, or all of, a biasing force of the biasing arrangement.

The coupling 118 includes a resiliently flexible section 138 that is connected to the humidification chamber 24, and the projection 132 is connected to the resiliently flexible section 138 which allows the projection 132 to shift as a cantilever about the resiliently flexible section 138. The coupling 118 also has a finger tab 139 connected to the projection 132 to allow a user to move the projection 132.

In the embodiment shown in the FIGS. 12A to 12D, the resiliently flexible section 138 extends co-planar with the side wall 59 of the humidification chamber 24 and the projection 132 extends outwardly of the resiliently flexible section 138. As can best be seen in FIG. 12B, the projection 138 is oriented upright and is joined to a base that is connected to the resiliently flexible section 138. The finger tab 139 extends perpendicularly to the base in a direction inwardly of the resiliently flexible section 138. The finger tab 139 has a horizontal planar surface that can be pressed by a user in the direction of arrows "Z" in FIG. 12D. The finger tab 139 is disposed on the opposite side of resiliently flexible section 138 to the projection 132 and has an upper surface that is substantially parallel to the upper surface of the humidification chamber 24, or the water tub cover 37.

The finger tab 139 can have finger grip ribs or grooves to improve gripping. As can be seen, a clearance gap 140 is provided about the finger tab 139 to allow the tab 139 to move freely. The clearance gap 140 also extends about the resiliently flexible section 138. In another example that has not been illustrated, the water tub cover 57 may be continuous and there is no clearance gap 140. Rather, an elastic and/or flexible material may interconnect the finger tab 139 to the water tub cover 57 or to the side wall 59 of the humidification chamber 24. The elastic and/or flexible material may be overmoulded to the finger tab 139, the water tub cover 57 and/or to the side wall of the humidification chamber 24. The advantage of the elastic and/or flexible material is that it can allow movement of the finger tab 139 so that the water tub cover 57 provides a gas tight closure on the humidification chamber 24.

Figure 12D:
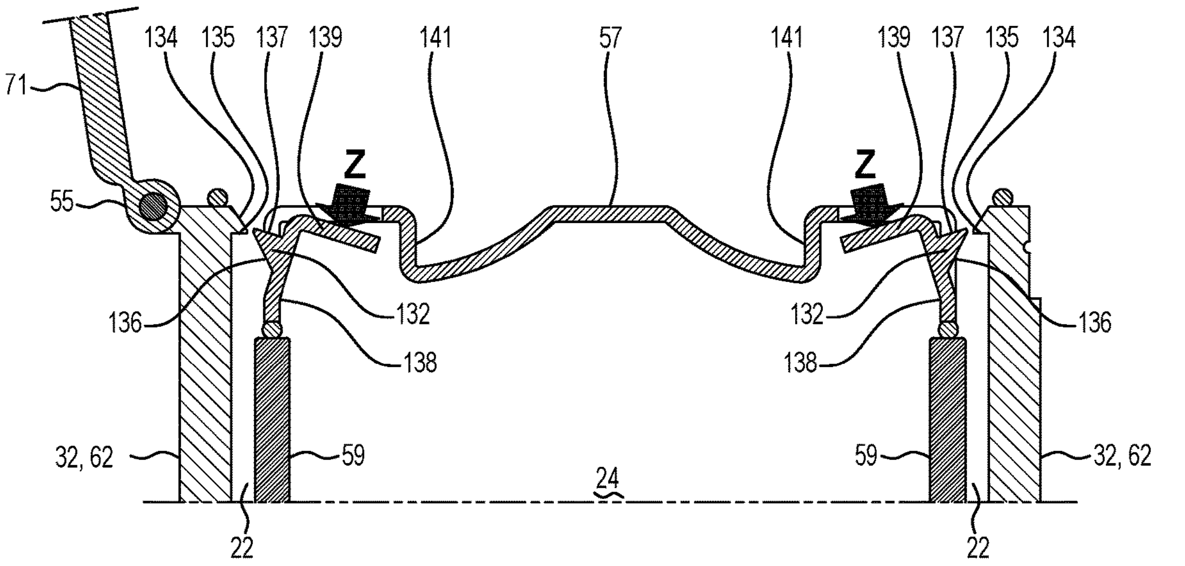

In addition, the water tub cover 57 has a thumb stop 141 adjacent to the finger tab 139 against which a user's thumb can rest which allows the finger tab 139 to be pressed in the direction of arrows "Z" as shown in FIG. 12D using a single-handed pinch action between the thumb and one or more fingers. Although it is possible that the thumb stop 141 may be a protrusion extend above the top wall of the water tub cover 57, ideally, the thumb stop 141 is located below the top wall of the water tub cover 57 as shown in the FIGS. 12A to 12D.

To release the coupling 118, a user can place a thumb in the thumb stop 141 and press down on the finger tab 139 with one or more fingers which rocks the projection 132 away from the catch piece 133. At the same time, the user can lift and remove the chamber 24 from the compartment 22.

Figure 13A:
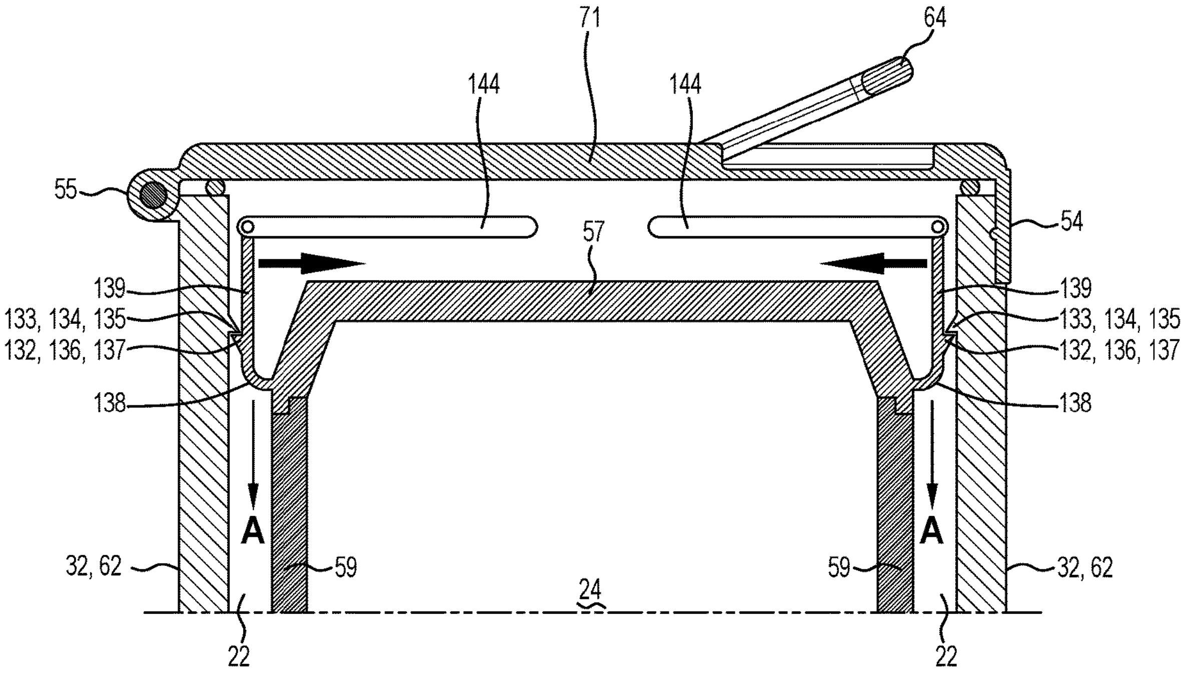
FIGS. 13A and 13B are cross-sectional views of another apparatus including a coupling having a snap fit connection that acts between the humidification chamber and the compartment, in which the coupling is in active and inactive positions respectively and has handles for operating the snap fit connection.
Figure 13B:
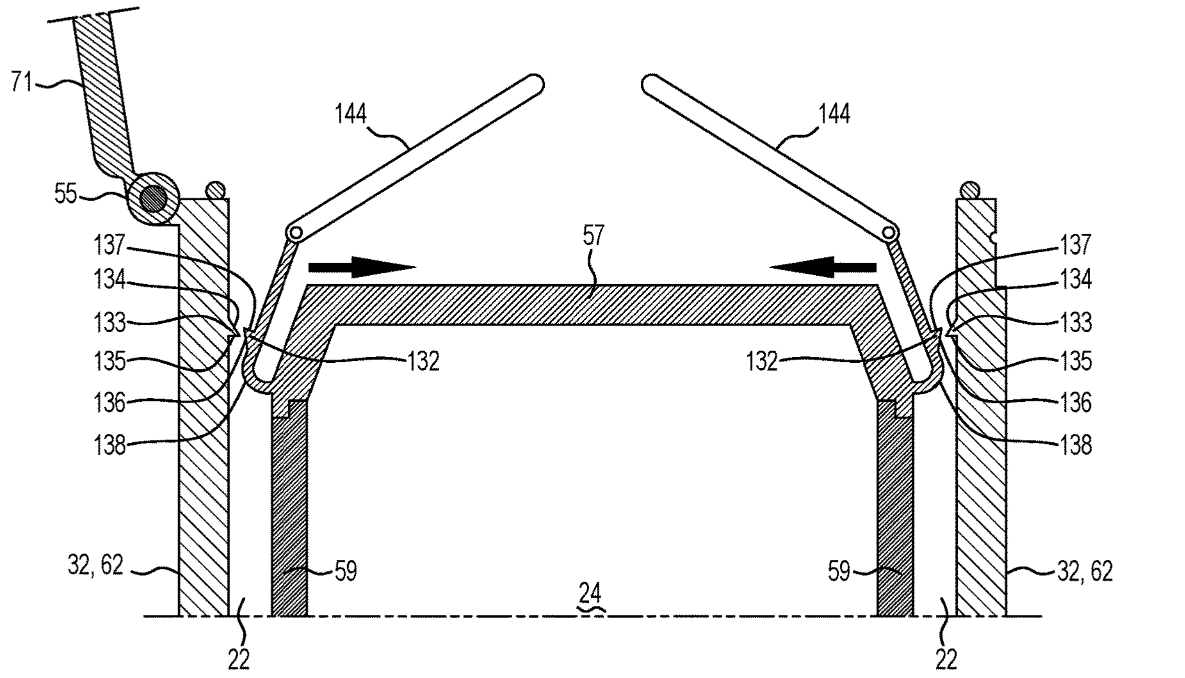

FIGS. 13A and 13B illustrate an alternative example, in which the resiliently flexible section 138 that extends outwardly from the side wall 59 of the humidification chamber 24 and the projection 132 has a base and the inclined surface 136 extending outwardly of the base that extends upwardly from the resiliently flexible section 138. The finger tab 139 is connected to the base of the projection 132 and extends upward from the projection 132. In one arrangement, the finger tab 139 may extend above the humidification chamber 24, or alternatively be arranged below an upper surface of the humidification chamber 24. The finger tab 139 may also be arranged inwardly for the projection 132, and may for example, be aligned with the side wall of the humidification chamber 24.

The projection 132 in FIGS. 13A and 13B also have a horizontal reaction surface 137 which cooperates with a catch piece 133 that is formed and has the same configuration as the catch piece 133 shown in FIGS. 12C and 12D. The horizontal reaction surfaces 137 transfers forces to the compartment 22 allowing the coupling to transfer a holding force which may in part, or in full, oppose the biasing force acting against the heater base 28.

According to this example, when the humidification chamber 24 is installed, the projection 132 shifts inward toward the humidification chamber 24 and recoils or snaps outward when the reaction surface 137 aligns with the undercut 135 of the catch piece 133. A finger tab 139 extending above the projection 132 allows a user to push the finger tab 139 inwardly or toward the humidification chamber 24 to release the projection 132 from the catch piece 133. The finger tabs 139 may have grooves or finger grips. To release the humidification chamber 24, the finger tabs 139 may be moved toward each other in the direction of the arrows directly by a user. The finger tabs 139 may also have holes that allow the humidification chamber 24 to be lifted.

The apparatus may also have optional handgrips 144 that are pivotally connected to each of the finger tabs 139. A user can release the humidification chamber 24 by grasping the two handgrips 144 in one hand which draws the handgrips 144 toward each other, thereby releasing the projections 132 from the catch pieces 133, and allow the humidification chamber 24 to be lifted simultaneously.

It is within the scope of the present embodiment that the catch piece can be an element on the humidification chamber 24 and that the shiftable projection 132 can be an element on the compartment 22.

Those skilled in the art of the present invention will appreciate that many variations or modifications may be made to the preferred embodiment without departing from the spirit and scope of the present invention.

Whilst a number of specific apparatus and method embodiments have been described, it should be appreciated that the apparatus and method may be embodied in many other forms. For example, the humidification chamber 24 may have a lid that also seals the humidification compartment 22, for example, as illustrated in FIGS. 5A to 5D, and FIGS. 6A to 6D. Alternatively, the lid of the humidification chamber 24 may have no role in sealing the humidification compartment 22, for example, as illustrated in FIGS. 3A to 4L and 7A to 10H. However, it will also be appreciated that an apparatus having the same or substantially the same coupling as shown in FIGS. 7A to 10H could also be used to seal the humidification compartment 22 by making modifications at least to the lid. By way of example, the lid of the humidification chamber 24 in FIGS. 11C and 11D is illustrated as sealing the humidification chamber 24 only, yet a similar lid having similar coupling features is illustrated as sealing both the humidification chamber 24 and the humidification compartment 22 in FIGS. 11G and 11H. Similar modifications could be applied to the lids in FIGS. 7A to 10H so that the pressing forces applied to the humidification chamber 24 could also be used to create a seal between the lid of the humidification chamber 24 and the humidification compartment 22.

In another example, the heater plate 29 may be fixedly mounted to a base wall of the compartment 22, or alternatively, the heater plate 29 may be mounted on a biasing arrangement that allows the heater plate 29 to move upward and downward as the case may require in response to the holding or pressing force. In any event, the presence or absence of the biasing arrangement does not change the manner in which the coupling between the humidification chamber and the humidification compartment operates.

In the claims which follow, and in the preceding description, except where the context requires otherwise due to express language or necessary implication, the word "comprise" and variations such as "comprises" or "comprising" are used in an inclusive sense, i.e. to specify the presence of the stated features but not to preclude the presence or addition of further features in various embodiments of the apparatus and method as disclosed herein.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "front" and "rear", "inner" and "outer", "above", "below", "upper" and "lower" and the like are used as words of convenience to provide reference points and are not to be construed as limiting terms. The terms "vertical" and "horizontal" when used in reference to the humidification apparatus throughout the specification, including the claims, refer to orientations relative to the normal operating orientation.

Furthermore, invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, for example, aspects of one embodiment may be combined with aspects of another embodiment to realize yet other embodiments. Further, each independent feature or component of any given assembly may constitute an additional embodiment.

| Reference Numeral Table | |
|---|---|
| apparatus | 20 |
| humidification compartment | 22 |
| humidification chamber | 24 |
| receptacle | 25 |
| water | 26 |
| heater base | 28 |
| heater plate | 29 |
| blower | 30 |
| seal | 31 |
| compartment body | 32 |
| gas stream | 34 |
| biasing force | 35 |
| force | 35A |
| compartment outlet | 36 |
| chamber inlet | 37 |
| first central opening | 37A |
| passageway | 38 |
| actuator | 39 |
| chamber outlet | 40 |
| second central opening | 40A |
| compartment inlet | 41 |
| latch | 43 |
| conduit | 44 |
| latching members | 45 |
| patient interface | 46 |
| retention members | 47 |
| recess | 48 |
| finger tabs | 49 |
| biasing spring | 50 |
| clearance region | 51 |
| depression | 52 |
| holder | 53 |
| latching device | 54 |
| hinge mounting | 55 |
| water tub | 56 |
| water tub cover | 57 |
| outer layer | 57A |
| inner layer | 57B |
| bottom wall (of water tub) | 58 |
| side wall (of water tub) | 59 |
| peripheral rim | 60 |
| base wall (of compartment 22) | 61 |
| side wall (of compartment 22) | 62 |
| front compartment wall | 62a |
| left compartment wall | 62b |
| rear compartment wall | 62c |
| right compartment wall | 62d |
| strap | 63 |
| handle | 64 |
| recessed section | 65 |
| frame | 66 |
| top wall | 67 |
| outer skirt | 68 |
| inner skirt | 69 |
| central opening | 70 |
| lid | 71 |
| opening (of compartment 22) | 72 |
| closure mechanism | 73 |

-continued

| Reference Numeral Table | |
|---|---|
| first engagement formation | 74 |
| second engagement formation | 75 |
| lip | 76 |
| groove | 77 |
| ring body | 78 |
| attachment formation | 79 |
| fingers | 80 |
| rod | 81 |
| sleeves | 82 |
| riser section | 83 |
| top flange | 84 |
| side skirts | 85 |
| front skirt | 86 |
| block | 87 |
| overhang | 88 |
| outer shell | 89 |
| top panel | 90 |
| rear panel | 91 |
| upper surface (of the rear wall) | 93 |
| sealing gasket | 94 |
| dividers | 95 |
| extension (of the top wall 67) | 96 |
| reduction (of the outer shell 89) | 97 |
| claws | 98 |
| saddle formations | 99 |
| engagement member | 100 |
| support | 101 |
| lever | 102 |
| cam | 103 |
| cam surface(s) | 142 |
| pivot axis | 104 |
| posts | 105 |
| reduced radii section | 106 |
| enlarged radii will section | 107 |
| linear section | 108 |
| inner surface | 109 |
| raised notch | 110 |
| curved section | 111 |
| flat surface | 112 |
| indentation | 113 |
| lid opening | 114 |
| gap | 115 |
| lug | 116 |
| outer end (of handle/lever) | 117 |
| coupling | 118 |
| outer cover | 119 |
| shafts | 120 |
| push-button | 121 |
| linkage | 122 |
| flat plates | 123 |
| rods | 124 |
| first channel | 125 |
| second channel | 126 |
| guide rails | 127 |
| socket formation | 128 |
| yoke formation | 129 |
| compression spring | 130 |
| coupling opening | 131 |
| projection | 132 |
| catch piece | 133 |
| tapered surface (of catch piece 133) | 134 |
| undercut | 135 |
| inclined surface (of projection 132) | 136 |
| horizontal reaction surface | 137 |
| resiliently flexible section | 138 |
| finger tab | 139 |
| clearance gap | 140 |
| thumb stop | 141 |
| handgrips | 144 |
| underside | 145 |
| central hub | 146 |
| guide sleeves | 147 |
| lower limb | 148 |
| upper limb | 149 |
| middle divider | 150 |
| first web | 151 |
| second web | 152 |

-continued

| Reference Numeral Table | |
|---|---|
| lower slot | 153 |
| upper slot | 154 |
| first biasing | 155 |
| finger ring | 156 |
| inner top wall | 157 |
| outer top wall | 158 |
| air cavity | 159 |
| first passageway | 160 |
| second passageway | 161 |
| channel | 162 |
| spillway | 163 |
| central hub | 146 |
| guide sleeves | 147 |

The invention claimed is:

1. A humidification apparatus including:

a humidification chamber having a heater base;

a compartment having a heater plate and a compartment body that receives the humidification chamber;

a coupling that acts between the humidification chamber and the compartment body, the coupling imparting a holding force to hold the heater base of the humidification chamber relative to the heater plate of the compartment, the coupling comprising at least one laterally-moving latch mounted to the humidification chamber and at least one recess positioned on the compartment body, the at least one laterally-moving latch and the at least one recess together holding the humidification chamber relative to the compartment body while being configured to enable the humidification chamber to be removed from the compartment body with a single hand; and an actuator for the at least one laterally-moving latch, the actuator being configured such that the humidification chamber is removed from the compartment body without a user releasing the actuator.

2. The humidification apparatus according to claim 1, wherein the holding force acts against a biasing force applied by a biasing mechanism.

3. The humidification apparatus according to claim 2, wherein the biasing mechanism is:

a) in or part of the heater plate;

b) in or part of the heater base;

c) in or part of the humidification chamber; or d) in or part of the compartment body.

4. The humidification apparatus according to claim 1, wherein the holding force is a pressing force that actively presses the heater base to the heater plate when the humidification chamber is in an operating position in the compartment body.

5. The humidification apparatus according to claim 1, wherein the coupling acts in a direction transverse to a direction of insertion of the humidification chamber into the compartment body.

6. The humidification apparatus according to claim 1, wherein the at least one recess is in a wall of the compartment body.

7. The humidification apparatus according to claim 6, wherein manipulation of the actuator can:

retract the at least one laterally-moving latch to enable insertion of the humidification chamber into the compartment body; and/or retract the at least one laterally-moving latch from the at least one recess of the wall of the compartment body to remove the humidification chamber from the compartment body.

8. The humidification apparatus according to claim 6, wherein the at least one laterally-moving latch comprises at least one sliding shaft that can extend into the at least one recess located on the wall of the compartment body to hold the humidification chamber relative to the compartment body.

9. The humidification apparatus according to claim 1, wherein the actuator comprises a biasing member that can move the at least one laterally-moving latch from a retracted position to an extended position.

10. The humidification apparatus according to claim 1, wherein the at least one laterally-moving latch comprises at least one slidable shaft that moves between:

i) an active position in which the at least one slidable shaft acts between the humidification chamber and compartment body and in which the at least one slidable shaft is received by and engages the at least one recess of the compartment body; and ii) an inactive position in which the at least one slidable shaft is disengaged from the at least one recess and the humidification chamber can be removed from the compartment body.

11. The humidification apparatus according to claim 10, wherein the coupling further comprises at least one finger tab capable of moving the at least one slidable shaft.

12. The humidification apparatus according to claim 10, wherein the coupling further comprises a biasing member that can move the at least one slidable shaft from the inactive position to the active position.

13. The humidification apparatus according to claim 12, wherein the coupling comprises two slidable shafts that are active from opposed sides of the humidification chamber and wherein the coupling further comprises two recesses on the compartment body.

14. The humidification apparatus according to claim 13, wherein the coupling comprises two finger tabs and the two slidable shafts each comprise one of the two finger tabs of the coupling, and wherein the two finger tabs can be squeezed toward each other to move the two slidable shafts into the inactive position and released to allow the biasing member to move the two slidable shafts outward.

15. The humidification apparatus according to claim 13, wherein each of the two slidable shafts have a chamfered surface on an underside of an outer end of each of the two slidable shafts that engage the compartment body and move inwardly against the biasing member when the humidification chamber is inserted into the compartment body, and wherein, when the outer end of each of the two slidable shafts align with the two recesses, the biasing member can move the two slidable shafts into engagement with the two recesses.

16. The humidification apparatus according to claim 13, wherein the two recesses are arranged on the compartment body so that as the humidification chamber approaches an operating position within the compartment body the heater base and heater plate engage one another, and wherein outer ends of the two slidable shafts are received by the two recesses in the active position when a force is applied to the humidification chamber, and wherein the two slidable shafts maintain the holding force when received by the two recesses after said force is removed from humidification chamber.

17. The humidification apparatus according to claim 1, wherein the compartment body receives the humidification chamber vertically.

18. The humidification apparatus according to claim 1, further comprising a lid that encloses the humidification chamber within the compartment body.

19. The humidification apparatus of claim 1, wherein the at least one laterally-moving latch is connected to the actuator, the actuator comprising at least one finger tab, the at least one finger tab being configured to be squeezed to retract the at least one laterally-moving latch from the at least one recess.

20. The humidification apparatus of claim 19, wherein the at least one laterally-moving latch, the actuator and the at least one finger tab are recessed below an upper surface of the humidification chamber.

* * * * *